US010350306B2

(12) United States Patent
Sieving et al.

(10) Patent No.: US 10,350,306 B2
(45) Date of Patent: Jul. 16, 2019

(54) METHODS AND COMPOSITIONS FOR TREATING GENETICALLY LINKED DISEASES OF THE EYE

(71) Applicant: The United States of America, as represented by THE SECRETARY, DEPT. OF HEALTH AND HUMAN SERVICES, Washington, DC (US)

(72) Inventors: Paul Albert Sieving, Bethesda, MD (US); Ronald Avery Bush, Gaithersburg, MD (US); Peter C. Colosi, San Anselmo, CA (US); Yong Zeng, Potomac, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 15/876,821

(22) Filed: Jan. 22, 2018

(65) Prior Publication Data

US 2018/0214577 A1     Aug. 2, 2018

Related U.S. Application Data

(63) Continuation-in-part of application No. 14/766,842, filed as application No. PCT/US2014/016389 on Feb. 14, 2014, now Pat. No. 9,873,893.

(60) Provisional application No. 61/765,654, filed on Feb. 15, 2013, provisional application No. 61/815,636, filed on Apr. 24, 2013.

(51) Int. Cl.
| | |
|---|---|
| *A61K 48/00* | (2006.01) |
| *A61P 27/02* | (2006.01) |
| *A61K 38/17* | (2006.01) |
| *A61K 9/00* | (2006.01) |
| *A61K 45/06* | (2006.01) |
| *A61K 31/592* | (2006.01) |
| *A61K 31/593* | (2006.01) |
| *C12N 15/86* | (2006.01) |
| *A61K 33/06* | (2006.01) |
| *A61K 31/5377* | (2006.01) |
| *A61K 31/573* | (2006.01) |

(52) U.S. Cl.
CPC ........ *A61K 48/0058* (2013.01); *A61K 9/0048* (2013.01); *A61K 31/5377* (2013.01); *A61K 31/573* (2013.01); *A61K 31/592* (2013.01); *A61K 31/593* (2013.01); *A61K 33/06* (2013.01); *A61K 38/1709* (2013.01); *A61K 45/06* (2013.01); *A61P 27/02* (2018.01); *C12N 15/86* (2013.01); *A61K 9/0051* (2013.01); *C12N 2750/14143* (2013.01); *C12N 2830/008* (2013.01)

(58) Field of Classification Search
CPC ................. C12N 15/86; C12N 7/00; C12N 2750/14143; C12N 2830/008; C12N 2830/42; A61K 9/0046; A61K 38/1709; A61K 48/00; A61K 48/0058; C07K 14/47
See application file for complete search history.

(56) References Cited

U.S. PATENT DOCUMENTS 9,873,893 B2    1/2018  Sieving et al.

FOREIGN PATENT DOCUMENTS

| JP | 2012-016359 | 1/2012 |
|---|---|---|
| WO | WO 2008/065430 | 6/2008 |
| WO | WO 2011/034947 | 3/2011 |
| WO | WO 2012/112578 | 8/2012 |

OTHER PUBLICATIONS

Kay, Nature Reviews Genetics, advance online publication, pp. 1-13, published online Apr. 6, 2011.*
Misra, JAPI, 61: 127-133, 2013.*
Samiy, J. of Ophthalmic and Vision Research, 9(4): 506-509, 2014.*
Bethke, accessed from https://www.reviewofophthalmology.com/article/the-future-of-gene-therapy on Dec. 10, 2018, published Apr. 5, 2016.*
Al-Saikhan, Saudi Journal of Ophthalmology 27, 107-111, 2013.*
Official Action with English Translation for Japan Patent Application No. 2015-558144, dated May 22, 2018 6 pages.
Hauck, Bernd, et al., "Undetectable Transcription of cap in a Clinical AAV Vector: Implications for Preformed Capsid in Immune Responses," Molecular Therapy, Jan. 2009, vol. 17, No. 1, Oct. 21, 2008 (Oct. 21, 2008), pp. 144-152.
Kayleigh, Kaneshiro, et al., "Evaluation of Viral and Human Retinal Promoters in AAV8 Vectors", Investigative Ophthalmology & Visual Science—10VS—ARVO Meeting Abstracts, vol. 52, No. Suppl., Apr. 22, 2011 (Apr. 22, 2011) p. 491.
Langmann, T., et al., "CRX controls retinal expression of the X-linked juvenile retinoschisis (RS1) gene," Nucleic Acids Eesearch, vol. 36, No. 20, Oct. 16, 2008 (Oct. 16, 2008) pp. 6523-6534.
Min, et al., "Prolonged Recovery of Retinal/Function After Gene therapy in a Rs1h-Deficient Mouse Model of X-linked Juvenile Retinoschisis," Molecular Therapy, Oct. 2005, Nature Publishing Group GB, vol. 12, No. 4, Jul. 18, 2005 (Jul. 18, 2005), pp. 644-651.
Nicoud, Marjorie, et al., "Development of photoreceptor-specific promotors and their utility to investigate EIAV lentiviral vector mediated gene transfer to photoreceptors", Journal of Gene Medicine, Dec. 2009, John Wiley & Sons, Inc, US, vol. 9, No. 12, Oct. 29, 2007 (2007-18-29) pp. 1015-1023.
Park, T.K., et al., "Intravitreal delivery of AAV8 retinoschisin results in cell type-specific gene expression and retinal rescue in the Rs1-K0 mouse," Gene Therapy, Jul. 2009, vol. 16, No. 7, May 21, 2009 (May 21, 2009), pp. 916-926, XP055113.

(Continued)

*Primary Examiner* — Thaian N Ton
(74) *Attorney, Agent, or Firm* — Sheridan Ross P.C.

(57) ABSTRACT

Expression vectors and therapeutic methods of using such vectors in the treatment of diseases of the eye resulting from failure to produce a specific protein in the eye, or the production of a non-functional protein in the eye.

13 Claims, 13 Drawing Sheets

Specification includes a Sequence Listing.

(56) References Cited

OTHER PUBLICATIONS

Pasqualina, Colella, et al., "Gene Therapy of Inherited Retinopathies: A Long and Successful Road from Viral Vectors to Patients," Human Gene Therapy, vol. 23, No. 8, Aug. 2012 (Aug. 2012), pp. 796-807.

Takada, Y., et al., "Synaptic Pathology in Retinoschisis Knockout (Rsl-/y) Mouse Retina and Modification by rAAV-Rs1 Gene Delivery", Investigatiove Phthalmology & Visual Science, vol. 49, No. 8, Mar. 3, 2008 (Mar. 3, 2008), pp. 3677-3686.

Wang et al. "Rapid and highly efficient transduction by double-stranded adeno-associated virus vectors in vitro and in vivo," Gene Therapy, 2003, vol. 10, pp. 2105-2111.

Wu, Zhijian, et al., "Intravitreal Administration of an AAV8 Retinoschisin Vector to the Rs1-K0 Mouse Results in Cell Type-Specific Gene Expression and Rescue of the Disease Phenotype", Molecular Therapy May 2009, vol. 17, No. suppl 1, May 2009 (2009-85), p. s288, XP8827239.

Zeng, Y., "RS-1 Gene Delivery to an Adult Rs1h Knockout Mouse Model Restores ERG b-Wave with Reversal of the Electronegative Waveform of X-Linked Retinoschisis," Investigative Ephthalmology & Visual Science, vol. 45, No. 9, Sep. 2004 (Sep. 2004), pp. 3279-3328.

International Search Report and Written Opinion for International (PCT) Patent Application No. PCT/US14/16389, dated Jun. 4, 2014 24 pages.

International Preliminary Report on Patentability for International (PCT) Patent Application No. PCT/US2014/016389, dated Aug. 27, 2015 18 pages.

Official Action for Australia Patent Application No. 2014216160, dated Mar. 21, 2016 6 pages.

Official Action for Canada Patent Application No. 2,900,231, dated Aug. 19, 2016 6 pages.

Official Action for Canada Patent Application No. 2,900,231, dated Aug. 17, 2017 4 pages.

Official Action for European Patent Application No. 14708176.4, dated Apr. 13, 2017 8 pages.

English Translation of Official Action for Japan Patent Application No. 2015-558144, dated Aug. 23, 2016 5 pages.

English Translation of Official Action for Japan patent Application No. 2015-558144, dated Jun. 6, 2017 5 pages.

Official Action for U.S. Appl. No. 14/766,842, dated Jan. 5, 2017 8 pages Restriction Requirement.

Official Action for U.S. Appl. No. 14/766,842, dated Jun. 2, 2017 13 pages.

Notice of Allowance for U.S. Appl. No. 14/766,842, dated Sep. 18, 2017 8 pages.

Official Action for U.S. Pat. No. 2,900,231, dated Mar. 27, 2018 3 pages.

Weitzman et al. "Adeno-Associated Virus Biology," Methods in Molecular Biology, 2011, vol. 807, pp. 1-23.

Decision to Grant with English Translation for Japan Patent Application No. 2015-558144, dated Nov. 6, 2018 6 pages.

Notice of Allowance for Canada Patent Application No. 2,900,231, dated Mar. 8, 2019 1 page.

\* cited by examiner

SEQUENCE LISTING

<160> NUMBER OF SEQ ID NOS: 16

<210> SEQ ID NO 1
<211> LENGTH: 675
<212> TYPE: DNA
<213> ORGANISM: Homo sapien

<400> SEQUENCE: 1

```
atgtcacgca agatagaagg cttttttgtta ttacttctct ttggctatga agccacattg      60
ggattatcgt ctaccgagga tgaaggcgag gaccccctggt accaaaaagc atgcaagtgc     120
gattgccaag gaggacccaa tgctctgtgg tctgcaggtg ccacctcctt ggactgtata     180
ccagaatgcc catatcacaa gcctctgggt ttcgagtcag gggaggtcac accggaccag     240
atcacctgct ctaacccgga gcagtatgtg ggctggtatt cttcgtggac tgcaaacaag     300
gcccggctca cagtcaagg ctttgggtgt gcctggctct ccaagttcca ggacagtagc     360
cagtggttac agatagatct gaaggagatc aaagtgattt cagggatcct cacccagggg     420
cgctgtgaca tcgatgagtg gatgaccaag tacagcgtgc agtacaggac cgatgagcgc     480
ctgaactgga tttactacaa ggaccagact ggaaacaacc gggtcttcta tggcaactcg     540
gaccgcacct ccacggttca gaacctgctg cggccccca tcatctcccg cttcatccgc     600
ctcatcccgc tgggctggca cgtccgcatt gccatccgga tggagctgct ggagtgcgtc     660
agcaagtgtg cctga                                                      675
```

<210> SEQ ID NO 2
<211> LENGTH: 224
<212> TYPE: PRT
<213> ORGANISM: Homo sapien

<400> SEQUENCE: 2

```
Met Ser Arg Lys Ile Glu Gly Phe Leu Leu Leu Leu Phe Gly Tyr
1               5                   10                  15

Glu Ala Thr Leu Gly Leu Ser Ser Thr Glu Asp Glu Gly Glu Asp Pro
                20                  25                  30

Trp Tyr Gln Lys Ala Cys Lys Cys Asp Cys Gln Gly Gly Pro Asn Ala
            35                  40                  45

Leu Trp Ser Ala Gly Ala Thr Ser Leu Asp Cys Ile Pro Glu Cys Pro
    50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
```

```
              195                 200                 205
Arg Ile Ala Ile Arg Met Glu Leu Leu Glu Cys Val Ser Lys Cys Ala
    210                 215                 220

<210> SEQ ID NO 3
<211> LENGTH: 675
<212> TYPE: DNA
<213> ORGANISM: Homo sapien

<400> SEQUENCE: 3
tcaggcacac ttgctgacgc actccagcag ctccatccgg atggcaatgc ggacgtgcca     60
gcccagcggg atgaggcgga tgaagcggga gatgatgggg ggccgcagca ggttctgaac    120
cgtggaggtg cggtccgagt tgccatagaa gacccggttg tttccagtct ggtccttgta    180
gtaaatccag ttcaggcgct catcggtcct gtactgcacg ctgtacttgg tcatccactc    240
atcgatgtca cagcgcccct gggtgaggat ccctgaaatc actttgatct ccttcagatc    300
tatctgtaac cactggctac tgtcctgaa  cttggagagc caggcacacc caaagccttg    360
actgttgagc cgggccttgt ttgcagtcca cgaagaatac cagcccacat actgctccgg    420
gttagagcag gtgatctggt ccggtgtgac ctcccctgac tcgaaaccca gaggcttgtg    480
atatgggcat tctggtatac agtccaagga ggtggcacct gcagaccaca gagcattggg    540
tcctccttgg caatcgcact tgcatgcttt ttggtaccag gggtcctcgc cttcatcctc    600
ggtagacgat aatcccaatg tggcttcata gccaagaga  agtaataaca aaaagccttc    660
tatcttgcgt gacat                                                     675

<210> SEQ ID NO 4
<211> LENGTH: 606
<212> TYPE: DNA
<213> ORGANISM: Homo sapien

<400> SEQUENCE: 4
tctaccgagg atgaaggcga ggaccctgg  taccaaaaag catgcaagtg cgattgccaa     60
ggaggaccca atgctctgtg gtctgcaggt gccacctcct tggactgtat accagaatgc    120
ccatatcaca agcctctggg tttcgagtca ggggaggtca caccggacca gatcacctgc    180
tctaacccgg agcagtatgt gggctggtat tcttcgtgga ctgcaaacaa ggcccggctc    240
aacagtcaag gctttgggtg tgcctggctc tccaagttcc aggacagtag ccagtggtta    300
cagatagatc tgaaggagat caaagtgatt tcagggatcc tcacccaggg gcgctgtgac    360
atcgatgagt ggatgaccaa gtacagcgtg cagtacagga ccgatgagcg cctgaactgg    420
atttactaca aggaccagac tggaaacaac cgggtcttct atggcaactc ggaccgcacc    480
tccacggttc agaacctgct gcggccccc  atcatctccc gcttcatccg cctcatcccg    540
ctgggctggc acgtccgcat tgccatccgg atggagctgc tggagtgcgt cagcaagtgt    600
gcctga                                                               606

<210> SEQ ID NO 5
<211> LENGTH: 201
<212> TYPE: PRT
<213> ORGANISM: Homo sapien

<400> SEQUENCE: 5

Ser Thr Glu Asp Glu Gly Glu Asp Pro Trp Tyr Gln Lys Ala Cys Lys
1               5                   10                  15

Cys Asp Cys Gln Gly Gly Pro Asn Ala Leu Trp Ser Ala Gly Ala Thr
```

```
                  20                  25                  30
Ser Leu Asp Cys Ile Pro Glu Cys Pro Tyr His Lys Pro Leu Gly Phe
            35                  40                  45

Glu Ser Gly Glu Val Thr Pro Asp Gln Ile Thr Cys Ser Asn Pro Glu
    50                  55                  60

Gln Tyr Val Gly Trp Tyr Ser Ser Trp Thr Ala Asn Lys Ala Arg Leu
65                  70                  75                  80

Asn Ser Gln Gly Phe Gly Cys Ala Trp Leu Ser Lys Phe Gln Asp Ser
                85                  90                  95

Ser Gln Trp Leu Gln Ile Asp Leu Lys Glu Ile Lys Val Ile Ser Gly
            100                 105                 110

Ile Leu Thr Gln Gly Arg Cys Asp Ile Asp Glu Trp Met Thr Lys Tyr
        115                 120                 125

Ser Val Gln Tyr Arg Thr Asp Glu Arg Leu Asn Trp Ile Tyr Tyr Lys
    130                 135                 140

Asp Gln Thr Gly Asn Asn Arg Val Phe Tyr Gly Asn Ser Asp Arg Thr
145                 150                 155                 160

Ser Thr Val Gln Asn Leu Leu Arg Pro Pro Ile Ile Ser Arg Phe Ile
                165                 170                 175

Arg Leu Ile Pro Leu Gly Trp His Val Arg Ile Ala Ile Arg Met Glu
            180                 185                 190

Leu Leu Glu Cys Val Ser Lys Cys Ala
        195                 200

<210> SEQ ID NO 6
<211> LENGTH: 606
<212> TYPE: DNA
<213> ORGANISM: Homo sapien

<400> SEQUENCE: 6
tcaggcacac ttgctgacgc actccagcag ctccatccgg atggcaatgc ggacgtgcca       60
gcccagcggg atgaggcgga tgaagcggga gatgatgggg ggccgcagca ggttctgaac      120
cgtggaggtg cggtccgagt tgccatagaa gacccggttg tttccagtct ggtccttgta      180
gtaaatccag ttcaggcgct catcggtcct gtactgcacg ctgtacttgg tcatccactc      240
atcgatgtca gcgcccct gggtgaggat ccctgaaatc actttgatct ccttcagatc        300
tatctgtaac cactggctac tgtcctggaa cttggagagc caggcacacc caaagccttg      360
actgttgagc cgggccttgt ttgcagtcca cgaagaatac cagcccacat actgctccgg      420
gttagagcag gtgatctggt ccggtgtgac ctcccctgac tcgaaaccca gaggcttgtg      480
atatgggcat tctggtatac agtccaagga ggtggcacct gcagaccaca gagcattggg      540
tcctccttgg caatcgcact tgcatgcttt ttggtaccag ggtcctcgc cttcatcctc       600 ggtaga                                                                606

<210> SEQ ID NO 7
<211> LENGTH: 489
<212> TYPE: DNA
<213> ORGANISM: Homo sapien

<400> SEQUENCE: 7
tgcccatatc acaagcctct gggtttcgag tcaggggagg tcacaccgga ccagatcacc       60
tgctctaacc cggagcagta tgtgggctgg tattcttcgt ggactgcaaa caaggcccgg      120
ctcaacagtc aaggctttgg gtgtgcctgg ctctccaagt tccaggacag tagccagtgg      180
```

```
ttacagatag atctgaagga gatcaaagtg atttcaggga tcctcaccca ggggcgctgt    240
gacatcgatg agtggatgac caagtacagc gtgcagtaca ggaccgatga gcgcctgaac    300
tggatttact acaaggacca gactggaaac aaccgggtct tctatggcaa ctcggaccgc    360
acctccacgg ttcagaacct gctgcggccc cccatcatct cccgcttcat ccgcctcatc    420
ccgctgggct ggcacgtccg cattgccatc cggatggagc tgctggagtg cgtcagcaag    480
tgtgcctga                                                            489
```

```
<210> SEQ ID NO 8
<211> LENGTH: 162
<212> TYPE: PRT
<213> ORGANISM: Homo sapien

<400> SEQUENCE: 8

Cys Pro Tyr His Lys Pro Leu Gly Phe Glu Ser Gly Glu Val Thr Pro
1               5                   10                  15

Asp Gln Ile Thr Cys Ser Asn Pro Glu Gln Tyr Val Gly Trp Tyr Ser
            20                  25                  30

Ser Trp Thr Ala Asn Lys Ala Arg Leu Asn Ser Gln Gly Phe Gly Cys
        35                  40                  45

Ala Trp Leu Ser Lys Phe Gln Asp Ser Ser Gln Trp Leu Gln Ile Asp
    50                  55                  60

Leu Lys Glu Ile Lys Val Ile Ser Gly Ile Leu Thr Gln Gly Arg Cys
65                  70                  75                  80

Asp Ile Asp Glu Trp Met Thr Lys Tyr Ser Val Gln Tyr Arg Thr Asp
                85                  90                  95

Glu Arg Leu Asn Trp Ile Tyr Tyr Lys Asp Gln Thr Gly Asn Asn Arg
            100                 105                 110

Val Phe Tyr Gly Asn Ser Asp Arg Thr Ser Thr Val Gln Asn Leu Leu
        115                 120                 125

Arg Pro Pro Ile Ile Ser Arg Phe Ile Arg Leu Ile Pro Leu Gly Trp
    130                 135                 140

His Val Arg Ile Ala Ile Arg Met Glu Leu Leu Glu Cys Val Ser Lys
145                 150                 155                 160

Cys Ala
```

```
<210> SEQ ID NO 9
<211> LENGTH: 1071
<212> TYPE: DNA
<213> ORGANISM: Artificial Sequence
<220> FEATURE:
<223> OTHER INFORMATION: Human retinoschisin promoter construct

<400> SEQUENCE: 9
gcggccgcac caccaaattt agcatttcc tgagtgaata ggtgtgcaca tgatgcctag     60
ttgctttcaa agaggggaat ccatgacatt tcatacaat tcgagaatgt tagtgcttat    120
gtggcaggaa attgttcaag gtcacccct aaaaaatgat ggcgaagaaa ggacgaaaac    180
ctgagacttc tggttgtagt tctctcctc cattgcttcc cttacattaa gatagaatga    240
acagtatggt cgacggccca ggcttcccag cagggctaag gatatgcaag gagtgcattc    300
atccggaggt gttggcagca tcccagcccc accccattct catcgtaaat caggctcact    360
tccattggct gcatacggtg gagtgatgtg accatatgtc acttgagcat tacacaaatc    420
ctaatgagct aaaaatatgt tgttttagc taattgacct ctttggcctt cataaagcag    480
ttggtaaaca tcctcagata atgatttcca aagaggtcga ccgaaaagta tcttcctcgc    540
```

```
gaactgaatc tcagttgatg ctagtatctt ccatgagact tccttgttga ggcaggtaac    600
tctgtgggtt aacttgatgg ggctcagcca aagacctaag aactaaatgg attaagatgc    660
ttaatgaggc cagggctcaa cttaatcccc tgctcctggg ccagctctcc agttcagtaa    720
ggtagagctt tggccgagga cgaggggaag atgtcacgca agatagaagg cttttttgtta   780 ttacttctct ttggctatga aggtatgtgc tattcaacca ttgacattca ttgcatactt    840
aatacataat ttaattaata tcgttgataa ataggaatat agcctgaata atataaatat    900
tattaattag caacacgtta attaactaac atgtgttatt aatgaacaac agttgtcttt    960
gtgtggatgg ctttccagtt ctgtgaggag ccttctaaag ttcaaaggat gcttaaaatc   1020
caacagaaaa caggatgggt ctcagaaatc tataaaatag ccagcgatcg c            1071

<210> SEQ ID NO 10
<211> LENGTH: 245
<212> TYPE: DNA
<213> ORGANISM: Homo sapien

<400> SEQUENCE: 10
aagatagaag gcttttttgtt attacttctc tttggctatg aagccacatt gggattatcg     60
tctaccgagg atgaaggcga ggacccctgg taccaaaaag catgcaagtg cgattgccaa    120
ggaggaccca atgctctgtg gtctgcaggt gccacctcct tggactgtat accagaatgc    180
ccatatcaca agcctctggg tttcgagtca ggggaggtca caccggacca gatcacctgc    240
tctaa                                                                245

<210> SEQ ID NO 11
<211> LENGTH: 229
<212> TYPE: DNA
<213> ORGANISM: Artificial Sequence
<220> FEATURE:
<223> OTHER INFORMATION: Human retinoschisin promoter sequence
      (nucleotides 522-750 of SEQ ID NO:9)

<400> SEQUENCE: 11
cgaaaagtat cttcctcgcg aactgaatct cagttgatgc tagtatcttc catgagactt     60
ccttgttgag gcaggtaact ctgtgggtta acttgatggg gctcagccaa agacctaaga    120
actaaatgga ttaagatgct taatgaggcc agggctcaac ttaatcccct gctcctgggc    180
cagctctcca gttcagtaag gtagagcttt ggccgaggac gaggggaag                229

<210> SEQ ID NO 12
<211> LENGTH: 261
<212> TYPE: DNA
<213> ORGANISM: Homo sapien

<400> SEQUENCE: 12
ggcccaggct tcccagcagg gctaaggata tgcaaggagt gcattcatcc ggaggtgttg     60
gcagcatccc agccccaccc cattctcatc gtaaatcagg ctcacttcca ttggctgcat    120
acggtggagt gatgtgacca tatgtcactt gagcattaca caaatcctaa tgagctaaaa    180
atatgtttgt tttagctaat tgacctcttt ggccttcata aagcagttgg taaacatcct    240
cagataatga tttccaaaga g                                              261

<210> SEQ ID NO 13
<211> LENGTH: 2217
<212> TYPE: DNA
<213> ORGANISM: Adeno-associated virus
```

<400> SEQUENCE: 13

```
atggctgccg atggttatct tccagattgg ctcgaggaca acctctctga gggcattcgc    60
gagtggtggg cgctgaaacc tggagccccg aagcccaaag ccaaccagca aaagcaggac   120
gacggccggg gtctggtgct tcctggctac aagtacctcg acccttcaa cggactcgac    180
aaggggagc ccgtcaacgc ggcggacgca gcggccctcg agcacgacaa ggcctacgac    240
cagcagctgc aggcgggtga caatccgtac ctgcggtata accacgccga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaga gaccggtaga gccatcaccc cagcgttctc cagactcctc tacgggcatc   480
ggcaagaaag ccaacagcc cgccagaaaa agactcaatt ttggtcagac tggcgactca   540
gagtcagttc cagaccctca acctctcgga gaacctccag cagcgccctc tggtgtggga   600
cctaatacaa tggctgcagg cggtggcgca ccaatggcag acaataacga aggcgccgac   660
ggagtgggta gttcctcggg aaattggcat tgcgattcca catggctggg cgacagagtc   720
atcaccacca gcacccgaac ctgggccctg cccacctaca caaccaccct ctacaagcaa   780
atctccaacg ggacatcggg aggagccacc aacgacaaca cctacttcgg ctacagcacc   840
ccctgggggt attttgactt taacagattc cactgccact tttcaccacg tgactggcag   900
cgactcatca acaacaactg gggattccgg cccaagagac tcagcttcaa gctcttcaac   960
atccaggtca aggaggtcac gcagaatgaa ggcaccaaga ccatcgccaa taacctcacc  1020
agcaccatcc aggtgtttac ggactcggag taccagctgc cgtacgttct cggctctgcc  1080
caccagggct gcctgcctcc gttcccggcg gacgtgttca tgattcccca gtacggctac  1140
ctaacactca acaacggtag tcaggccgtg ggacgctcct ccttctactg cctggaatac  1200
tttccttcgc agatgctgag aaccggcaac aacttccagt ttacttacac cttcgaggac  1260
gtgcctttcc acagcagcta cgcccacagc cagagcttgg accggctgat gaatcctctg  1320
attgaccagt acctgtacta cttgtctcgg actcaaacaa caggaggcac ggcaaatacg  1380
cagactctgg gcttcagcca aggtgggcct aatacaatgg ccaatcaggc aaagaactgg  1440
ctgccaggac cctgttaccg ccaacaacgc gtctcaacga caaccgggca aaacaacaat  1500
agcaactttg cctggactgc tgggaccaaa taccatctga tggaagaaa ttcattggct  1560
aatcctggca tcgctatggc aacacacaaa gacgacgagg agcgttttt tcccagtaac  1620
gggatcctga tttttggcaa acaaaatgct gccagagaca tgcggatta cagcgatgtc  1680
atgctcacca gcgaggaaga aatcaaaacc actaaccctg tggctacaga ggaatacggt  1740
atcgtggcag ataacttgca gcagcaaaac acggctcctc aaattggaac tgtcaacagc  1800
caggggccct acccggtat ggtctggcag aaccgggacg tgtacctgca gggtcccatc  1860
tgggccaaga ttcctcacac ggacggcaac ttccaccccgt ctccgctgat gggcggcttt  1920
ggcctgaaac atcctccgcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctgtaa     2217
```

<210> SEQ ID NO 14

<211> LENGTH: 738
<212> TYPE: PRT
<213> ORGANISM: Adeno-associated virus

<400> SEQUENCE: 14

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
```

```
            385                 390                 395                 400
        Phe Pro Ser Gln Met Leu Arg Thr Gly Asn Asn Phe Gln Phe Thr Tyr
                        405                 410                 415
        Thr Phe Glu Asp Val Pro Phe His Ser Ser Tyr Ala His Ser Gln Ser
                    420                 425                 430
        Leu Asp Arg Leu Met Asn Pro Leu Ile Asp Gln Tyr Leu Tyr Tyr Leu
                435                 440                 445
        Ser Arg Thr Gln Thr Thr Gly Gly Thr Ala Asn Thr Gln Thr Leu Gly
            450                 455                 460
        Phe Ser Gln Gly Gly Pro Asn Thr Met Ala Asn Gln Ala Lys Asn Trp
        465                 470                 475                 480
        Leu Pro Gly Pro Cys Tyr Arg Gln Gln Arg Val Ser Thr Thr Thr Gly
                        485                 490                 495
        Gln Asn Asn Asn Ser Asn Phe Ala Trp Thr Ala Gly Thr Lys Tyr His
                        500                 505                 510
        Leu Asn Gly Arg Asn Ser Leu Ala Asn Pro Gly Ile Ala Met Ala Thr
                    515                 520                 525
        His Lys Asp Asp Glu Glu Arg Phe Phe Pro Ser Asn Gly Ile Leu Ile
                530                 535                 540
        Phe Gly Lys Gln Asn Ala Ala Arg Asp Asn Ala Asp Tyr Ser Asp Val
        545                 550                 555                 560
        Met Leu Thr Ser Glu Glu Glu Ile Lys Thr Thr Asn Pro Val Ala Thr
                        565                 570                 575
        Glu Glu Tyr Gly Ile Val Ala Asp Asn Leu Gln Gln Gln Asn Thr Ala
                    580                 585                 590
        Pro Gln Ile Gly Thr Val Asn Ser Gln Gly Ala Leu Pro Gly Met Val
                595                 600                 605
        Trp Gln Asn Arg Asp Val Tyr Leu Gln Gly Pro Ile Trp Ala Lys Ile
            610                 615                 620
        Pro His Thr Asp Gly Asn Phe His Pro Ser Pro Leu Met Gly Gly Phe
        625                 630                 635                 640
        Gly Leu Lys His Pro Pro Pro Gln Ile Leu Ile Lys Asn Thr Pro Val
                        645                 650                 655
        Pro Ala Asp Pro Pro Thr Thr Phe Asn Gln Ser Lys Leu Asn Ser Phe
                    660                 665                 670
        Ile Thr Gln Tyr Ser Thr Gly Gln Val Ser Val Glu Ile Glu Trp Glu
                675                 680                 685
        Leu Gln Lys Glu Asn Ser Lys Arg Trp Asn Pro Glu Ile Gln Tyr Thr
            690                 695                 700
        Ser Asn Tyr Tyr Lys Ser Thr Ser Val Asp Phe Ala Val Asn Thr Glu
        705                 710                 715                 720
        Gly Val Tyr Ser Glu Pro Arg Pro Ile Gly Thr Arg Tyr Leu Thr Arg
                        725                 730                 735
        Asn Leu

<210> SEQ ID NO 15
<211> LENGTH: 2217
<212> TYPE: DNA
<213> ORGANISM: Homo sapien

<400> SEQUENCE: 15
ttacagatta cgggtgaggt aacgggtgcc aatgggcgg ggttcagagt acacgccttc      60
tgtattaaca gcaaagtcca cacttgtaga tttgtagtag ttggaggtgt actggatctc    120
```

```
ggggttccag cgcttgctgt tttccttctg cagctcccat tcaatttcca cgctgacctg      180
tccggtgctg tattgcgtga tgaaagagtt cagctttgac tggttgaagg tggtcggagg      240
atccgcaggt acaggcgtgt tcttgatcag gatctgaggc ggaggatgtt tcaggccaaa      300
gccgcccatc agcggagacg ggtggaagtt gccgtccgtg tgaggaatct tggcccagat      360
gggaccctgc aggtacacgt cccggttctg ccagaccata ccgggtaagg cccctggct       420 gttgacagtt ccaatttgag gagccgtgtt ttgctgctgc aagttatctg ccacgatacc      480
gtattcctct gtagccacag ggttagtggt tttgatttct tcctcgctgg tgagcatgac      540
atcgctgtaa tccgcattgt ctctggcagc attttgtttg ccaaaaatca ggatcccgtt      600
actgggaaaa aaacgctcct cgtcgtcttt gtgtgttgcc atagcgatgc caggattagc      660
caatgaattt cttccattca gatggtattt ggtcccagca gtccaggcaa agttgctatt      720
gttgttttgc ccggttgtcg ttgagacgcg ttgttggcgg taacagggtc ctggcagcca      780
gttctttgcc tgattggcca ttgtattagg cccaccttgg ctgaagccca gagtctgcgt      840
atttgccgtg cctcctgttg tttgagtccg agacaagtag tacaggtact ggtcaatcag      900
aggattcatc agccggtcca agctctggct gtgggcgtag ctgctgtgga aaggcacgtc      960
ctcgaaggtg taagtaaact ggaagttgtt gccggttctc agcatctgcg aaggaaagta      1020
ttccaggcag tagaaggagg agcgtcccac ggcctgacta ccgttgttga gtgttaggta      1080
gccgtactgg ggaatcatga acacgtccgc cgggaacgga ggcaggcagc cctggtgggc      1140
agagccgaga acgtacggca gctggtactc cgagtccgta aacacctgga tggtgctggt      1200
gaggttattg gcgatggtct tggtgccttc attctgcgtg acctccttga cctggatgtt      1260
gaagagcttg aagctgagtc tcttgggccg gaatcccag ttgttgttga tgagtcgctg      1320
ccagtcacgt ggtgaaaagt ggcagtggaa tctgttaaag tcaaaatacc cccagggggt      1380
gctgtagccg aagtaggtgt tgtcgttggt ggctcctccc gatgtcccgt tggagatttg      1440
cttgtagagg tggttgttgt aggtgggcag ggcccaggtt cgggtgctgg tggtgatgac      1500
tctgtcgccc agccatgtgg aatcgcaatg ccaatttccc gaggaactac ccactccgtc      1560
ggcgccttcg ttattgtctg ccattggtgc gccaccgcct gcagccattg tattaggtcc      1620
cacaccagag ggcgctgctg gaggttctcc gagaggttga gggtctggaa ctgactctga      1680
gtcgccagtc tgaccaaaat tgagtctttt tctggcgggc tgttggcctt tcttgccgat      1740
gcccgtagag gagtctggag aacgctgggg tgatggctct accggtctct tctttccagg      1800
agccgtctta gcgccttcct caaccagacc gagaggttcg agaacccgct tcttggcctg      1860
gaagactgct cgcccgaggt tgcccccaaa agacgtatct tcttgcagac gctcctgaaa      1920
ctcggcgtcg gcgtggttat accgcaggta cggattgtca cccgcctgca gctgctggtc      1980
gtaggccttg tcgtgctcga gggccgctgc gtccgccgcg ttgacgggct ccccccttgtc     2040 gagtccgttg aagggtccga ggtacttgta gccaggaagc accagacccc ggccgtcgtc     2100
ctgcttttgc tggttggctt tgggcttcgg ggctccaggt ttcagcgccc accactcgcg     2160
aatgccctca gagaggttgt cctcgagcca atctggaaga taaccatcgg cagccat       2217
```

<210> SEQ ID NO 16
<211> LENGTH: 9504
<212> TYPE: DNA
<213> ORGANISM: Artificial Sequence
<220> FEATURE:
<223> OTHER INFORMATION: Full length sequence of pV scRS/IRBP hRS vector

<400> SEQUENCE: 16

```
agttaattaa cacagctgcg cgctcgctcg ctcactgagg ccgcccgggc aaagcccggg    60
cgtcgggcga cctttggtcg cccggcctca gtgagcgagc gagcgcgcag agagggagtg   120 gggggatcc actagttcta gagcggccgc accaccaaat ttagcatttt cctgagtgaa   180
taggtgtgca catgatgcct agttgctttc aaagagggga atccatgaca ttttcataca   240
attcgagaat gttagtgctt atgtggcagg aaattgttca aggtcacccc ctaaaaaatg   300
atggcgaaga aggacgaaa acctgagact tctggttgta gttctctccc tccattgctt   360
cccttacatt aagatagaat gaacagtatg gtcgacggcc caggcttccc agcagggcta   420
aggatatgca aggagtgcat tcatccggag gtgttggcag catcccagcc ccaccccatt   480
ctcatcgtaa atcaggctca cttccattgg ctgcatacgg tggagtgatg tgaccatatg   540
tcacttgagc attacacaaa tcctaatgag ctaaaaatat gtttgtttta gctaattgac   600
ctctttggcc ttcataaagc agttggtaaa catcctcaga taatgatttc caagagggtc   660
gaccgaaaag tatcttcctc gcgaactgaa tctcagttga tgctagtatc ttccatgaga   720
cttccttgtt gaggcaggta actctgtggg ttaacttgat ggggctcagc caaagaccta   780
agaactaaat ggattaagat gcttaatgag gccagggctc aacttaatcc cctgctcctg   840
ggccagctct ccagttcagt aaggtagagc tttggccgag gacgagggga agatgtcacg   900
caagatagaa ggcttttttgt tattacttct ctttggctat gaaggtatgt gctattcaac   960
cattgacatt cattgcatac ttaatacata atttaattaa tatcgttgat aaataggaat  1020
atagcctgaa taatataaat attattaatt agcaacacgt taattaacta acatgtgtta  1080
ttaatgaaca acagttgtct ttgtgtggat ggctttccag ttctgtgagg agccttctaa  1140
agttcaaagg atgcttaaaa tccaacagaa aacaggatgg gtctcagaaa tctataaaat  1200
agccagcgat cgcgatttct ctttcattaa ttagattttt tctgtctcat cctttgtgctt  1260 tagccacatt gggattatcg tctaccgagg atgaaggcga ggaccctgg taccaaaaag  1320 catgcaagtg cgattgccaa ggaggaccca atgctctgtg gtctgcaggt gccacctcct  1380
tggactgtat accagaatgc ccatatcaca agcctctggg tttcgagtca ggggaggtca  1440
caccggacca gatcacctgc tctaacccgg agcagtatgg gggctggtat tcttcgtgga  1500
ctgcaaacaa ggcccggctc aacagtcaag gctttgggtg tgcctggctc tccaagttcc  1560
aggacagtag ccagtggtta cagatagatc tgaaggagat caaagtgatt tcagggatcc  1620
tcacccaggg gcgctgtgac atcgatgagt ggatgaccaa gtacagcgtg cagtacagga  1680
ccgatgagcg cctgaactgg atttactaca aggaccagac tggaaacaac cgggtcttct  1740
atggcaactc ggaccgcacc tccacggttc agaacctgct gcggccccc atcatctccc  1800 gcttcatccg cctcatcccg ctgggctggc acgtccgcat tgccatccgg atggagctgc  1860
tggagtgcgt cagcaagtgt gcctgactcg agagatctaa tctcgctttc ttgctgtcca  1920
atttctatta aaggttcctt tgttccctaa gtccaactac taaactgggg gatattatga  1980
agggccttga gcatctggat tctgcctaat aaaaaacatt tattttcatt gcaatgatgt  2040
atttaaatta tttctgaata ttttactaaa aagggaatgt gggaggtcag tgcatttaaa  2100
acataaagaa agtagggcgc gccaggaacc cctagtgatg gagttggcca ctccctctct  2160
gcgcgctcgc tcgctcactg aggccgcccg gcaaagccc gggcgtcggg cgacctttgg  2220
tcgcccggcc tcagtgagcg agcgagcgcg cagagaggga gtggccaagg ccggccaagc  2280
ttggcgtaat catggtcata gctgtttcct gtgtgaaatt gttatccgct cacaattcca  2340
```

```
cacaacatac gagccggaag cataaagtgt aaagcctggg gtgcctaatg agtgagctaa    2400
ctcacattaa ttgcgttgcg ctcactgccc gctttccagt cgggaaacct gtcgtgccag    2460
ctgcattaat gaatcggcca acgcgcgggg agaggcggtt tgcgtattgg gcgctcttcc    2520
gctgtcctgc aggacatgtg agcaaaaggc cagcaaaagg ccaggaaccg taaaaaggcc    2580
gcgttgctgg cgtttttcca taggctccgc cccctgacg agcatcacaa aaatcgacgc     2640
tcaagtcaga ggtggcgaaa cccgacagga ctataaagat accaggcgtt ccccctggaa    2700
agctccctcg tgcgctctcc tgttccgacc ctgccgctta ccggatacct gtccgccttt    2760
ctcccttcgg gaagcgtggc gctttctcat agctcacgct gtaggtatct cagttcggtg    2820
taggtcgttc gctccaagct gggctgtgtg cacgaacccc ccgttcagcc cgaccgctgc    2880
gccttatccg gtaactatcg tcttgagtcc aacccggtaa gacacgactt atcgccactg    2940
gcagcagcca ctggtaacag gattagcaga gcgaggtatg taggcggtgc tacagagttc    3000
ttgaagtggt ggcctaacta cggctacact agaaggacag tatttggtat ctgcgctctg    3060
ctgaagccag ttaccttcgg aaaaagagtt ggtagctctt gatccggcaa acaaaccacc    3120
gctggtagcg gtggtttttt tgtttgcaag cagcagatta cgcgcagaaa aaaaggatct    3180
caagaagatc ctttgatctt ttctacgggg tctgacgctc agtggaacga aaactcacgt    3240
taagggattt tggtcatgag attatcaaaa aggatcttca cctagatcct tttaaattaa    3300
aaatgaagtt ttaaatcaat ctaaagtata tatgagtaaa cttggtctga cagttaccaa    3360
tgcttaatca gtgaggcacc tatctcagcg atctgtctat ttcgttcatc catagttgcc    3420
tgactccccg tcgtgtagat aactacgata cgggagggct taccatctgg ccccagtgct    3480
gcaatgatac cgcgagaccc acgctcaccg gctccagatt tatcagcaat aaaccagcca    3540
gccgaagggg ccgagcgcag aagtggtcct gcaactttat ccgcctccat ccagtctatt    3600
aattgttgcc gggaagctag agtaagtagt tcgccagtta atagtttgcg caacgttgtt    3660
gccattgcta caggcatcgt ggtgtcacgc tcgtcgtttg gtatggcttc attcagctcc    3720
ggttcccaac gatcaaggcg agttacatga tcccccatgt tgtgcaaaaa agcggttagc    3780
tccttcggtc ctccgatcgt tgtcagaagt aagttggccg cagtgttatc actcatggtt    3840
atggcagcac tgcataattc tcttactgtc atgccatccg taagatgctt ttctgtgact    3900
ggtgagtact caaccaagtc attctgagaa tagtgtatgc ggcgaccgag ttgctcttgc    3960
ccggcgtcaa tacgggataa taccgcgcca catagcagaa ctttaaaagt gctcatcatt    4020
ggaaaacgtt cttcggggcg aaaactctca aggatcttac cgctgttgag atccagttcg    4080
atgtaaccca ctcgtgcacc caactgatct tcagcatctt ttactttcac cagcgtttct    4140
gggtgagcaa aaacaggaag gcaaaatgcc gcaaaaaagg gaataagggc gacacggaaa    4200
tgttgaatac tcatactctt ccttttttcaa tattattgaa gcatttatca gggttattgt    4260
ctcatgagcg gatacatatt tgaatgtatt tagaaaaata aacaaatagg ggttccgcgc    4320
acatttcccc gaaaagtgcc acctgacgtc taagaaacca ttattatcat gacattaacc    4380
tataaaaata ggcgtatcac gaggcccttt cgtctcgcgc gtttcggtga tgacggtgaa    4440
aacctctgac acatgcagct cccggagacg gtcacagctt gtctgtaagc ggatgccggg    4500
agcagacaag cccgtcaggg cgcgtcagcg ggtgttggcg ggtgtcgggg ctggcttaac    4560
tatgcggcat cagagcagat tgtactgaga gtgcaccata aaattgtaaa cgttaatatt    4620
ttgttaaaat tcgcgttaaa tttttgttaa atcagctcat ttttttaacca ataggccgaa    4680 atcggcaaaa tcccttataa atcaaaagaa tagcccgaga taggggttgag tgttgttcca    4740
```

```
gtttggaaca agagtccact attaaagaac gtggactcca acgtcaaagg gcgaaaaacc    4800
gtctatcagg gcgatggccc actacgtgaa ccatcaccca aatcaagttt tttggggtcg    4860
aggtgccgta aagcactaaa tcggaaccct aaagggagcc cccgatttag agcttgacgg    4920
ggaaagccgg cgaacgtggc gagaaaggaa gggaagaaag cgaaaggagc gggcgctagg    4980
gcgctggcaa gtgtagcggt cacgctgcgc gtaaccacca cacccgccgc gcttaatgcg    5040
ccgctacagg gcgcgtacta tggttgcttt gacgtatgcg gtgtgaaata ccgcacagat    5100
gcgtaaggag aaaataccgc atcaggccgt aacctgtcgg atcaccggaa aggacccgta    5160
aagtgataat gattatcatc tacatatcac aacgtgcgtg gaggccatca aaccacgtca    5220
aataatcaat tatgacgcag gtatcgtatt aattgatctg catcaactta acgtaaaaac    5280
aacttcagac aatacaaatc agcgacactg aatacgggga acctcatgt caacgaagaa     5340 cagaacccgc agaacaacaa cccgcaacat ccgctttcct aaccaaatga ttgaacaaat    5400
taacatcgct cttgagcaaa aagggtccgg gaatttctca gcctgggtca ttgaagcctg    5460
ccgtcggaga ctaacgtcag aaaagagagc atatacatca attaaaagtg atgaagaatg    5520
aacatcccgc gttcttccct ccgaacagga cgatattgta aattcactta attacgaggg    5580
cattgcagta attgagttgc agttttacca ctttcctgac agtgacagac tgcgtgttgg    5640
ctctgtcaca gactaaatag tttgaatgat tagcagttat ggtgatcagt caaccaccag    5700 ggataatcc ttcatattat tatcgtgctt caccaacgct gcctcaattg ctctgaatgc     5760
ttccagagac accttatgtt ctatacatgc aattacaaca tcagggtaac tcatagaaat    5820
ggtgctatta agcatatttt ttacacgaat cagatccacg gagggatcat cagcagattg    5880
ttctttattc attttgtcgc tccatgcgct tgctcttcat ctagcggtta aaatattact    5940
tcaaatcttt ctgtatgaag atttgagcac gttggcctta catacatctg tcggttgtat    6000
ttccctccag aatgccagca ggaccgcact ttgttacgca accaatacta ttaagtgaaa    6060
acattcctaa tatttgacat aaatcatcaa caaaacacaa ggaggtcaga ccagattgaa    6120
acgataaaaa cgataatgca aactacgcgc cctcgtatca catggaaggt tttaccaatg    6180
gctcaggttg ccattttaa agaaatattc gatcaagtgc gaaaagattt agactgtgaa     6240 ttgtttatt ctgaactaaa acgtcacaac gtctcacatt atatttacta tctagccaca     6300
gataatattc acatcgtgtt agaaaacgat aacaccgtgt taataaaagg acttaaaaag    6360
gttgtaaatg ttaaattctc aagaaacacg catcttatag aaacgtccta tgataggttg    6420
aaatcaagag aaatcacatt tcagcaatac agggaaaatc ttgctaaagc aggagttttc    6480
cgatgggtta caaatatcca tgaacataaa agatattact ataccctttga taattcatta    6540 ctatttactg agagcattca gaacactaca caaatctttc cacgctaaat cataacgtcc    6600
ggtttcttcc gtgtcagcac cggggcgttg gcataatgca atacgtgtac gcgctaaacc    6660
ctgtgtgcat cgtttttaatt attcccggac actcccgcag agaagttccc cgtcagggct    6720
gtggacatag ttaatccggg aatacaatga cgattcatcg cacctgacat acattaataa    6780
atattaacaa tatgaaattt caactcattg tttagggttt gtttaatttt ctacacatac    6840
gattctgcga acttcaaaaa gcatcgggaa taacaccatg aaaaaaatgc tactcgctac    6900
tgcgctggcc ctgcttatta caggatgtgc tcaacagacg tttactgttc aaaacaaacc    6960
ggcagcagta gcaccaaagg aaaccatcac ccatcatttc ttcgtttctg gaattgggca    7020
gaagaaaact gtcgatgcag ccaaaatttg tggcggcgca gaaaatgttg ttaaaacaga    7080
```

```
aacccagcaa acattcgtaa atggattgct cggtttt att actttaggca tttatactcc   7140
gctggaagcg cgtgtgtatt gctcacaata attgcatgag ttgcccatcg atatgggcaa   7200
ctctatctgc actgctcatt aatatacttc tgggttcctt ccagttgttt ttgcatagtg   7260
atcagcctct ctctgagggt gaaataatcc cgttcagcgg tgtctgccag tcgggggag    7320
gctgcattat ccacgccgga ggcggtggtg gcttcacgca ctgactgaca gactgctttg   7380
atgtgcaacc gacgacgacc agcggcaaca tcatcacgca gagcatcatt ttcagcttta   7440
gcatcagcta actccttcgt gtattttgca tcgagcgcag caacatcacg ctgacgcatc   7500
tgcatgtcag taattgccgc gttcgccagc ttcagttctc tggcattttt gtcgcgctgg   7560
gctttgtagg taatggcgtt atcacggtaa tgattaacag cccatgacag gcagacgatg   7620
atgcagataa ccagagcgga gataatcgcg gtgactctgc tcatacatca atctctctga   7680
ccgttccgcc cgcttctttg aattttgcaa tcaggctgtc agccttatgc tcgaactgac   7740
cataaccagc gcccggcagt gaagcccaga tattgctgca acggtcgatt gcctgacgga   7800
tatcaccacg atcaatcata ggtaaagcgc cacgctcctt aatctgctgc aatgccacag   7860
cgtcctgact tttcggagag aagtctttca ggccaagctg cttgcggtag gcatcccacc   7920
aacgggaaag aagctggtag cgtccggcgc ctgttgattt gagttttggg tttagcgtga   7980
caagtttgcg agggtgatcg gagtaatcag taaatagctc tccgcctaca atgacgtcat   8040
aaccatgatt tctggttttc tgacgtccgt tatcagttcc ctccgaccac gccagcatat   8100
cgaggaacgc cttacgttga ttattgattt ctaccatctt ctactccggc ttttttagca   8160
gcgaagcgtt tgataagcga accaatcgag tcagtaccga tgtagccgat aaacacgctc   8220
gttatataag cgagattgct acttagtccg gcgaagtcga aaggtcacg aatgaaccag    8280
gcgataatgg cgcacatcgt tgcgtcgatt actgttttg taaacgcacc gccattatat    8340
ctgccgcgaa ggtacgccat tgcaaacgca aggattgccc cgatgccttg ttccttttgcc  8400
gcgagaatgg cggccaacag gtcatgtttt tctggcatct tcatgtctta cccccaataa   8460
ggggatttgc tctatttaat taggaataag gtcgattact gatagaacaa atccaggcta   8520
ctgtgtttag taatcagatt tgttcgtgac cgatatgcac gggcaaaacg gcaggaggtt   8580
gttagcgcga cctcctgcca cccgctttca cgaaggtcat gtgtaaaagg ccgcagcgta   8640
actattacta atgaattcag gacagacagt ggctacggct cagtttgggt tgtgctgttg   8700
ctgggcggcg atgacgcctg tacgcatttg gtgatccggt tctgcttccg gtattcgctt   8760
aattcagcac aacggaaaga gcactggcta accaggctcg ccgactcttc acgattatcg   8820
actcaatgct cttacctgtt gtgcagatat aaaaaatccc gaaaccgtta tgcaggctct   8880
aactattacc tgcgaactgt ttcgggattg cattttgcag acctctctgc ctgcgatggt   8940
tggagttcca gacgatacgt cgaagtgacc aactaggcgg aatcggtagt aagcgccgcc   9000
tcttttcatc tcactaccac aacgagcgaa ttaacccatc gttgagtcaa atttacccaa   9060
ttttattcaa taagtcaata tcatgccgtt aatatgttgc catccgtggc aatcatgctg   9120
ctaacgtgtg accgcattca aaatgttgtc tgcgattgac tcttctttgt ggcattgcac   9180
caccagagcg tcatacagcg gcttaacagt gcgtgaccag gtgggttggg taaggtttgg   9240
gattagcatc gtcacagcgc gatatgctgc gcttgctggc atccttgaat agccgacgcc   9300
```

-continued

```
tttgcatctt ccgcactctt tctcgacaac tctcccccac agctctgttt tggcaatatc    9360
aaccgcacgg cctgtaccat ggcaatctct gcatcttgcc cccggcgtcg cggcactacg    9420
gcaataatcc gcataagcga atgttgcgag cacttgcagt acctttgcct tagtatttcc    9480
ttcaagctgc ccctgcagga ctcg                                          9504
```

METHODS AND COMPOSITIONS FOR TREATING GENETICALLY LINKED DISEASES OF THE EYE

CROSS REFERENCE TO RELATED APPLICATION

This application is a continuation-in-part of U.S. patent application Ser. No. 14/766,842, filed on Aug. 10, 2015 (now issued as U.S. Pat. No. 9,873,893), which is a national stage application under 35 U.S.C. 371 and claims the benefit of International Application No. PCT/US2014/016389 having an international filing date of Feb. 14, 2014, which designated the United States, which PCT application claimed the benefit of U.S. Provisional Patent Application Ser. No. 61/765,654 filed Feb. 15, 2013 and U.S. Provisional Patent Application Ser. No. 61/815,636 filed Apr. 24, 2013, the disclosures of each of which are incorporated herein by reference.

SEQUENCE LISTING

The Sequence Listing text file attached hereto, created Jan. 23, 2018 size 38000 bytes, and filed herewith as file name "6137NEI-1-PUS-C1_Sequence_Listing_ST25.txt" is incorporated herein by reference in its entirety.

TECHNICAL FIELD

The invention relates to gene therapy and specifically, expression vectors and therapeutic methods of using such vectors in the treatment of diseases of the eye resulting from failure to produce a specific protein in the eye, or the production of a non-functional protein in the eye.

BACKGROUND OF INVENTION

Several diseases of the eye result from an underlying genetic cause. For example, in some diseases, a mutation in a protein expressed in cells of the eye alters, or abolishes, the proteins activity resulting in a disease state. In other diseases, the cause may be due to failure of eye cells to produce a particular protein. Because these diseases are due to inactivation, or alteration, of a single protein they are particularly amenable to gene transfer-based therapies. Gene therapy for ocular disease has a set of attractive attributes, including a small tissue target and a closed compartment, which thereby requires a low dose. Additionally, the eye is a relatively immune-privileged environment.

One example of an eye disease having a genetic cause is X-linked juvenile retinoschisis (XLRS). XLRS is a neurodevelopmental retinal abnormality that manifests early in life and causes impaired acuity and a propensity to retinal detachment. XLRS is characterized by structural abnormalities in normal lamination of the retinal neuronal and plexiform layers. Clinical examination shows microcysts within the macula, and schisis or internal dissection of the layers of the peripheral retina, (Eksandh L C, Ponjavic V, Ayyagari R, Bingham E L, Hiriyanna K T, Andreasson S, Ehinger B, Sieving P A. 2000. Phenotypic expression of juvenile X-linked retinoschisis in Swedish families with different mutations in the XLRS1 gene. *Arch Ophthalmol* 118: 1098-1104; Prenner J L, Capone A, Jr., Ciaccia S, Takada Y, Sieving P A, Trese M T. 2006. Congenital X-linked retinoschisis classification system. *Retina* 26: S61-64) and this is evident by using ocular coherence tomography (Gerth C, Zawadzki R J, Werner J S, Heon E. Retinal morphological changes of patients with X-linked retinoschisis evaluated by Fourier-domain optical coherence tomography. Arch Ophthalmol. 2008; 126:807-11). Impaired retinal synaptic transmission of neural signals causes loss of dark-adapted absolute visual perception. This is evident on clinical electroretinogram (ERG) testing as a characteristic reduction of the b-wave response (from second-order retinal bipolar cells) relative to the photoreceptor a-wave, which frequently gives rise to an 'electronegative ERG waveform.' The fragile XLRS retina is more prone to disease related complications, such as vitreous hemorrhage and retinal detachment, and the condition worsens with age. The rate of retinal detachment in the XLRS population is considerably higher than in the general population (10 vs 0.01%, respectively), and the postoperative outcome is much worse.

X-linked juvenile retinoschisis is caused by mutations in the gene-encoding retinoschisin, a 224-amino acid secreted protein that is expressed only by the retina and pineal. Human retinoschisin is composed of a 23-amino acid signal sequence, a 39-amino acid Rs1 domain, a 157-amino acid discoidin domain and a 5-amino acid C-terminal segment. Discoidin domain containing proteins are widely distributed in eukaryotes and mediate a variety of functions, including cell adhesion, cell-extracellular matrix interactions, signal transduction, phagocytosis of apoptotic cells, axon guidance, angiogenesis and blood clotting. Many of these proteins are involved in extracellular matrix or cell binding, although some bind ligands such as vascular endothelial growth factor and semaphorin. Retinoschisin is secreted from retinal neurons as a disulfide-linked homo-octameric complex, which adheres to the cell surface, but its function is not well understood. Biochemical activities attributed to retinoschisin are the binding of b-2-laminin, ab-crystallin, phospholipid, galactose and Na/K ATPase-SARM1 complex. Retinoschisin is first observed in the mouse retina on postnatal day 1. During development, all retinal neurons express retinoschisin after differentiation, beginning with the ganglion cells, which are the first to mature, followed by neurons of each of the more distal layers. From P14 onward, it is strongly expressed in the outer half of the inner nuclear layer and by photoreceptor inner segment. All classes of retinal neurons, except horizontal cell, are shown to be labeled with retinoschisin antibody in adults.

Multiple groups have attempted to use gene-therapy approaches for the treatment of diseases of the eye. For example, several groups have used adeno-associated virus (AAV) vectors expressing retinoschisin to complement the mutations of mice harboring retinoschisin gene deletions. Retinal transduction with these vectors resulted in significant levels of retinoschisin protein in all layers of the retina, and improvement of the disease phenotype, including restoration of the normal positive ERG b-wave and a reduction of the cyst-like structures that are characteristic of the disease. The therapeutic effect was durable and persisted throughout the life of the animal.

In addition to the treatment of X-linked retinoschinosis, other groups have evaluated the clinical use of AAV vectors for the treatment of another X-linked retinopathy, Leber congenital amaurosis (LCA), because of congenital retinal pigment epithelium (RPE) 65 deficiency. AAV vectors expressing RPE65 were administered by subretinal injection to a total of nine subjects with LCA. The nine subjects comprised the collective low-dose cohorts of the three studies, each of which have a dose-escalation design. The majority of the treated subjects showed evidence of improvement in retinal function, visual acuity or reduction in nystagmus despite their relatively advanced state of retinal degeneration. Thus, the treatment methods and uses of this disclosure may include the treatment of other ocular diseases in which schisis or cavities play a role in the progression or symptoms of the disease/disorder, including myopic foveoschisis, macular edema with cavities that can complicate retinitis pigmentosa, enhanced blue cone syndrome, age-related macular degeneration, diabetic retinopathy, as well as inflammatory conditions such as uveitis or inflammation following cataract surgery (Irvine-Gass syndrome), and retinal detachments, cystoid macular edema, retinal tears, and other retinal injuries, that may be aided by the adhesion/extracellular matrix protein, retinoschisin.

While the LCA trials used subretinal injection to deliver the vector, this delivery strategy may be problematic for an XLRS trial, as subretinal injection gives geographically localized delivery. Retinoschisin is expressed throughout the retina and optimal treatment of the disease will require transduction of the entire retina. Vector delivery by subretinal injection is limited maximally to about 25% of the retinal area. Although this amount of transduction is sufficient to cover the vicinity of the macula, much of the retina would probably not be transduced, and the untreated area would remain susceptible to retinal detachment and vitreous hemorrhage, which are the major causes of vision loss with this disease. Some additional spread of retinoschisin has been reported in retinas of mice transduced by subretinal injection, but it is not clear how this might scale to human subjects. Subretinal injection of retinas with schisis pathology may be challenging and pose a significant risk to the visual function of the subject. Vitrectomy is usually carried out before subretinal injection. Adhesion of the vitreous to the retina may cause further laminar splitting of the fragile XLRS retina when the surgeon attempts to separate the vitreous from the retina. In addition, the injection itself may also be difficult. If the tip of the injection needle is not positioned deep enough, vector solution may be inadvertently routed into the schisis cavities and exacerbate the intraretinal splitting. An alternative vector administration method would be attractive for XLRS subjects.

In previous work, the inventors described a method for obtaining efficient AAV vector-mediated gene transfer to XLRS retinas without the use of subretinal injection. In that study, all layers of the retinoschisin knockout (Rs1-KO) mouse retina were efficiently transduced with AAV type 2 (AAV2) vectors when administered by simple vitreous injection (Zeng Y, Takada Y, Kjellstrom S, Hiriyanna K, Tanikawa A, Wawrousek E, et al. RS-1 Gene Delivery to an Adult Rs1h Knockout Mouse Model Restores ERG b-Wave with Reversal of the Electronegative Waveform of X-Linked Retinoschisis. Invest Ophthalmol Vis Sci. 2004; 45:3279-85; Kjellstrom S, Bush R A, Zeng Y, Takada Y, Sieving P A. Retinoschisin gene therapy and natural history in the Rs1h-KO mouse: long-term rescue from retinal degeneration. Invest Ophthalmol Vis Sci. 2007; 48:3837-45). However, administration of AAV2 vector leads to a therapy-limiting immune response in the eye, since humans have a high preexisting immunity to AAV2. The inventors developed an AAV vector to complement vitreal administration in humans. The vector was composed of a 3.5-kb human retinoschisin promoter, a human retinoschisin cDNA containing a truncated retinoschisin first intron, the human b-globin polyadenylation site and AAV type 2 (AAV2) inverted terminal repeats, packaged in an AAV type 8 capsid. Intravitreal administration of this vector to Rs1-KO mice resulted in robust retinoschisin expression with a retinal distribution that was similar to that observed in wild-type retina. Immunolabeling was specific to the retinoschisin-expressing cells of the retina with little or no off-target expression in other eye structures, such as the optic nerve, uveal tissue and cornea.

Thus, the present invention addresses the need for an improved method of delivering therapeutic molecules, such as genes encoding therapeutic proteins, to the eye of an individual in need of such treatment, without eliciting a significant immune response, and provides other benefits as well.

SUMMARY OF THE DISCLOSURE

We have surprisingly found that the inventive compositions and methods of administration are capable of inducing the production of proteins in tissues of the eye while minimizing or avoiding unwanted inflammatory responses or other unwanted side effects. Thus, the invention provides expression vectors and therapeutic methods of using such vectors in the treatment of diseases of the eye, particularly disorders of the eye resulting from failure to produce a specific protein in the eye, or the production of a non-functional protein in the eye.

One embodiment of the present invention is a method of treating an individual having a disease of the eye, the method comprising administering to the individuals eye a vector comprising a nucleic acid sequence encoding a therapeutic protein, wherein the expression vector expresses a high level of the therapeutic protein, and wherein administration of the viral vector elicits a minimal immune response. In one embodiment, administration of the vector does not elicit a therapy-limiting immune response within the individual. The nucleic acid encoding the therapeutic protein may be linked to an eye-specific promoter. Further, the promoter may be specific for certain portions of the eye, such as the retina. In such embodiments, a retina-specific promoter may comprise a portion of a retinoschisin gene promoter. In one embodiment, the retina-specific promoter comprises at least a portion of SEQ ID NO:9.

In certain embodiments, genetic elements, such as enhancer elements, may be included to enhance expression of the therapeutic protein. In one embodiment, the therapeutic protein is linked to a promoter comprising an interphotoreceptor retinoid-binding protein (IRBP) enhancer sequence. In one embodiment, the IRBP enhancer sequence comprises SEQ ID NO:12.

Methods of the present invention are useful for treating diseases of the eye. In one embodiment, the disease of the eye is selected from the group consisting of retinoschisis, age-related macular degeneration (AMD), diabetic retinopathy, Leber congenital amaurosis (LCA), retinal detachment (due to disease, injury or spontaneous detachment), cysts, cystoid macular edema, retinitis pigmentosa, and senile schisis. In one embodiment, the disease of the eye is linked with the x-chromosome.

In one embodiment, the therapeutic protein is a retinoschisin protein. The retinoschisin protein may have at least 90% sequence identity to the sequence of a known retinoschisin protein or any portion thereof. For example, the retinoschisin protein may have at least 90% sequence identity to SEQ ID NO:2, or any portion thereof, so long as the protein encoded by a vector of the present invention has at least one activity of a wild-type retinoschisin protein. In one embodiment, a nucleic acid sequence encoding a retinoschisin protein of the present invention comprises at least one splice donor and one lariat/splice acceptor site. The splice donor and the lariat/splice acceptor site may be from intron 1 of a retinoschisin gene. The nucleic acid sequence encoding the therapeutic protein may also be linked to a polyadenylation signal, such as the human beta-globin 3' polyadenylation signal.

In one embodiment of the present invention, the vector comprises adeno-associated virus inverted terminal repeats (ITRs). The ITRs may or may not be identical in sequence. One of the ITRs may lack the REP protein nicking recognition sequence or the D region. At least one UTR may be derived from, or may consist of, the psub201 vector. In one embodiment, the vector comprises SEQ ID NO:16. In one embodiment, the vector comprises capsid proteins from one or more adeno-associated viruses. In one embodiment, the capsid protein is from AAV8. In one embodiment, the vector is administered by intravitreal injection.

One embodiment of the present invention is an expression vector comprising a nucleic acid sequence encoding a therapeutic protein, wherein the expression vector expresses a high level of the therapeutic protein when administered to the eye of an individual. Vectors of the present invention elicit a minimal immune response in the individual when administered to the eye. Further, vectors of the present invention alleviate at least one symptom of retinoschisis when administered to the eye at a dose that elicits an insignificant immune response. Viral vectors useful for treating diseases of the eye may be prepared by incubating expression vectors of the present invention with cells expressing AAV capsid proteins and AAV REP proteins. The AAV capsid and REP proteins may be provided by a plasmid, by a helper virus or by genes introduced into the genome of the cells.

One embodiment of the present invention is an expression vector for use in ocular gene therapy applications comprising: a capsid protein that has low preexisting immunity in humans; an expression cassette that produces a therapeutic level of protein in the individual when administered to the individual at a dose that does not elicit a therapy-limiting immune response within the individual following administration by intravitreal injection; and, a tissue-specific promoter that inhibits or prevents expression of the expression vector in antigen presenting cells and/or tissues that do not normally express the therapeutic protein. In one embodiment, the immune response produced within the individual following administration by intravitreal injection is less than or equal to +2 cells transiently and +1 cells chronically. Further, expression in antigen presenting cells and tissues outside of the eye is less than 1% of expression in a tissue of the eye. In one embodiment, the tissue-specific promoter is a retina-specific promoter. The tissue-specific promoter may comprise at least a portion of SEQ ID NO:9. The expression vector may also comprise adeno-associated virus (AAV) inverted terminal repeat (ITR) sequences. In one embodiment, the expression vector comprises SEQ ID NO:16. The expression vector may also comprise capsid proteins from one or more adeno-associated viruses. In one embodiment, the expression vector comprises capsid proteins from AAV8.

One embodiment of the present invention is a method of treating an individual having a disease of the eye, comprising administering to the patient's eye an expression vector comprising a capsid protein that has low preexisting immunity in humans; an expression cassette that produces a therapeutic level of protein in the individual when administered to the individual at a dose that does not elicit a therapy-limiting immune response within the individual following administration by intravitreal injection; and, a tissue-specific promoter that inhibits or eliminates expression of the expression vector in antigen presenting cells and tissues that do not normally express the therapeutic protein. In one embodiment, the immune response produced within the individual following administration by intravitreal injection is less than or equal to +2 cells transiently and +1 cells chronically. Further, expression in antigen presenting cells and tissues outside of the eye is less than 1% of expression in a tissue of the eye. In one embodiment, the tissue-specific promoter is a retina-specific promoter. The tissue-specific promoter may comprise at least a portion of SEQ ID NO:9. The expression vector may also comprise adeno-associated virus (AAV) inverted terminal repeat (ITR) sequences. In one embodiment, the expression vector comprises SEQ ID NO:16. The expression vector may also comprise capsid proteins from one or more adeno-associated viruses. In one embodiment, the cassette comprises capsid proteins from AAV8.

One embodiment of the present invention is a method of treating X-linked retinoschisis in a human comprising: administering to a human subject diagnosed with, or suspected of having, X-linked retinoschisis a therapeutically effective amount of an expression vector comprising: a capsid protein from AAV8; an expression cassette comprising a retinoschisin gene promoter operably linked to an interphotoreceptor retinoid-binding protein (IRBP) enhancer sequence, adeno-associated virus (AAV) inverted terminal repeat (ITR) sequences, and a human retinoschisin protein, wherein administration of the expression vector causes expression of the human retinoschisin protein in a retinal cell of the subject, and reduces at least one symptom of retinoschisis. The expression vector may be administered using intravitreal, subretinal or subtenon injection techniques. The expression vector may also be administered topically. The expression vector may also be administered to the contralateral eye of the human subject to effect treatment in the effected eye.

The expression vector of the invention is administered in an amount that is therapeutically effective. A therapeutically effective amount includes, for example, a dose between about $1e^{10}$ vg/eye to about $2.5e^{11}$ vg/eye, a dose between about $1e^{8}$ vg/eye to about $1e^{13}$ vg/eye, a dose between about $1e^{9}$ vg/eye to about $1e^{13}$ vg/eye, a dose between about $3e^{9}$ vg/eye to about $1e^{13}$ vg/eye, a dose between about $1e^{10}$ vg/eye to about $1e^{13}$ vg/eye, a dose between about $3e^{10}$ vg/eye to about $1e^{13}$ vg/eye, a dose between about $1e^{11}$ vg/eye to about $1e^{13}$ vg/eye, a dose between about $3e^{11}$ vg/eye to about $1e^{13}$ vg/eye.

In an exemplary embodiment, the methods of this disclosure include the treatment of an eye disease or disorder by administering to a human subject diagnosed with or suspected of having a disease, disorder, or injury of an eye, a therapeutically effective amount of an expression vector that includes an expression vector comprising an expression cassette, wherein the expression cassette comprises a promoter operably-linked to a nucleic acid sequence encoding a retinoschisin gene, including at least a 319-base pair portion of the first intron of the retinoschisin gene, such that administration of the vector causes expression of the human retinoschisin protein in a retinal cell of the human subject, and reduces at least one symptom of the disease, disorder, or injury of the eye. In these methods, the disease, disorder, or injury of an eye may be selected from the group consisting of X-linked retinoschisis (XLRS), myopic foveoschisis, macular edema with cavities that can complicate retinitis pigmentosa, enhanced blue cone syndrome, age-related macular degeneration, diabetic retinopathy, uveitis, inflammation following cataract surgery (Irvine-Gass syndrome), retinal detachment, cystoid macular edema, retinal tear, and retinal injury. In these methods, the vector may be administered by intravitreal injection. In these methods, the expression vector may be administered by intravitreal injection from a polypropylene syringe. In these methods, the expression vector may be administered topically, subretinally or by subtenon delivery. In these methods, the expression vector may be administered at a dose between about 3e8 vg/eye to about 1e13 vg/eye, or a dose between about 1e10 vg/eye to about 1e13 vg/eye.

In the methods of this disclosure, the expression vector may be administered in combination with one or more additional active agents or supportive therapies for treating, preventing, or reducing the severity of the eye disorder, disease, or injury. Exemplary supportive therapies may include surgery, laser therapy (e.g., photocoagulation), anti-angiogenic therapy, VEGF inhibitors such as bevacizumab (Avastin™), ranibizumab (Lucentis™), and Aflibercept (Eylea™), Ca2+ inhibitors (e.g., flunarizine and nifedipine), cryotherapy, hyperbaric oxygenation, Na+ channel blockers (e.g., topiramate), iGluR antagonists (e.g., MK-801, dextromethorphan, eliprodil, and flupirtine), antioxidants (e.g., dimethylthiourea, vitamin E, alph-lipoic acid, superoxide dismutase, catalase, desferrioxamine, mannitol, allopurinol, calcium dobesilate, flupirtine, trimetazidine), anti-inflammatory agents, cyclodiathermy, cyclocryotherapy, ocular filtering procedures, implantation of drainage valves, anti-platelet therapy (e.g., aspirin, ticlopidine, clopidogrel), anti-coagulant therapy (e.g., warfarin and heparin), steroids, systemic or local corticosteroids (e.g., prednisone triamcinolone (Triesence™), and dexamethasone, steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zinc, folic acid, vitamin B6, vitamin B12, vitamin D, calcium, zeaxanthin), vitrectomy, scleral buckle surgery, pneumatic retinopexy, ciliary neurotrophic factor (CNTF) protein, brain-derived neurotrophic factor (BDNF) protein, pigment epithelium-derived factor (PEDF) protein, and lens epithelial derived growth factor (LEDGF), or combinations of these therapies. An exemplary supportive therapy includes concurrent administration with a corticosteroid and a steroid-sparing immunosuppressant, such as an anti-inflammatory agent selected from the group consisting of cyclosporine, mycophenolate mofetil, prednisone, and combinations thereof. In these methods, the administration of the anti-inflammatory agent may be initiated prior to the day of administration of the expression vector. Additionally or alternatively, the administration of the anti-inflammatory agent may continue for at least 30 days after the administration of the expression vector. In these methods, the expression vector may be administered concurrently with a steroidal anti-inflammatory compound and a combination of calcium and Vitamin D supplements.

DESCRIPTION OF ILLUSTRATIVE EMBODIMENTS

Figure 1:
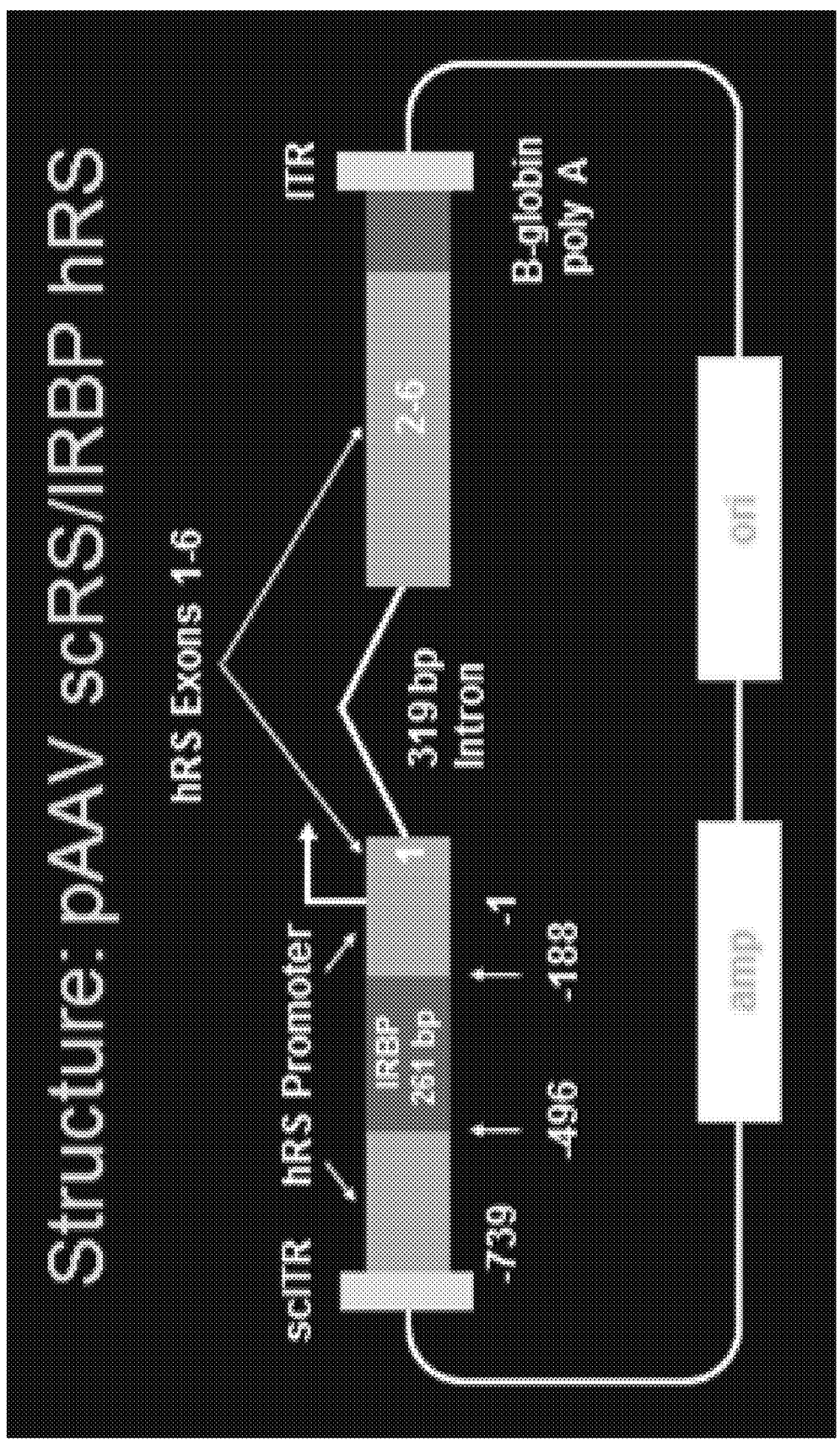
FIG. 1 shows the structure of vector pAAV scRS/IRBP hRS.

The present invention generally relates to improved methods for treating disorders of the eye, including, for example, x-linked retinoschisis (XLRS), retinal detachment (disease-related, injury-induced, and spontaneous), age-related macular degeneration, cysts, cystoid macular edema, retinitis pigmentosa, and senile schisis, as well as vectors useful in such treatment methods. More specifically, the present invention relates to an improved expression vector that is able to effect high level expression of an encoded protein in an eye, with minimal elicitation of an immune response. Because of these characteristics, such vectors are particularly useful for treating diseases of the eye that result from either failure to produce a specific protein in the eye, or the production of a non-functional protein in the eye.

A method of the present invention can generally be accomplished by administering to the eye of a patient in need of such treatment, an expression vector that expresses high levels of a therapeutic molecule in the eye, wherein the administration of the expression vector either fails to elicits an immune response, or elicits a minimal immune response in the eye of the treated patient.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having"

can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

As used herein, the terms individual, subject, and patient are well-recognized in the art, and are herein used interchangeably to refer to any human or other animal in need of treatment of a disease of the eye. Examples include, but are not limited to, humans and other primates, non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. A preferred patient to treat is a human patient. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European.

The present invention can be used to treat any disease of the eye in which the disease results from either inappropriate expression of a protein, or expression of a malfunctioning or dysfunctional form of a protein expressed in the eye. Inappropriate expression of a protein may refer to lack of expression, under-expression or over-expression of a protein. Expression of a malfunctioning form of a protein refers to expression of a protein having one or more mutation(s) that alters the activity of the protein. Alteration of activity may refer to complete inactivation of protein activity, reduction of protein activity or an increase in protein activity.

Altered activity may result from, for example, direct inactivation of an active site or misfolding of the protein. Examples of eye diseases that may be treated using the present invention include, but are not limited to X-linked retinoschisis, age-related macular degeneration (AMD), diabetic retinopathy, Leber congenital amaurosis (LCA), retinal detachment (due to disease, injury, or spontaneous), cysts, cystoid macular edema, retinitis pigmentosa, and senile schisis. Thus, the expression cassette of the invention may include, for example, polynucleotide sequences encoding proteins such as ciliary neurotrophic factor (CNTF), brain-derived neurotrophic factor (BDNF), pigment epithelium-derived factor (PEDF), or pigment epithelium-derived factor (PEDF). For example, the inventors have tested a vector expressing lens epithelial derived growth factor (LEDGF) and demonstrated a protective effect in the RCS rat model of Retinitis pigmentosa (RP).

In a preferred embodiment, the eye disease treated is X-linked retinoschisis. X-linked retinoschisis is a neurodevelopmental retinal abnormally that causes impaired acuity and a propensity to retinal detachment. XLRS is characterized by structural abnormalities in normal lamination of the retinal neuronal and plexiform layers. Clinical examination shows microcysts within the macula, and schisis or internal dissection of the layers of the peripheral retina. X-linked juvenile retinoschisis is caused by mutations in the gene encoding retinoschisin, a 224-amino acid, secreted protein that is expressed only by the retina and pineal.

As used herein, an expression vector is a recombinant nucleic acid molecule comprising a nucleic acid sequence (e.g., open-reading frame (ORF)) that encodes a therapeutic molecule of the present invention, wherein the nucleic acid sequence is linked to a promoter that drives high level expression of the therapeutic molecule when the expression vector is administered to, for example, a subject or an organ, tissue or cell. An expression vector of the present disclosure is produced by human intervention and can be DNA, RNA or variants thereof. The expression vector may be a linear molecule (e.g., a linear nucleic acid molecule, a linear viral genome, etc.) or it may be a circular molecule such as, for example, a plasmid. In one embodiment, an expression vector may comprise one or more nucleic acid sequences from an adeno-associated virus (an AAV vector), a cytomegalovirus (CMV) (a CMV vector), a retrovirus, an adenovirus, a herpes virus, a vaccinia virus (a vaccinia vector), a poliovirus, a Sindbis virus, or any other DNA or RNA virus. In one embodiment, an expression vector may be a DNA plasmid. In one embodiment, an expression vector may be a viral genome. In one embodiment, an expression vector may be a DNA molecule, either linear or circular, comprising nucleic acid sequences from a plasmid and nucleic acid sequences from a viral genome to enable nucleic acid molecule delivery and high-level expression of the encoded therapeutic molecule. In one embodiment, the expression vector is an AAV expression vector. As used herein, an AAV expression vector is a nucleic acid molecule comprising AAV sequences that allow for the replication, packaging and/or expression of the nucleic acid molecule. General methods for the construction of expression vectors are known in the art, and are also disclosed in, for example, *Molecular Cloning: a Laboratory Manual*, $3^{rd}$ edition, Sambrook et al. 2001 Cold Spring Harbor Laboratory Press, and *Current Protocols in Molecular Biology*, Ausubel et al. eds., John Wiley & Sons, 1994, both of which are incorporated herein by reference in their entirety.

As noted above, expression vectors of the present invention comprise promoters that drive high-level expression of nucleic acid sequences encoding therapeutic molecules. As used herein, the phrase "drive expression" refers to the ability of a promoter to promote transcription from an open reading frame (ORF). According to the present disclosure, promoters used in expression vectors of the present invention are specific for cells of the eye (i.e., eye-specific promoters). That is, the promoter only drives expression from the ORF when the expression vector is introduced into a cell of the eye. Such promoters are specific for cells such as, photoreceptor cells, bipolar cells, horizontal cells, amacrine cells, ganglion cells, rods and cones. Examples of such promoters include, but are not limited to, a retinoschisin promoter, a rhodopsin promoter, a rhodopsin kinase promoter, a CRX promoter, and an interphotoreceptor retinoid binding protein (IRBP) promoter. Any promoter that allows eye-specific expression of an encoded protein can be used, so long as the promoter drives high-level expression of the ORF. Thus, in one embodiment, the expression vector comprises an eye-specific promoter.

As used herein, the phrase high-level expression refers to the ability of vectors (i.e., expression vectors and viral vectors comprising expression vectors) of the present invention to express the therapeutic molecules at levels high enough such that the amount of vector required to alleviate symptoms of the eye disease elicits a minimal, or no, immune response. According to the present invention, alleviation of symptoms of eye disease refers to the ability of a therapeutic molecule to reduce, or eliminate, the pathology, and the related symptoms, from an eye disease. Such alleviation may completely eliminate symptoms of eye disease and restore the patients' eye to a normal level of functioning, or it may reduce some of the pathology and restore partial function to the patient's eye. It is understood by those skilled in the art that normal and partial levels of function are relative terms, and are determined by comparing the level of function in the treated eye with the level of function observed in the eyes of a comparable cohort of individuals (e.g., individuals of the same age, race, sex, etc.). Methods of determining the level of eye function, in an individual are known to those skilled in the art. It is also understood by those skilled in the art that determining the levels of therapeutic molecule needed may be an empirical process. However, once such levels are known, they can be quantified by comparing the levels to the levels of expression observed using a reference promoter. Once such a reference has been established, high-level expression may refer to the ability of a promoter to cause expression of an ORF at levels that are significantly higher than the level of expression observed using the reference promoter. An example of a reference promoter is described by Colosi et al. (Gene Therapy, 16, 2000, 916-926). In one embodiment, promoters of the present invention may cause transcription of ORFs at a level that is at least 5×, 10×, 20×, 50×, 100×, 500× or at least 1000× higher than a reference promoter. Levels of expression can be compared by, for example, comparing the level of ORF-specific mRNA produced each expression vector. Methods of performing such comparisons are known to those skilled in the art.

As used herein, a minimal immune response refers to an immune response generated against a construct (e.g., a vector) of the present invention that is not therapeutically limiting. Thus, for example, while constructs of the present invention may elicit an immune response, the immune response is manageable using standard medical practices, such as the administration of steroidal or non-steroidal anti-inflammatory compounds/compositions. Such an immune response may also be referred to as resolvable. In one embodiment, administration of the vector fails to elicit any immune response against the vector. In another embodiment, administration of the vector fails to elicit a therapy-limiting immune response against the vector. In another embodiment, administration of the vector fails to elicit a dosage-limiting immune response against the vector. In another embodiment, administration of the vector fails to elicit a detectable immune response against the vector. In another embodiment, administration of the vector elicits only a therapeutically-manageable immune response against the vector. In another embodiment, less than 50% of the vector is neutralized by intravenous immune globulin (IVIG) at 20 mg/ml in a vector neutralization assay (see, Arbetman, A. E., et al., Novel Caprine Adeno-Associated Virus (AAV) Capsid (AAV-Go.1) Is Closely Related to the Primate AAV-5 and Has Unique Tropism and Neutralization Properties, J Virol. 2005 December; 79(24):15238-15245). In another embodiment, the immune response produced within the individual following administration of the vector is less than or equal to +2 cells transiently and +1 cells chronically.

One type of tissue-specific promoter is an eye-specific promoter. For example, a promoter that drives expression of a ORF only when it is in a cell of the retina (including, for example, bipolar cells, horizontal cells, amacrine cells, ganglion cells, rods and cones) is referred to as a retina-specific promoter. Thus, in one embodiment, the promoter is a retina-specific promoter. In one embodiment, the expression of the viral vector containing an eye-specific promoter in antigen presenting cells and tissues outside of the eye is less than 1% of expression in a tissue of the eye.

One example of a retina-specific promoter is the retinoschisin gene promoter, the sequence of which is represented by SEQ ID NO:9. Within SEQ ID NO:9, bases 1-8 are the engineered NotI site for cloning; bases 9-248 human RS promoter sequence; bases 249-254 are the engineered SalI site for addition of IRBP enhancer; bases 255-515 are the human IRBP enhancer sequence; bases 516-521 are the engineered SalI site for addition of IRBP enhancer; bases 522-750 are the proximal retinoschisin promoter; bases 551-802 are the retinoschisin 1st exon; bases 803-1063 are the splice donor and proximal retinoschisin 1st intron; bases 1064-1071 are the engineered AscI site for ligation to splice acceptor of intron.

Intron sequences are included in the promoter because they increase mRNA export from the nucleus to the cytoplasm compared to an intron-less construct for most cDNAs, resulting in an approximately 10-fold increase in transgene expression. Viruses have evolved other mechanisms to facilitate the export of viral mRNAs that don't involve splicing. By inhibiting splicing, these viruses can divert protein production from host mRNAs to viral mRNA late in viral replication. Elements that viruses use to accomplish this mRNA transport include the WPRE (Woodchuck Hepatitis Virus Posttranscriptional Regulatory Element), and RRE (HIV and SIV rev response element).

Thus, in one embodiment, the promoter comprises at least a portion of a retinoschisin promoter. In a specific embodiment, the portion is a portion of SEQ ID NO:9. In one embodiment, the promoter comprises a nucleotide sequence that is at least 95% identical to at least one sequence selected from the group consisting of SEQ ID NO:10 and SEQ ID NO:11, wherein the promoter has retinoschisin gene promoter activity. In one embodiment, the promoter comprises at least one sequence selected from the group consisting of SEQ ID NO:10 and SEQ ID NO:11, wherein the promoter has retinoschisin gene promoter activity. In one embodiment, the promoter comprises SEQ ID NO:9. In one embodiment, the promoter comprises SEQ ID NO:9. In one embodiment, the promoter consists of SEQ ID NO:9.

The present inventors have discovered that modifications to promoters, such as the retinoschisin promoter, may result in significant improvement in the ability of the promoter to drive expression of an ORF. Examples of modifications that may be useful for improving the performance of promoters of the present invention include sequence mutations (e.g., nucleotide substitutions, additions, or deletions), and the addition, or removal, of regulatory elements, such as transcription factor binding elements, enhancer elements, silencer elements and boundary elements. Examples of such elements include a TATA element, a B recognition element, and an E-box element. Thus, in one embodiment, the eye-specific promoter has been modified so that it comprises heterologous nucleic acid sequences. As used herein, heterologous nucleic acid sequences are nucleic acid sequences that, in their natural setting (e.g., in a genome) are not linked to the sequences to which they are being referenced. For example, with regard to eye-specific promoters present in expression vectors of the present invention, sequences that are heterologous thereto are any nucleic acid sequences not found in association with such eye-specific promoter sequences in cells of the eye. Preferably, any elements added to the promoter region are specific to cells of the eye. In one embodiment, an expression vector of the present invention comprises a promoter comprising an enhancer element. One example of a useful enhancer element is an interphotoreceptor retinoid binding protein (IRBP) enhancer element, which is represented by SEQ ID NO:12. In one embodiment, the promoter comprises at least a portion of the IRBP promoter. In one embodiment, the enhancer element comprises a nucleotide sequence at least 95% identical to SEQ ID NO:12, wherein the enhancer retains the ability to enhance transcription from a nearby promoter (i.e., a promoter within 500 nucleotides of either end of the enhancer sequence). In one embodiment, the IBRP enhancer element comprises SEQ ID NO:12. In one embodiment, the IRBP enhancer element is linked to one end of the eye-specific promoter. In one embodiment, the IRBP enhancer element is inserted within the sequence of the eye-specific promoter. In one embodiment, the IRBP enhancer element is inserted within the sequence of the retinoschisin gene promoter.

As used herein, a therapeutic molecule is a molecule that when introduced within the eye, is capable or ameliorating or eliminating symptoms of a disease of the eye. Examples of therapeutic molecules include proteins and RNAs, including siRNAs. Such molecules may act by providing an activity that is missing, or significantly reduced, in a diseased eye. Such molecules may also act by modifying or reducing an activity that is over-expressed, or significantly elevated above normal levels, in a diseased eye. For example, a therapeutic molecule may be a protein possessing an activity (e.g., specific binding activity, enzymatic activity, transcriptional regulation activity, etc.) that is lacking in cells of the eye. Lack of such activity may result from failure of the cells to produce the protein, production of a mutated, inactive form of the protein, or misfolding of a protein resulting in an inactive form. In some cases, introducing a "good" (i.e., functional) copy of the protein may alleviate symptoms of the disease by directly replacing the missing activity. Alternatively, therapeutic molecules may act by increasing or decreasing the activity of other proteins in cells of the eye. For example, the therapeutic protein may bind to another protein and thereby either decrease, or eliminate the activity of the second protein. Alternatively, binding of the therapeutic protein to another protein in cells of the eye may result in stabilization of such protein and/or an increase in the related activity. Finally, the therapeutic molecule may increase or decrease transcription of genes, or the translation of transcripts from genes in cells of the eye. For example, a therapeutic protein may bind to a transcriptional region of a gene and thereby increase or decrease transcription of that gene.

Any protein can be used as a therapeutic protein, provided the protein possesses an activity that is of therapeutic benefit in treating a disease of the eye. For example, if the disease to be treated is related to abnormal blood vessel growth (e.g., wet, age-related, macular degeneration (AMD), diabetic retinopathy, etc.) a useful therapeutic protein could be any protein having anti-angiogenic activity. As a further example, if the disease to be treated is due to neuropathy in the eye (e.g., glaucoma, retinitis pigmentosa, etc.) a useful therapeutic protein, may be any protein, or molecule, that provides a neuroprotective effect in the eye. Examples of such proteins include, but are not limited to, ciliary neurotrophic factor (CNTF), brain-derived neurotrophic factor (BDNF) and pigment epithelium-derived factor (PEDF).

One example of a useful therapeutic protein is retinoschisin protein, which is a 224-amino acid, discoidin domain-containing, retina-specific, secretory protein. Loss of retinoschisin protein function has been implicated in X-linked retinoschinosis. As used herein, a retinoschisin protein refers to a full-length retinoschisin protein, or any portion thereof, that has at least one activity of a wild-type retinoschisin protein. Thus, in one embodiment, the therapeutic protein comprises at least a portion of a retinoschisin protein. Such a portion may comprise at least 50 amino acids, at least 75 amino acids, at least 125 amino acids, at least 150 amino acids, at least 175 amino acids or at least 200 amino acids, so long as the resulting therapeutic protein possesses at least one function of a full length retinoschisin protein. In a related embodiment, the therapeutic protein is a retinoschisin protein having at least 90%, at least 95%, at least 97%, at least 98% or at least 99% sequence identity to a full-length retinoschisin protein, or any portion thereof, that has at least one activity of a wild-type retinoschisin protein. In a specific embodiment, the therapeutic protein is a human retinoschisin protein having at least 90%, at least 95%, at least 97%, at least 98% or at least 99% sequence identity to a full-length human retinoschisin protein (SEQ ID NO:2 or SEQ ID NO:5), or any portion thereof, that has at least one activity of a wild-type retinoschisin protein. Known functions of the retinoschisin protein include binding to anionic phospholipids, binding to the sterile alpha and TIR motif-containing protein (SARM1), binding to alpha-B crystalline protein and binding to beta2 laminin.

As noted above, the retinoschisin protein comprises a discoidin domain, a structure that has been found in other secreted and transmembrane proteins. While the function of the discoidin domain in the retinoschisin protein is not well understood, in other proteins it has been implicated in cell-cell adhesion and cell-cell signaling. With regard to retinoschisin, it has been demonstrated that introduction of mutations that alter the discoidin domain structure result in loss of retinoschisin function and development of x-linked retinoschisis (see, Wu and Molay, J. Biol. Chem., 278(30): 28139-28146, 2003, which is incorporated herein by reference).

In one embodiment, the therapeutic protein comprises at least 50 contiguous amino acids, at least 75 contiguous amino acids, at least 125 contiguous amino acids, at least 150 contiguous amino acids, at least 175 contiguous amino acids or at least 200 contiguous amino acids of a human retinoschisin protein, so long as the resulting therapeutic protein retains at least one function of a full length retinoschisin protein. In one embodiment, the therapeutic protein comprises at least 50 contiguous amino acids, at least 75 contiguous amino acids, at least 125 contiguous amino acids, at least 150 contiguous amino acids, at least 175 contiguous amino acids or at least 200 contiguous amino acids from SEQ ID NO:2, so long as the therapeutic protein retains at least one function of a full length retinoschisin protein. In one embodiment, the therapeutic protein comprises SEQ ID NO:2 or SEQ ID NO:5. In one embodiment, the therapeutic protein consists of SEQ ID NO:2 or SEQ ID NO:5.

In one embodiment, a therapeutic protein comprises the discoidin domain of retinoschisin. In one embodiment, a therapeutic protein comprises the discoidin domain of a human or mouse retinoschisin protein. In one embodiment, a therapeutic protein comprises the discoidin domain of a protein comprising SEQ ID NO:2 or SEQ ID NO:5. In one embodiment, a therapeutic protein comprises SEQ ID NO:8.

Therapeutic proteins of the present invention may also be variants of wild-type proteins. As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations, or they can be engineered through the use of genetic engineering technique know to those skilled in the art. Examples of such techniques may be found in Sambrook J, Fritsch E F, Maniatis T et al., in Molecular Cloning—A Laboratory Manual, 2nd Edition, Cold Spring Harbor Laboratory Press, 1989, pp. 9.31-9.57, or in Current Protocols in Molecular Biology, John Wiley & Sons, N.Y. (1989), 6.3.1-6.3.6.

With regard to variants, any type of alteration in the amino acid, or nucleic acid, sequence is permissible so long as the resulting variant protein retains the function of the wild-type protein. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;

2) neutral hydrophilic: Cys, Ser, Thr;

3) acidic: Asp, Glu;

4) basic: Asn, Gln, His, Lys, Arg;

5) residues that influence chain orientation: Gly, Pro; and 6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the therapeutic protein, or to increase or decrease the immunogenicity, solubility or stability of the therapeutic proteins described herein. Exemplary amino acid substitutions are shown below:

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affect a protein's activity" refers to a decrease in the activity of a protein by at least 10%, at least 20%, at least 30%, at least 40% or at least 50%. Methods of measuring such activities are known to those skilled in the art.

In one embodiment, the therapeutic protein comprises an amino acid sequence at least 95%, at least 98% or at least 99% identical to the sequence of a wild-type retinoschisin protein, so long as the resulting therapeutic protein retains at least one function of a full length retinoschisin protein. In one embodiment, the therapeutic protein comprises an amino acid sequence at least 95%, at least 98% or at least 99% identical to the sequence of a wild-type human, retinoschisin protein, so long as the resulting therapeutic protein retains at least one function of a full length retinoschisin protein. In one embodiment, the therapeutic protein comprises an amino acid sequence at least 95%, at least 98% or at least 99% identical to the sequence of SEQ ID NO:(SEQ ID NO:2 or SEQ ID NO:5), so long as the resulting therapeutic protein retains at least one function of a full length retinoschisin protein. In one embodiment, a therapeutic protein comprises an amino acid sequence at least 90%, at least 95% identical, at least 97% identical to SEQ ID NO:8, wherein the therapeutic protein retains at least one function of a full length retinoschisin protein. In one embodiment, a therapeutic protein comprises an amino acid sequence at least 90%, at least 95% identical, at least 97% identical to SEQ ID NO:8, wherein the amino acid sequence comprises those cysteine residues necessary for retinoschisin function.

A therapeutic molecule may also be a nucleic acid molecule, such as an RNA molecule, that regulates expression of specific genes. For example, a small inhibitory RNA (siRNA) can bind to specific transcripts, thereby preventing such transcripts from being translated. In one embodiment, the therapeutic molecule is a siRNA.

It is well appreciated in the art that the efficiency of delivery of nucleic acid molecules into cells may be increased using delivery vehicles such as viral vectors. Thus, in one embodiment, the expression vector may comprise nucleic acid sequences that allow replication of the vector by viral systems and packaging of the expression vector into a viral vector. One example of such sequences is the inverted terminal repeat (ITR) sequences found in adeno-associated viruses. Examples of viral replication systems are known in the art and include, for example, the use of helper viruses (e.g., adenoviruses) as well as recombinant cells expressing proteins that recognize AAV ITR sequences and direct replication of nucleic acid molecules comprising ITR sequences (e.g., cells expressing AAV Rep proteins). Similarly, packaging systems that can package the expression vector into viral vectors are known to those in the art (e.g., recombinant cells expressing AAV capsid proteins). Thus, in one embodiment, the expression vector comprises at least one AAV ITR sequence. In one embodiment, the expression vector comprises a pair of AAV ITR sequences. AAV ITR sequences useful for constructing expression vectors of the present invention can be from any AAV so long as they are capable of allowing replication of the expression vector by an AAV replication system, and packaging of the expression vector into a viral vector. In one embodiment, the expression vector comprises at least one ITR sequence from a virus selected from the group consisting of AAV1, AAV2, AAV4, AAV5, AAV7, AAV8 and AAV9. In one embodiment, the expression vector comprises at least one ITR sequence from AAV8.

The inventors have found that modification of ITR sequences may result in an increase in the expression of the therapeutic protein encoded by the expression vector. For example, it is well-known in the art that ITR sequences contain specific regions, such as the rep nicking sequence and the D region, that are necessary for proper synthesis of a complementary nucleic acid strand and resolution o the duplex molecule into individual AAV genomes. Removal of one or more of these regions causes failure of the duplex genomic nucleic acid molecule to resolve into two individual molecules, producing in a self-complementary molecule, which results in an increase in expression of the encoded protein. Thus, in one embodiment, the expression vector comprises at least one ITR that has been modified at the rep nicking sequence or within the D region. In one embodiment, the expression vector comprises at least one ITR that lacks the rep nicking sequence. In one embodiment, the expression vector comprises at least one ITR that lacks the D region. In one embodiment, the expression vector comprises at least one ITR that lacks the rep nicking sequence and the D-region.

As has been discussed, packaging of the expression vector into a viral vector may increase the efficiency of delivery of the expression vector into cells of the eye. As used herein, a viral vector refers to a particle that comprises capsid proteins from one or more viruses, and which can encapsulate, or contain, the expression vector within the particle. Viral vectors may increase the efficiency of delivery by binding to receptors on the cell surface and becoming internalized (e.g., by fusion with the cell membrane or by endocytosis) thereby delivering the expression vector into the interior of cells of the eye. The capsid proteins of any virus can be used to construct viral vectors, so long as the resulting viral vector is capable of delivering the expression vector into cells of the eye. Preferred capsid proteins to be used in constructing viral vectors may be obtained from a virus selected from the group consisting of an adeno-associated virus (an AAV virus), a cytomegalovirus (CMV), a retrovirus, an adenovirus, a herpes virus, a vaccinia virus, a poliovirus, and a Sindbis virus.

In one embodiment, the viral vector comprises capsid proteins from an adeno-associated virus (AAV). AAV is a small (approx. 20 nm in diameter), non-enveloped virus from the parvoviridae family. AAV is distinct from other members of this family in that it lacks the ability to replicate by itself and thus relies on the external provision of replication and packaging functions. These functions may be supplied by a helper virus or by cells that have been engineered to provide such functions. The genome of AAV virus consists of a single linear segment that is approximately 5 kb in length. The ends of the genome consist of short inverted repeat (ITR) sequences that fold into T-shaped hairpin structures that serve as the viral origin of replication. The ITR region contains two elements that have been described as central to the function of the ITR. These elements are the D region repeat motif and the terminal resolution site (trs). The repeat motif binds to Rep proteins, which are involved in regulation of replication, transcription and production of progeny genomes. Binding of the Rep protein positions the Rep protein so that it can cleave at the trs.

Currently there are several known AAVs, examples of which include AAV1, AAV2, AAV3, AAV4, AAV5, AAV7, AAV8 and AAV9. The capsid protein from any AAV can be used so long as the resulting particle is able to encapsulate an expression vector of the present invention and deliver it into cells of the eye. In a preferred embodiment, the capsid proteins are from AAV8. Thus, one embodiment of the present invention is a viral vector comprising capsid proteins from AAV8 (an AAV8 vector), wherein the viral vector comprises an expression vector of the present invention.

It has been discovered that the presence of human pre-existing antibodies reactive with primate AAV serotypes may reduce the clinical usefulness of vectors made from these AAV serotypes (Arbetman, et. al., supra). In particular, a significant proportion of humans have antibodies that neutralize AAV serotypes 1 to 6, and experiments have demonstrated that the injection of human antibodies into mice to generate sera with low neutralizing titers significantly reduced transduction with AAV2 vectors. To address the problem of human preexisting humoral immunity to AAV serotypes, the viral vectors of the present invention preferably comprise AAV capsid proteins having little or no preexisting immunity in humans, including, but not limited to AAV8 capsid proteins.

As used herein, an AAV8 capsid protein refers to a full-length AAV8 capsid protein, or any portion thereof that is able to form a viral particle, encapsulating an expression vector of the preset invention and delivering the encapsulated expression vector into a cell. In one embodiment, the viral vector comprises a protein comprising at least 50 amino acids, at least 75 amino acids, at least 100 amino acids, at least 150 amino acids or at least 200 amino acids from an AAV8 capsid protein. In one embodiment, the viral vector comprises at least 50 amino acids, at least 75 amino acids, at least 100 amino acids, at least 150 amino acids or at least 200 amino acids from SEQ ID NO:14. In one embodiment, the viral vector comprises a protein comprising SEQ ID NO:14.

Variants of AAV8 capsid proteins can also be used to produce viral vectors of the present invention, so long as the variants protein is able to form a viral particle, encapsulating an expression vector of the preset invention and delivering the encapsulated expression vector into a cell. In one embodiment, the viral particle comprises a capsid protein at least 90% identical, at least 95% identical, at least 97% identical or at least 99% identical to an AAV8 capsid protein. In one embodiment, the viral particle comprises a capsid protein at least 90% identical, at least 95% identical, at least 97% identical or at least 99% identical to SEQ ID NO:14. Methods of the present invention comprise administering vectors of the present invention to the eye of an individual in need of such treatment. Any method of administration can be used to deliver the expression vector, so long as the expression vector is delivered into the interior of the eye. For example, in one embodiment the expression vector may be encapsulated in other molecules (e.g., proteins, lipids, etc) such that the encapsulated expression vector is able to traverse the outer layers of the eye (i.e., cornea, iris, sclera, pupil, lens, or conjunctiva) and enter into the intraocular fluid (also referred to as the aqueous humor). In one embodiment, the expression vector is encapsulated in a viral vector that is able to traverse the outer layers of the eye and enter into the intraocular fluid. Thus, in certain embodiments the expression vector is administered topically to the eye. In preferred embodiments, the expression vector, either alone or in an encapsulated form, is injected into the eye. This may include intramuscular, intradermal, subcutaneous, subconjunctival and sub-Tenon's, intravitreal, subretinal, intravenous and intracameral injections. Such injections can deliver the expression vector, or a viral vector containing the expression vector, to the intraocular fluid or to a location within the retina. In one embodiment, the injection delivers the expression vector, or a viral vector containing the expression vector, to the intraocular fluid. In one embodiment, the injection delivers the expression vector, or a viral vector containing the expression vector, into the retina. In one embodiment, the expression vector is administered by intravitreal injection. In another embodiment, the expression vector is administered by subretinal injection. In another embodiment, the expression vector is administered by sub-Tenon's injection Methods of performing intraocular injections are known to those skilled in the art. In all of these embodiments, the expression vector is preferably contained within and administered via a polypropylene syringe. When administered by these means, the single injection dosage may include between $1e^8$ vg/eye and $3e^{13}$ vg/eye (i.e., $1 \times 10^8$ vector genomes (vg) per eye to $3 \times 10^{13}$ vector vector genomes per eye). When administered by these means, the single injection dosage may be between $3e^8$ vg/eye and $1e^8$ vg/eye, or between $1e^9$ vg/eye and $1e^{13}$ vg/eye, or between $3e^9$ vg/eye and $1e^{13}$ vg/eye, or between $1e^{10}$ vg/eye and $1e^{13}$ vg/eye, or between $3e^{10}$ vg/eye and $1e^{13}$ vg/eye, or between $1e^{11}$ vg/eye and $1e^{13}$ vg/eye, or between $3e^{11}$ vg/eye and $1e^{13}$ vg/eye, or between $1e^{12}$ vg/eye and $1e^{13}$ vg/eye, or between $3e^{12}$ vg/eye and $1e^{13}$ vg/eye.

The present invention also provides vectors for performing the methods disclosed herein. Thus, one embodiment of the present invention is an expression vector encoding a therapeutic protein for treating a disease of the eye, wherein the expression vector expresses high-levels of a therapeutic protein when administered to the eye of an individual in need of such treatment. In one embodiment, the expression vector is a plasmid. In one embodiment, the expression vector is a linear nucleic acid molecule. In one embodiment, the expression vector comprises DNA. In one embodiment the expression vector comprises RNA. In one embodiment, the expression vector comprises one or more sequences from one or more viruses. In a further embodiment, the expression vector comprises one or more nucleic acid sequences from an adeno-associated virus (an AAV vector), a cytomegalovirus (CMV) (a CMV vector), a retrovirus, an adenovirus, a herpes virus, a vaccinia virus (a vaccinia vector), a poliovirus, a Sindbis virus, or any other DNA or RNA virus. In one embodiment, the expression vector comprises nucleic acid sequences from an AAV selected from the group consisting of AAV1, AAV2, AAV4, AAV5, AAV7, AAV8 and AAV9. In a preferred embodiment, the expression vector comprises nucleic acid sequences from AAV8.

Expression vectors of the present invention provide high-level expression of therapeutic molecules capable of alleviating the symptoms of a disease of the eye. Thus, one embodiment of the present invention is an expression vector encoding a therapeutic molecule, wherein the expression vector comprises a promoter that drives high-level expression the therapeutic molecule. In one embodiment, the promoter is an eye-specific promoter. In one embodiment, the promoter is a retina-specific promoter. In one embodiment, the promoter comprises at least a portion of a retinoschisin promoter. In one embodiment, the portion is from SEQ ID NO:9. In one embodiment, the promoter comprises SEQ ID NO:9. In one embodiment, the promoter consists of SEQ ID NO:9. In one embodiment, the promoter comprises a nucleotide sequence at least 95% identical to at least one sequence selected from the group consisting of SEQ ID NO:10 and SEQ ID NO:11, wherein the promoter has retinoschisin gene promoter activity. In one embodiment, the promoter comprises at least one sequence selected from the group consisting of SEQ ID NO:10 and SEQ ID NO:11, wherein the promoter has retinoschisin gene promoter activity. In one embodiment, the promoter comprises SEQ ID NO:9.

Expression vectors of the present invention may also comprise promoters that have been modified in order to increase or decrease the expression of the encoded therapeutic molecule. Thus, in one embodiment, the expression vector comprises a promoter, such as a retinoschisin promoter that has been modified by mutation of the promoter sequence. In one embodiment, the expression vector comprises a promoter that is lacking one or more genetic element, such as, a TATA element, a B recognition element or an enhancer element. One embodiment is an expression vector encoding a therapeutic molecule, wherein the encoding sequence is linked to a promoter that drives high level expression of the encoded molecule, wherein the expression vector comprises an enhancer element. In one embodiment, the enhancer element is an IRBP enhancer element. In one embodiment, the enhancer element comprises SEQ ID NO:12. In one embodiment, the enhancer element comprises a nucleotide sequence at least 95% identical to SEQ ID NO:12, wherein the enhancer retains the ability to enhance transcription from a nearby promoter (i.e., a promoter within 500 nucleotides of either end of the enhancer sequence). In one embodiment, the IRBP enhancer element is linked to one end of the eye-specific promoter. In one embodiment, the IRBP enhancer element is inserted within the sequence of the eye-specific promoter. In one embodiment, the IRBP enhancer element is inserted within the sequence of the retinoschisin gene promoter.

As noted, expression vectors of the present invention encode therapeutic molecules for the treatment of diseases of the eye. The therapeutic molecule can be any molecule that is useful for treating disease of the eye when expressed in cells of the eye. Thus, one embodiment of the present invention is an expression vector encoding a therapeutic molecule, wherein the expression vector comprises a promoter that drives high-level expression of the therapeutic molecule in the eye, and wherein the expression of the therapeutic molecule in cells of the eye alleviates the symptoms of a disease of the eye. In one embodiment, the therapeutic molecule is an RNA molecule. In one embodiment, the therapeutic molecule is an siRNA molecule. In one embodiment, the therapeutic molecule is a protein. In one embodiment, the therapeutic molecule is a protein normally found in the eye. In one embodiment, the therapeutic molecule is a protein comprising at least a portion of a retinoschisin protein, wherein the encoded protein has retinoschisin protein activity. In one embodiment, the therapeutic molecule is a protein that comprises at least 50 amino acids, at least 75 amino acids, at least 100 amino acids, at least 150 amino acids, or at least 200 amino acids from a retinoschisin protein, wherein the encoded protein has retinoschisin protein activity. In one embodiment, the therapeutic molecule is a protein that comprises at amino acids 63-224 from a retinoschisin protein, wherein the encoded protein has retinoschisin protein activity. In one embodiment, the therapeutic molecule is a protein that comprises at least 50 amino acids, at least 75 amino acids, at least 100 amino acids, at least 150 amino acids, or at least 200 amino acids from SEQ ID NO:2. In one embodiment, the therapeutic protein comprises at least amino acids 63-224 from SEQ ID NO:2, wherein the encoded protein has retinoschisin activity. In one embodiment, the therapeutic protein comprises SEQ ID NO:2 or SEQ ID NO:5. In one embodiment, the therapeutic protein consists of SEQ ID NO:2 or SEQ ID NO:5.

Therapeutic proteins encoded by expression vectors of the present invention may also be variants of proteins that alleviate the symptoms of a disease of the eye. Such variants may comprise one or more amino acid substitutions, deletions or insertions. Thus, one embodiment of the present invention is an expression vector encoding a variant of a wild-type therapeutic protein, wherein the expression vector comprises a promoter that drives high-level expression the variant protein in the eye, and wherein the expression of the variant protein in cells of the eye alleviates the symptoms of a disease of the eye. In one embodiment, the therapeutic protein comprises an amino acid sequence at least 95%, at least 98% or at least 99% identical to the sequence of a wild-type therapeutic protein, wherein the variant protein retains the function of the wild-type protein. In one embodiment, the expression vector encodes a variant of a wild-type retinoschisin protein. In one embodiment, the encoded protein comprises an amino acid sequence at least 95%, at least 98% or at least 99% identical to the sequence of a wild-type retinoschisin protein, wherein the encoded protein has retinoschisin activity. In one embodiment, the encoded protein comprises an amino acid sequence at least 95%, at least 98% or at least 99% identical to the sequence of a wild-type human, retinoschisin protein, wherein the encoded protein has retinoschisin activity. In one embodiment, the therapeutic protein comprises an amino acid sequence at least 95%, at least 98% or at least 99% identical to the sequence of SEQ ID NO:(SEQ ID NO:2 or SEQ ID NO:5), wherein the encoded protein has retinoschisin activity.

Expression vectors of the present invention may be packaged into viral vectors in order to improve the efficiency of their delivery. Thus, one embodiment of the present invention is an expression vector encoding a therapeutic molecule, wherein the expression vector comprises a promoter that drives high-level expression the therapeutic molecule in the eye, wherein the expression of the therapeutic molecule in cells of the eye alleviates the symptoms of a disease of the eye, and wherein the vector comprises nucleic acid sequences that direct the replication of, transcription from, or packaging of the expression vector. In one embodiment, the expression vector comprises a sequence that allows the packaging of the expression vector into a viral vector. In one embodiment, the expression vector comprise one or more ITR sequences from a virus selected from the group consisting of AAV1, AAV2, AV4, AAVS, AAV7, AAV8 and AAV9. In one embodiment, the expression vector comprises one or more ITR from AAV8. In one embodiment, the expression vector comprises at least one ITR sequence comprising at least a portion of an AAV8 ITR, wherein the ITR is still able to direct replication, transcription and packaging of the expression vector.

ITRs of expression vectors of the present invention may also be modified to improve the characteristics of the expression vector. Thus, one embodiment of the present invention is an expression vector encoding a therapeutic molecule, wherein the expression vector comprises a promoter that drives high-level expression the therapeutic molecule in the eye, wherein expression of the therapeutic molecule in cells of the eye alleviates the symptoms of a disease of the eye, and wherein the vector comprises two or more AAV ITR sequences, wherein at least one ITR lacks the rep nicking sequence or the D region. In one embodiment, the expression vector comprises at least one ITR that lacks a rep nicking sequence. In one embodiment, the expression vector comprises at least one ITR that lacks a D region sequence. In one embodiment, the expression vector comprises at least one ITR that lacks both the rep nicking sequence and the D region sequence.

The present invention also provides viral vectors useful for practicing the disclosed methods. Viral vectors of the present invention comprise an expression vector of the present invention encapsulated in viral capsid proteins. Encapsulation of expression vectors within such capsid proteins increases the efficiency with which expression vectors are delivered into cells of the eye. Viral vectors of the present invention produce either insignificant, or no, immune response when administered to the eye of an individual. Without being bound by theory, the inventors believe that this is because the level of expression of the therapeutic protein is high enough that the dose of viral vector required to alleviate symptoms of the disease being treated may be low enough that it either fails to elicit an immune response or it elicits an insignificant immune response. In this context, an "insignificant immune response" means an immune response that this either not therapy limiting, or is not dose limiting or may be clinically managed by adjusting the dosage amount or timing or by the concurrent administration of anti-inflammatory agent (steroidal or non-steroidal), or a combination of these factors. Thus, one embodiment of the present invention is a viral vector comprising an expression vector encoding a therapeutic protein for treating a disease of the eye, wherein the expression vector expresses high-levels of a therapeutic protein when administered to the eye of an individual, wherein the expression vector is encapsulated by capsid proteins from one or more viruses. In one embodiment, the one or more viruses are selected from the group consisting of an adeno-associated virus (an AAV virus), a cytomegalovirus (CMV), a retrovirus, an adenovirus, a herpes virus, a vaccinia virus, a poliovirus, and a Sindbis virus. In a preferred embodiment, the viral capsid proteins are from AAV. In one embodiment the viral capsid proteins are from AAV8. In one embodiment, the viral capsid protein comprises SEQ ID NO:14.

Viral vectors of the present invention may also be constructed using functional portions of viral capsid proteins. Thus, one embodiment of the present invention is a viral vector comprising an expression vector encoding a therapeutic molecule for treating a disease of the eye, wherein the expression vector expresses high-levels of a therapeutic molecule when administered to the eye of an individual, and wherein the expression vector is encapsulated by proteins comprising at least a portion of a capsid protein from one or more viruses, wherein the proteins comprising at least a portion of a capsid proteins from one or more viruses self assemble into a viral vector. In one embodiment, the encapsulating proteins comprise at least a portion of capsid protein from one or more AAVs. In one embodiment, the encapsulating proteins comprise at least 50 amino acids, at least 75 amino acids, at least 100 amino acids, at least 150 amino acids or at least 200 amino acids from a capsid protein from one or more AAVs. In a preferred embodiment, the encapsulating protein comprises at least a portion of an AAV8 capsid protein. In one embodiment, the encapsulating proteins comprise at least 50 amino acids, at least 75 amino acids, at least 100 amino acids, at least 150 amino acids or at least 200 amino acids from an AAV8 capsid protein. In one embodiment, the encapsulating protein comprises at least 50 amino acids, at least 75 amino acids, at least 100 amino acids, at least 150 amino acids or at least 200 amino acids from SEQ ID NO:14.

Viral vectors of the present invention may also be constructed using variants of viral capsid proteins. Thus, one embodiment of the present invention is a viral vector comprising an expression vector encoding a therapeutic molecule for treating a disease of the eye, wherein the expression vector expresses high-levels of a therapeutic molecule when administered to the eye of an individual, and wherein the expression vector is encapsulated by proteins comprising an amino acid sequence at least 90% identical, at least 95% identical, at least 97% identical or at least 99% identical to a capsid protein from a virus selected from an adeno-associated virus (an AAV virus), a cytomegalovirus (CMV), a retrovirus, an adenovirus, a herpes virus, a vaccinia virus, a poliovirus, and a Sindbis virus, wherein the encapsulating proteins are able to self-assemble into a viral vector. In one embodiment, the encapsulating proteins comprise an amino acid sequence at least 90% identical, at least 95% identical, at least 97% identical or at least 99% identical to an AAV capsid protein. In a preferred embodiment, the encapsulating proteins comprise an amino acid sequence at least 90% identical, at least 95% identical, at least 97% identical or at least 99% identical to an AAV8 capsid protein. In one embodiment, the encapsulating proteins comprise an amino acid sequence at least 90% identical, at least 95% identical, at least 97% identical or at least 99% identical to SEQ ID NO:14.

As described above, the methods of the present disclosure include the use of expression vectors and compositions comprising these vectors, optionally in combination with one or more supportive therapies, to treat or prevent a disorder of the eye, improve vision (e.g., increase visual acuity and/or visual field) in a patient that has a disorder of the eye, and/or to treat or prevent one or more complications of a disorder of the eye or a complication or side effect of a treatment for a disorder of the eye. in a subject in need thereof.

Such supportive therapies may comprise the administration of one or more therapies for treating or preventing the disorder in addition to administration of an expression vector of this disclosure. For example, such supportive therapy may include surgery, laser therapy (e.g., photocoagulation), anti-angiogenic therapy, VEGF inhibitors such as bevacizumab (Avastin™), ranibizumab (Lucentis™), and Aflibercept (Eylea™), $Ca^{2+}$ inhibitors (e.g., flunarizine and nifedipine), cryotherapy, hyperbaric oxygenation, $Na^+$ channel blockers (e.g., topiramate), iGluR antagonists (e.g., MK-801, dextromethorphan, eliprodil, and flupirtine), anti-oxidants (e.g., dimethylthiourea, vitamin E, alph-lipoic acid, superoxide dismutase, catalase, desferrioxamine, mannitol, allopurinol, calcium dobesilate, flupirtine, trimetazidine), anti-inflammatory agents, cyclodiathermy, cyclocryotherapy, ocular filtering procedures, implantation of drainage valves, antiplatelet therapy (e.g., aspirin, ticlopidine, clopidogrel), anticoagulant therapy (e.g., warfarin and heparin), steroids, systemic or local corticosteroids (e.g., prednisone triamcinolone (Triesence™), and dexamethasone, steroid-sparing immunosuppressants (e.g., cyclosporine, azathioprine, cyclophosphamide, mycophenolate, mofetil, infliximab and etanercept), dietary supplements (e.g., vitamin C, vitamin E, lutein, zinc, folic acid, vitamin B6, vitamin B12, vitamin D, calcium, zeaxanthin), vitrectomy, scleral buckle surgery, pneumatic retinopexy, ciliary neurotrophic factor (CNTF) protein, brain-derived neurotrophic factor (BDNF) protein, pigment epithelium-derived factor (PEDF) protein, and lens epithelial derived growth factor (LEDGF).

For example, patients afflicted with retinoschisis and treated with an expression vector of this disclosure may optionally be treated with one or more supportive therapies, such as corticosteroids (e.g., prednisone or triamcinolone), and steroid-sparing immunosuppressants (e.g., cyclosporine, azathioprine, cyclophosphamide, mycophenolate, mofetil, infliximab and etanercept) in combination with the expression vectors of this disclosure.

As used herein, "in combination with," "in conjunction with" or "conjoint administration" refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more expression vectors of this disclosure can be administered concurrently with, prior to, or subsequent to, one or more other additional agents or supportive therapies. In general, each therapeutic agent will be administered at a dose and/or on a time schedule determined for that particular agent and with the judgment and expertise of the treating health care professional. The particular combination to employ in a regimen will typically take into account compatibility of the expression vector of the present disclosure with the supportive therapy and/or the desired effects and side effects of such therapy.

Such supportive therapies may be initiated months, weeks, days, hours, or minutes in advance of the intended time of treatment with the expression vectors of this disclosure. Alternatively or additionally, supportive therapies may be administered simultaneously with the expression vectors of this disclosure. Additionally, such supportive therapies may be continued for minutes, hours, days, weeks, or months after the time of treatment with the expression vectors of this disclosure. For example, anti-inflammatory or immunosuppressive therapies may be initiated several weeks or days in advance of the intended time of treatment with the expression vectors of this disclosure, and may be continued for several weeks or months following the treatment, before being discontinued, which may include a tapering regimen to gradually decrease the dosage or frequency of the administered anti-inflammatory/immunosuppressive medication.

The present invention also provides methods for producing viral vectors for use in methods of the present invention. Thus, one embodiment of the present invention is a method to produce a viral vector for treating a disease of the eye, comprising contacting an expression vector of the present invention with a packaging system, wherein the expression vector comprises sequences that direct packaging of the expression vector into a viral vector. In one embodiment, the expression vector encodes a therapeutic molecule for treating a disease of the eye, wherein the expression vector expresses high-levels of the therapeutic molecule when administered to the eye of an individual, and wherein the expression vector comprises nucleic acid sequences that direct packaging of the expression vector. In one embodiment, the expression vector comprises one or more AAV ITRs. In one embodiment, the step of contacting the expression vector with a packaging system comprises introducing the expression vector into a cell. Methods of introducing nucleic acid molecules into cells are known in the art and include, for example, transfection and electroporation. In one embodiment, the expression vector is introduced into a cell expressing one or more AAV proteins. In one embodiment, the cell expressing one or more AAV proteins is a recombinant protein engineered to express an AAV Rep protein, an AAV capsid protein, or both the Rep protein and a capsid protein. Packaging functions may also be provided by a helper virus. Thus, in one embodiment, the expressing vector is introduced into a cell that is also infected with a helper virus.

The present invention also provides therapeutic compositions comprising expression vectors of the present invention. Such compositions comprise expression vectors in physiologically acceptable solutions that comprise, for example, water, saline, salts, buffer, diluents, stabilizing agents, polymers, chelating agents and the like. One example of a physiologically acceptable solution is a solution comprising about 10 mM Tris-HCl (pH 7.4) and about 180 mM NaCl. A further example of a suitable solution is a solution that comprises about 310 mM Tris-HCl (pH 7.4), about 180 mM NaCl, and about 0.001% Pluronic F-68. In a preferred embodiment, a composition of the present invention comprises a solution comprising about 10 mM NaPhosphate (pH 7.3), about 180 mM NaCl, and about 0.001% Pluronic F-68. It will be appreciated by those skilled in the art that such concentrations are approximate and may vary by as much as 10% or more, without significant affect on the efficacy of the composition.

The present invention also provides kits for practicing the disclosed methods. Kits of the present invention may comprise expression vectors of the present invention and viral vectors of the present invention. Such kits may also comprise reagents and tools necessary for practicing the disclosed methods such as, for example, buffers, diluents, syringes, needles and instructions for administering such reagents. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

EXAMPLES

These Examples demonstrates the ability of an AAV vector expressing the human retinoschisin protein (SEQ ID NO:2) to preserve retinal function in a mouse model of retinoschisis.

Example 1

A study was conducted to evaluate the ability of the proposed clinical adeno-associated virus (AAV) retinoschisin vector, AAV8 scRS/IRBP hRS, to preserve retinal function and structure, and to mediate retinoschisin protein expression when administered intravitreally to the retinoschisin deficient Rs1-KO mouse. AAV8 scRS/IRBP hRS vector at doses of 1.0e6, 1.0e7, 5.0e7, 1.0e8, 5.0e8 and 2.5e9 vg/eye, or vehicle, were administered by intravitreal injection to 18-34 day old Rs1-KO mice. The contralateral eye was not injected. Corneal electroretinogram (ERG) a-wave and b-wave amplitudes were measured at 11 to 15 weeks and 6 to 9 months post injection (PI), retinal cavity formation was measured by optical coherence tomography (OCT) at 12 to 16 weeks PI, and retinoschisin protein expression was measured by immunohistochemistry at 12 to 18 weeks and 6 to 9 months PI. ERG and OCT are used clinically as indicators of retinal function and structure, respectively. At 11-15 weeks PI, eyes receiving doses of $5e^7$, $1e^8$ and $2.5e^9$ vg/eye showed statistically-significant improvement in ERG a-wave amplitudes, and doses of $5e^7$, $1e^8$, $5e^8$, and $2.5e^9$ vg/eye showed statistically significant improvement in ERG b-wave amplitudes compared to uninjected eyes. Three vector doses were tested at the 6-9 month time point, $1e^8$, $5e^8$ and $2.5e^9$ vg/eye, and all produced statistically significant improvement in ERG a- and b-wave amplitudes compared to uninjected eyes. Retinal cavities, as measured by OCT at 11-15 weeks PI, were also significantly reduced at doses of $5e^7$, $1e^8$, 5e8 and $2.5e^9$ vg/eye compared to untreated eyes. Retinal immunohistochemistry indicated that significant retinoschisin protein levels were produced at doses of $1e^7$, $1e^8$, $5e^8$, and $2.5e^9$ vg/eye, compared to untreated eye at 11-15 weeks PI. Doses of $1e^8$, $5e^8$ and $2.5e^9$ produced expression at 25% of wild type mice or greater. At 6-9 months PI, only the $2.5e^9$ vg/eye dose was tested, and it produced 65% of the wild type retinoschisin level, a significant increase over 11-15 weeks. These data demonstrate that AAV8 scRS/IRBP hRS shows efficacy at 10- to 100-fold lower doses than the previously presented vector AAV8 hRSp4. AAV8 scRS/IRBP hRS was developed by examination of several retinoschisin vectors for efficacy in the mouse retinoschisis model, and for toxicity in rabbits.

As noted above, this study examined the ability of AAV8 scRS/IRBP hRS vector to preserve retinal function and retinal structure and to mediate retinoschisin protein expression when administered intravitreally to the retinoschisin deficient Rs1-KO mouse. The Rs1-KO mouse is a retinoschisin knockout model of X-linked retinoschisis, that exhibits structural and functional changes characteristic of the human disease including a much reduced b-wave relative to the a-wave, and the presence of schisis or splitting of the inner nuclear and outer plexiform layers. In this study, vehicle or AAV8 scRS/IRBP hRS vector at doses of 1.0e6, 1.0e7, 5.0e7, 1.0e8, 5.0e8 and 2.5e9 vg/eye were administered by intravitreal injection to 18-34 day old Rs1-KO mice. Although a very crude estimation, mice of this age correspond roughly to the age of the patient population that might benefit most from a successful therapy (adolescents and young adults). The mice were then evaluated by ERG for retinal function, OCT for retinal structure and immunohistochemistry for retinoschisin expression at 11-15 weeks and 6-9 months PI.

The experiments disclosed herein were also designed to determine the dosage range over which this vector significantly preserves retinal function and structure in the Rs1-KO mouse and achieves significant retinal expression of protein.

Description of the Viral Vector Used in this Example

The vector used in this Example, AAV8 scRS/IRBP hRS, is an adeno-associated virus type 8 vector that delivers a self-complementary vector genome composed of a modified human retinoschisin promoter that drives the expression of a human retinoschisin cDNA. This vector also employs an interphotoreceptor retinoid-binding protein (IRBP) enhancer to augment promoter activity, a truncated retinoschisin first intron, and a human beta-globin 3' untranslated region and polyadenylation site. The structure of AAV8 scRS/IRBP hRS is shown in FIG. 1 and the complete sequence of the vector is provided as SEQ ID NO: 16.

Structure of pAAV scRS/IRBP hRS Vector Production Plasmid

The production plasmid for the AAV8 scRS/IRBP hRS vector, called pAAV scRS/IRBP hRS, is composed of the human retinoschisin expression cassette described above, bounded by AAV2 inverted terminal repeat sequences, that has been cloned into a pBluescript plasmid (Stratagene Inc., San Diego, Calif.).

Construction of the pAAV scRS/IRBP hRS Vector Production Plasmid

Retinoschisin expression cassette: The protein coding portion of the expression cassette is composed of a human retinoschisin cDNA that retains a 319 bp, truncated retinoschisin first intron. The truncated intron consists of base pairs +95 to +355 and +14396 to +14445 relative to the retinoschisin transcriptional start site. These sequences encode the splice donor and lariate/splice acceptor elements, respectively. An 8-base pair AsiSI restriction site was introduced between the two parts of the intron to facilitate vector construction. Transcription of the expression cassette is driven by the human retinoschisin genomic sequence that extends from position −739 relative to the transcription start site, to position +42, which is the base that precedes the start codon. This promoter sequence contains a 308 bp Alu repeat sequence at positions −496 to −188, which has been deleted and replaced with a 261 bp enhancer from the human IRBP gene, which was flanked by SalI sites. The IRBP enhancer is located at position −1374 to −1635 relative to the IRBP transcriptional start site. Polyadenylation is directed by a 218 bp fragment encoding the entire human beta-globin 3' untranslated region and polyadenylation site. This region corresponds to the 218 bp genomic sequence that directly follows the human beta-globin stop codon. Synthetic DNA encoding XhoI and BglII sites was introduced between the retinoschisin stop codon, and the beta globin sequences that encode the 3' untranslated and polyadenylation site, to facilitate construction. A NotI site and an AscI site were added to the 5' and 3' ends of the expression cassette, respectively, in order to ligate it to the 5' and 3' AAV2 inverted terminal repeat elements.

AAV inverted terminal repeat sequences: The ITRs used in this construct are not identical. The 5' ITR was derived from psub201. ITRs derived from psub201 have a 15-base pair deletion of the ITR sequence in the A region of the palindrome which is not proximal to the transgene. Consequently, they are 130 bps in length rather than the wild type length of 145 bp. The 5' ITR was further modified by removal of the "D region" which contains the rep nicking site. To do this, the MscI site located near the inside border of the ITR palindrome was cleaved with MscI and a poly linker encoding SmaI (half site)-BamHI-SpeO-XbaI-NotI was ligated to it, in place of the D region. This modified ITR allows production of self-complementary AAV vector genomes. A PacI site was also added to the outside (not proximal to transgene) of the ITR. The 3' ITR is a full length, 145 bp ITR and was produced by nucleic acid synthesis (Blue Heron, Bothell, Wash.). It is flanked in the inside (proximal to transgene) by an AscI site and an FseI site on the outside. The ITRs are linked to the expression cassette through the NotI (5') and AsiSI (3') sites and to the pBluescript plasmid backbone through PacI (5') and FseI (3') sites. The promoter of the expression cassette is proximal to the 5' ITR.

pBluescript plasmid backbone: The pBluescript S/K+ plasmid was modified for use as an AAV vector plasmid backbone. The sequence between the AflIII and BstUI (partial) sites located at positions 457 and 1150 in the plasmid were removed and replaced with synthetic DNA encoding the restriction sites SseI-PvuII-SseI-AflII. This poly linker was further modified by ligating a poly linker encoding restriction sites SseI-PspXI-PmlI-PvuII-SseI between the two SseI sites of the first polylinker. Finally, the ITR-flanked AAV vector was excised from the pUC18 used for its construction using by cutting with PspXI and SapI (blunt) and was ligated between the PspXI and PvuII sites of the polylinker above to create the pAAV scRS/IRBP hRS production plasmid.

Construction of the Viral Vector

The AAV8 scRS/IRBP hRS vectors were prepared as previously described (Grimm D et al. 2003). Briefly, 293 cells cultured in 850 cm$^2$ roller bottles in DME (High Glucose) media containing 10% fetal bovine serum (Hy-Clone SH30070.03) and supplemented with penicillin, streptomycin and glutamine were transiently transfected with the helper plasmids pLadeno5 (encoding adenovirus type 2 E2A, E4, and VA RNAs) and pHLP19-8 (encoding AAV2 rep and AAV8 cap), and the pAAV scRS/IRBP hRS vector plasmid using the calcium phosphate method. After transfection, the media was changed and replaced with the same media lacking serum. Sixty hours later, the cells were collected by centrifugation and stored at −80 C. To purify the viral vectors, the cell pellets were thawed, suspended in 50 mM Tris-HCl, 150 mM NaCl, 2 mM MgCl$_2$, pH 8.0 and disrupted by 3 rounds of microfluidization. The cell debris was removed by centrifugation and the supernatant was adjusted to 25 mM CaCl$_2$ and the resulting pellet was also removed by centrifugation. Benzonase nuclease was added to the supernatant to a final concentration of 100 units per ml and the mixture was incubated for 1 hour at 37 C. 40% polyethylene glycol 8000 (PEG)/2.5 M NaCl was then added to produce final concentrations of 8% PEG and 0.650 M NaCl and the vector fraction was precipitated and collected by centrifugation. The vector fraction was solubilized in 50 mM HEPES, 150 mM NaCl, 20 mM EDTA, 1% sodium lauroyl sarcosinate, 10 µg/ml RNase A, pH8.0. This solution applied to a CsCl step gradient and vector was separated from the bulk protein and nucleic acids by ultracentrifugation. The vector fraction was collected and applied to a linear CsCl gradient and repurified. The purified vector fraction was collected, dialyzed against 10 mM Tris-Cl, 180 mM NaCl pH 7.4, formulated in 310 mM Tris-Cl, 180 mM NaCl, 0.001% Pluronic F-68 pH 7.4, filter sterilized, and stored at −80 C.

Analysis of the Purified pAAV scRS/IRBP hRS Vector

Figure 2:
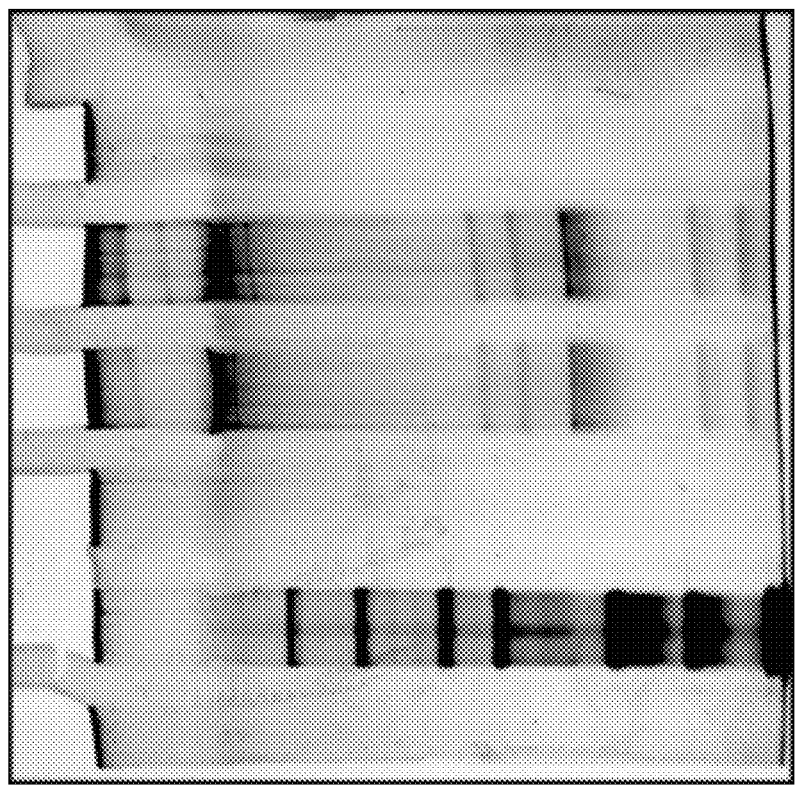
FIG. 2 shows the AAV8 hRS/IRBP and AAV8 hRSp4 vectors evaluated on Coomassie R250 (panel A) and silver stained (panel B) 7.5% SDS gels. Sample order:
left panel (Coomassie): Standard, AAV8 hRS/IRBP, AAV8 hRSp4, Standard;
right panel (silver): Standard, AAV8 hRS/IRBP, AAV8 hRSp4.
All vector loaded at 2e10 vg/lane. Standards are (from the top): 250 kd, 150 kd, 100 kd, 75 kd, 50 kd, 37 kd, and 25 kd.
Figure 2:
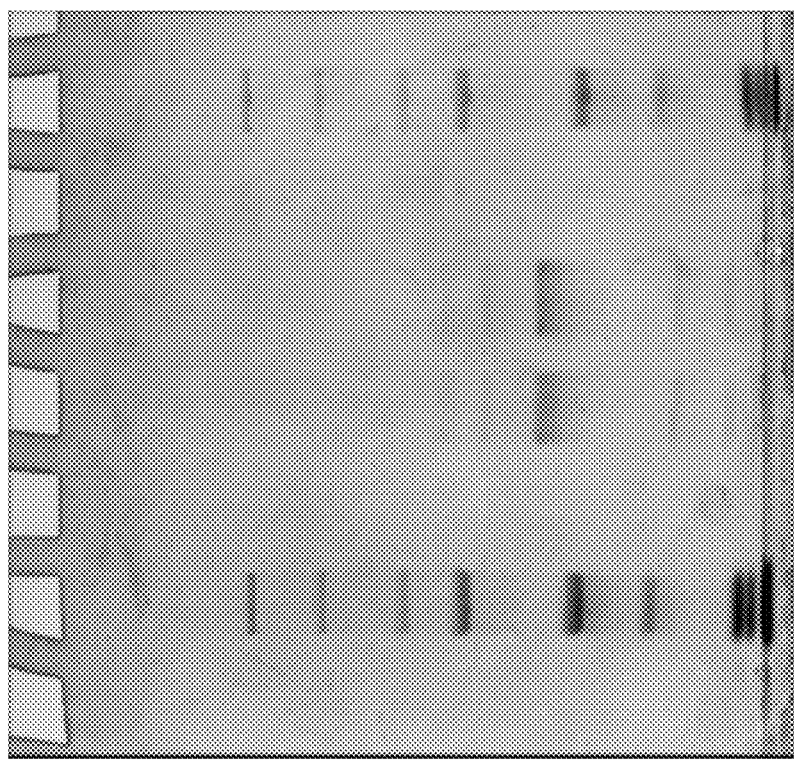

The purified vector particles were analyzed by Q-PCR Protein assay (BCA), SDS PAGE, Endotoxin assay (type) and Dynamic Light Scattering. Q-PRC assay was performed using the Taqman Real-Time PCR assay with upstream and downstream primers located in retinoschisin exons 3 and 4, respectively, and a probe that spanned the exon 3/4 junction. The level of protein present was determined by the Bradford method using bovine gamma-globulin as the standard (Rio-Rad, Richmond, Calif.). The theoretical protein concentration was calculated as the mass of AAV capsid protein/ml, based on the Q-PCR result. SDS PAGE analysis was conducted on 1.2e10 vg (prep 1) and 2e10 vg (prep 2) using 7.5% SDS gels. Visualizataion of the separated proteins was done by staining the gels with Coomassie R250 or a silver staining. The Kinetic LAL endotoxin assay was performed using a Kinetic Chromogenic Limulus Amoebocyte Lyasate Endotoxin Assay Kit (Clonegen Laboratories). The Dynamic Light Scattering Assay was performed using a Viscotec 802 DLS instrument, with vector concentrations of 2.25e12 vg/ml and 5e12 vg/ml for the AAV8 hRSp4 and AAV8 hRS/IRBP vectors, respectively. The results of this analysis are shown in FIG. 2 and tabulated as follows:

Analysis Results for AAV8 scRS/IRBP hRS Vector

|  | Prep 1 | Prep2 | Vehicle |
|---|---|---|---|
| Vector genomes/ml | $2^{12}$ | $2^{12}$ | |
| Protein/ml (ug/ml) | Not Detectable | 26 | |
| Theoretical protein/ml | 18 | 18 | |
| Endotoxin units/ml | Not detectable | 12 | 0.174 |
| SDS PAGE | Prominent capsid band at 25 kd. Two minor bands below Staining also above 25 kd and in well | | |
| Dynamic Light Scattering | Major symmetrical peak at 15-16 nm for both; No other significant peaks | | |

Dosage Preparation and Administration

Under a dissecting microscope, one microliter (µl) of vector or vehicle was administered to the right or left eye by intravitreal injection using 10 µl Nanofil syringes (World Precision Instruments, Inc., Sarasota, Fla.) and removable 35 gauge needle. Injected material was sterilized by passage through a 0.22 µl filter, and the syringes were loaded under aseptic conditions. Mice were anesthetized with IP ketamine, 80 mg/kg, and xylazine, 4 mg/kg, and one drop of 0.5% tetracaine was applied topically on the cornea. One microliter of vector or vehicle solution was injected through the pars plana in the superior nasal quadrant approximately 1 mm posterior to the limbus in one eye of each mouse. The injection volume is approximately one-fifth of the total vitreous volume. The injection was performed such that the needle tip was positioned in the center of the vitreous before the vector was delivered at a slow rate. The needle was then carefully extracted from the eye, and triple antibiotic ophthalmic ointment (neomycin, polymixin B and bacitracin) was applied to the injection site. The mice were placed onto a warming plate (35 C to 37 C) until they recovered from the anesthesia and were then put back into their cage.

Test System

The retinoschisin knockout (Rs1-KO) mouse model was generated in 2003. Since November 2003, these mice have been housed at NIH in a shared animal facility maintained by the National Institute of Allergy and Infectious Diseases (NIAID) and backcrossed more than 18 generations onto the C57BL/6J line (Jackson Laboratory, Bar Harbor, Me.). The Rs1-KO mice were 18 to 34 days at injection and 14 to 37 weeks at ERG, and confirmed to lack retinoschisin expression in the retina and have a retinal structural and functional phenotype similar to that of XLRS patients, including a reduced b-wave amplitude relative to the a-wave amplitude, and the presence of "schisis" cavities involving splitting or separations within the outer plexiform (OPL) and inner nuclear layers (INL).

Dosing: 28 mice received 2.5e9 vg/eye. 41 mice received 5.0e8 vg/eye. 39 mice received 1.0e8 vg/eye. 26 mice received 5.0e7 vg/eye. 26 mice received 1.0e7 vg/eye. 26 mice received 1.0e6 vg/eye. 43 mice received injection vehicle.

The study included 229 male Rs1-KO mice. The retinoschisin vector was administered unilaterally to 186 Rs1-KO, and the contralateral eye was not injected. The mice came from 60 litters which were the offspring of 26 different homozygous and 6 heterozygous female Rs1-KO mice crossed with C57BL/6J males. Vehicle was administered unilaterally to 43 male Rs1-KO mice, and the contralateral eye was not injected. These mice came from 15 litters that were the offspring of 13 different homozygous female Rs1-KO mice crossed with C57BL/6J male mice. As homozygous Rs1-KO females produce only Rs1-KO males it was not necessary to check the genotype of these males, but several males from this mating scheme were randomly picked to confirm the genotype. The genotypes of all heterozygous females and their offspring were confirmed by genotyping.

Experimental Procedure

A listing of all mice used in this study, their parents, the test material they received, and their dates of birth, injection, ERG, OCT, and histological examination/sacrifice was compiled and recorded.

Injections

One microliter of AAV8 RS/IRBP hRS vector solution was administered unilaterally by intravitreal injection on postnatal day (p) 18-25 (21±2 days, mean±1SD) to Rs-1KO mice under aseptic conditions. Control Rs-1KO mice received unilateral, intravitreal injections of 1 µl of vehicle at 18-34 PND (24±5 days). One microliter of AAV8 hRS1/IRBP or vehicle were administered to 229 Rs1-KO mice: 2.5e9 vg/eye, 28 mice; 5.0e8 vg/eye, 41 mice; 1.0e8 vg/eye, 39 mice; 5.0e7 vg/eye, 26 mice; 1.0e7 vg/eye, 26 mice; 1.0e6 vg/eye, 26 mice; vehicle, 43 mice. Ocular changes, such as corneal opacity, and the amount of reflux from the injection site, were noted for each animal during or immediately following injection. The injections of all 186 vector injected animals were successful, but 2 mice (1.1%) died after injection while still anesthetized.

Three vector injected mice had to be euthanized before the ERG was completed: 2 mice were sacrificed within 3 days of injection because they were thought too small to survive; 1 mouse (0.5%) had to be sacrificed before ERG recording due to malocclusion, a problem with excessive tooth growth that occurs in 0.05-0.09% of C57BL mice depending on substrain. One vehicle injected animal (2.3%) was sacrifice before the ERG because of malocclusion and one animal was sacrificed because of an occluded eye. Twenty-five vector injected animals (13%) died during or after anesthesia for ERG or OCT. Two vehicle injected animals (4.6%) died after the ERG was complete.

The injection of vector was not considered relevant to the deaths of animals prior to anesthesia for the ERG: 2 mice that died before recovering from injection anesthesia, 2 mice sacrificed immediately for small size, and one mouse sacrificed for malocclusion. Overall, 25 animals in the vector injected group died during or after anesthesia for the ERG or OCT, but the number of deaths is not statistically greater than in the vehicle injected control group (P=0.18, Fisher's exact test) and did not show a significant trend with dose (P=0.72, Chi-square test for trend).

One-third of the deaths in the vector injected group occurred in the cohort receiving the dose of 1e6 vg/eye, and when each dose was compared separately to vehicle, only this dose was statistically greater than vehicle (P=0.005). As this was the lowest dose, these deaths may reflect preexisting condition of the animals or technical manipulation rather the effect of vector.

Electroretinogram (ERG)

ERG recording procedure: To evaluate the efficacy of the retinoschisin vector AAV8 scRS/IRBP hRS in preserving retinal function in Rs1-KO mice, the dark adapted electroretinogram (ERG) was recorded in both eyes simultaneously between 11 and 15 weeks after intravitreal injection of vector ("short term"), and/or between 6 and 9 months after intravitreal injection of vector ("long term"). Vehicle control mice were recorded between 14 and 18 weeks after intravitreal injection.

The day before recordings, mice were moved from the animal facility to the lab for overnight dark adaption in a light tight ventilated box. All subsequent procedures were performed in dim red light or darkness. After anesthesia with 80 mg/kg ketamine and 4 mg/kg xylazine given by intraperitoneal injection, the pupils were dilated with topical 0.5% tropicamide and 0.5% phenylephrine HCL, and the mouse was placed on a heating pad at 37° C. One percent proparacaine topical anesthesia was put on the cornea before placing gold wire loop active and reference electrodes in the center of the cornea and on the edge of the sclera, respectively. Recordings were the average of 1 to 20 dark-adapted responses to 10 µs flashes presented in 0.5 log unit intensity steps from −6.9 to +0.6 log cd·s/m$^2$ in a Ganzfeld (full field) bowl. The intensities to elicit these responses in mouse are similar to those in human. The main difference is that only about 3% of mouse photoreceptors are cones, compared to 5% for humans, therefore the relative contributions from cone photoreceptors is much less at the maximum intensity eliciting a mixed rod-cone response. Total time for each recording was about 20 minutes, and following recording, mice were allowed to recover on a heating pad before being replaced in cages.

The ERG signals were amplified 5000 times and filtered by a 0.1 to 1 kHz 3 db/decade bandpass and a 60 Hz line filter using a Grass CP511 AC amplifier before being digitized with a National Instruments AD board at 5 kHz. One to 20 waveforms were collected and averaged at each intensity, with smaller numbers collected at higher intensities.

ERG Data Analysis: ERG results reported in this study are a-wave and b-wave amplitude in response to a single stimulus intensity of 0.6 log cd·s/m$^2$. The dark-adapted a-wave reflects the activation phase of rod photoreceptors in response to light; the b-wave results from the response of bipolar cells which are activated transynaptically by photoreceptors. The vehicle group was used to control for possible effects of the injection procedure and was analyzed at the short term time point when maximum treatment effect of vector was expected.

Statistical procedures: Treated a-wave and b-wave amplitudes in vector and vehicle injected eyes were compared to a-wave and b-wave amplitudes in the untreated eyes at the short term time point and in the three highest dose vector injected groups at the long term time point using unpaired t tests corrected for multiple comparisons with the Holm-Sidak method assuming populations with the same standard deviation. All statistics were performed using Graphpad Prism 6.0. (GraphPad Prism version 6.00 for Windows).

Ocular Coherence Tomography (OCT)

The retinas of both eyes of all mice that received vector and survived the short term ERG and had unaltered ocular media were imaged in vivo by OCT from 2 to 21 days after the ERG. The numbers of mice imaged in each dose group include: 2.5e9 vg/eye, 25 Rs1-KO mice imaged; 5.0e8 vg/eye, 25 Rs1-KO mice imaged; 1.0e8 vg/eye, 20 Rs1-KO mice imaged; 5.0e7 vg/eye, 19 Rs1-KO mice imaged; 1.0e7 vg/eye, 25 Rs1-KO mice imaged; 1.0e6 vg/eye, 16 Rs1-KO mice imaged.

The OCT imaging system acquires, processes, displays and saves depth-resolved images of retinal tissue microstructure in vivo. We used the ultra-high resolution spectral domain OCT from Bioptigen, which allows noninvasive non-contact imaging providing microscopic tomographic images of the retina with 2 micron axial resolution. OCT imaging in XLRS patients has been demonstrated to be a useful tool in conjunction with functional measures to characterize retinal pathology. Mice were anesthetized (80 mg/kg ketamine and 4 mg/kg xylazine), mounted in a custom holder, and the optic nerve head of the retina was placed at the center of a rectangular scan area of 1.4 mm×1.4 mm (0.7 mm on each side of the optic nerve in the horizontal and vertical direction). This area was imaged with 1000 A-scans from the retinal pigment epithelium (RPE) to the posterior lens and 100 B-scans across the selected area at 2×2×2 micron voxels. Thus, approximately one third of the central retina of each mouse was imaged. In addition, images from other areas were regularly obtained to confirm that the central area was representative of the whole retina.

Figure 3:
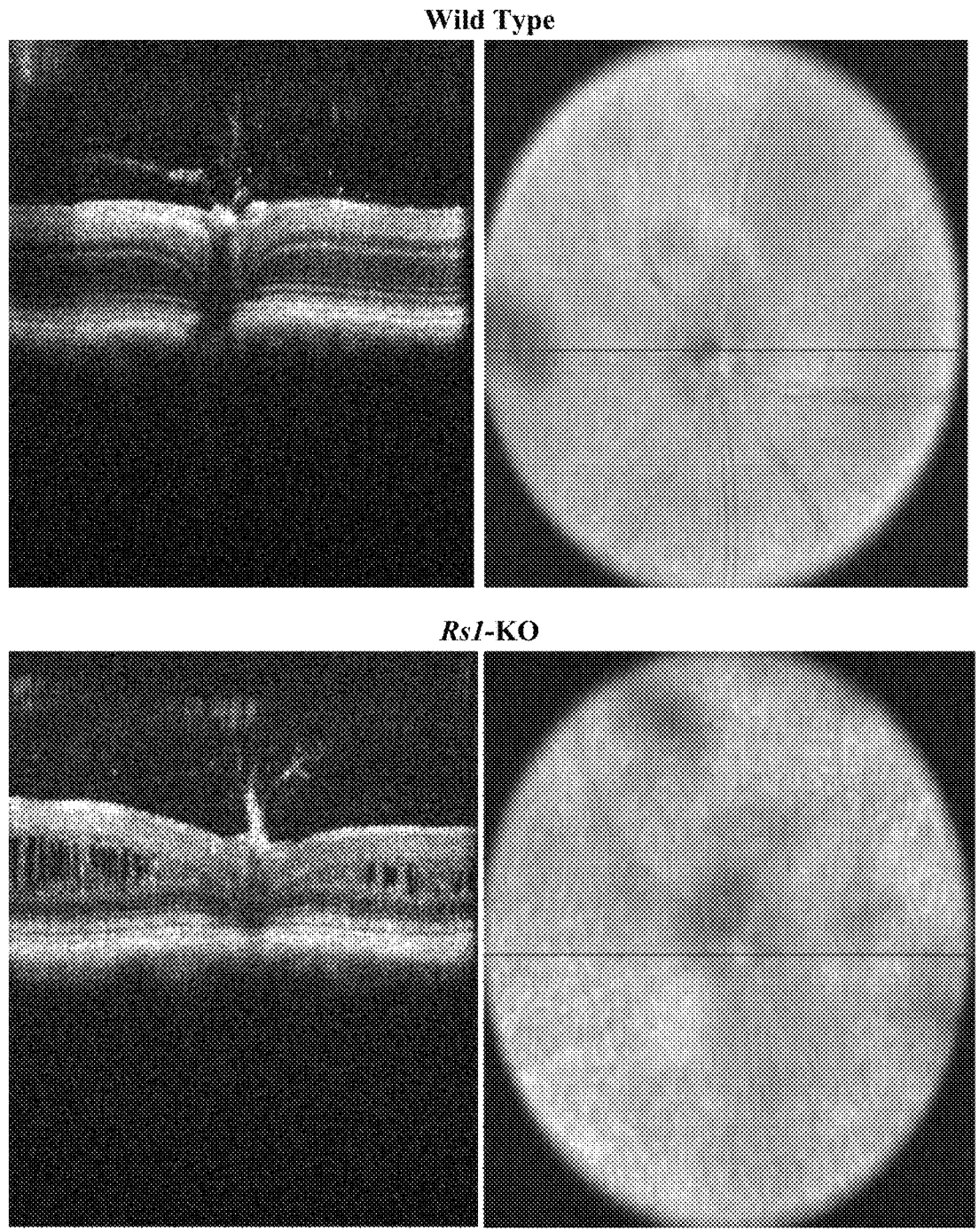
FIG. 3 shows OCT scans from a wild type and an Rs1-KO mouse showing a B-scan (left-hand images) taken through the central retina at the optic nerve as indicated by the central green line on the volume intensity projection (right-hand images) for each eye.

B scans through the rectangular scanned area are displayed as a series of retinal cross sections as would be seen in a light microscope when viewing histological sections taken horizontally through the retina (FIG. 3). The scans also provide an enface image of the whole area scanned (volume intensity projection) similar to fundoscopic images. Cavities consist of abnormal separations of retinal tissue between and within the outer plexiform (OPL) and inner nuclear layers (INL) (FIG. 3). Though the resolution is less than in microscopic images, the individual retinal layers and histopathology of Rs1-KO retinas can be easily distinguished. As imaged by OCT in mice, these cavities extended tens to hundreds of microns in radial length (optic nerve to periphery) and several microns to tens of microns in axial depth (across retinal thickness). They have an appearance very similar to that seen in fixed tissue under the microscope. In the volume intensity projections, the distribution of cavities within the scanned area is seen as patches of light and dark.

FIG. 3 shows OCT scans from a wild type and an Rs1-KO mouse showing a B-scan (left-hand images) taken through the central retina at the optic nerve as indicated by the central green line on the volume intensity projection (right-hand images) for each eye. The volume intensity projection is similar to a fundus photo imaging the surface of the retina from the front of the eye. The layers in the retina of the WT are well organized and distinct and the fundus has a smooth appearance and distinct retinal vessels. The B-scan of the Rs1-KO retina shows large areas of separations, called "schisis cavities," and the layers are less organized, less distinct and thinner. The fundus has a mottled appearance. Red asterisks indicate location of measurements of cavity width. Each measurement was graded on a scale of one to six, and the smallest and largest of these six measurements were averaged to produce a score for each retina.

The maximum height of these separations or "schisis cavities" in the inner nuclear layer of treated and untreated Rs1-KO retinas was measured along the B scans in four separate areas: one measurement 0.6 mm superior to the optic nerve, one measurement on the nasal and one on the temporal side of the midline scan through the optic nerve, and one measurement 0.6 mm inferior to the optic nerve as indicated by the red asterisks in FIG. 3 using an onscreen micrometer. The measurements were combined to generate a score for each retina as follows:

Data Collection

1. The central one-third of the retinal area was scanned by OCT for retinal cavities. Determination of the retinal area to be scanned was based on the following considerations:
    a. In a previously published study, we found that retinal pathology in the form of cavities was maximal in number and extent between 1 and 4 months of age and were distributed from optic nerve to periphery.
    b. Post injection times of 11 to 15 weeks in the present study, meant animals would be analyzed by OCT when untreated eyes of Rs1-KO mice would have maximal cavity number and distribution.
    c. Vector was injected in the center of the vitreous and assumed to distribute equally in all directions.
    d. The central one-third of the retina OCT imaged by a single rectangular scan in Rs1-KO mice was representative of the rest of the retina.
2. Linear scans were done at position A (+0.6 mm), B (0 mm or optic nerve), and C (−0.6 mm) (FIG. 3, Rs1-KO, right-hand image)

Cavity Grading

Three scans were performed: scan A and C at the most superior and inferior extent, respectively, were graded for maximum cavity height; scan C through the central retina was graded for maximum cavity height on each side of midline: total 4 values for each retina (asterisks in FIG. 3):
    a. No cavities=1
    b. Cavities<30 µm in height=2
    c. Cavities 30 to 49 µm in height=3
    d. Cavities 50 to 69 µm in height=4
    e. Cavities 70 to 99 µm in height=5
    f. Cavities≥100 µm in height=6

Scoring formula: Score=(maximum grade at position 1-4+minimum grade at position 1-4)/2.

Rs1 Protein Expression by Immunohistochemistry

The retinas of all animals that survived one or two ERG recordings were taken for retinal retinoschisin immunostaining to quantify retinoschisin expression.

From 1 to 21 days after the ERG or OCT the mice were euthanized and perfused with 4% paraformaldehyde in sodium phosphate buffer. The eyes were removed and fixed overnight in 4% paraformaldehyde and 0.5% glutaraldehyde in sodium phosphate buffer followed by processing for cryosectioning. Twenty-five sagittal sections of the injected eye were taken beginning at the nasal margin of the retina and proceeding through and including the optic nerve head and approximately 200 µm of the temporal retina. The sections were stained using a rabbit polyclonal antibody against the N-terminus of retinoschisin (amino acid residues 24-37) and a secondary antibody conjugated to red-fluorescent Alexa Fluor 568 dye (Invitrogen). Nuclei were stained with DAPI.

Figure 4A:
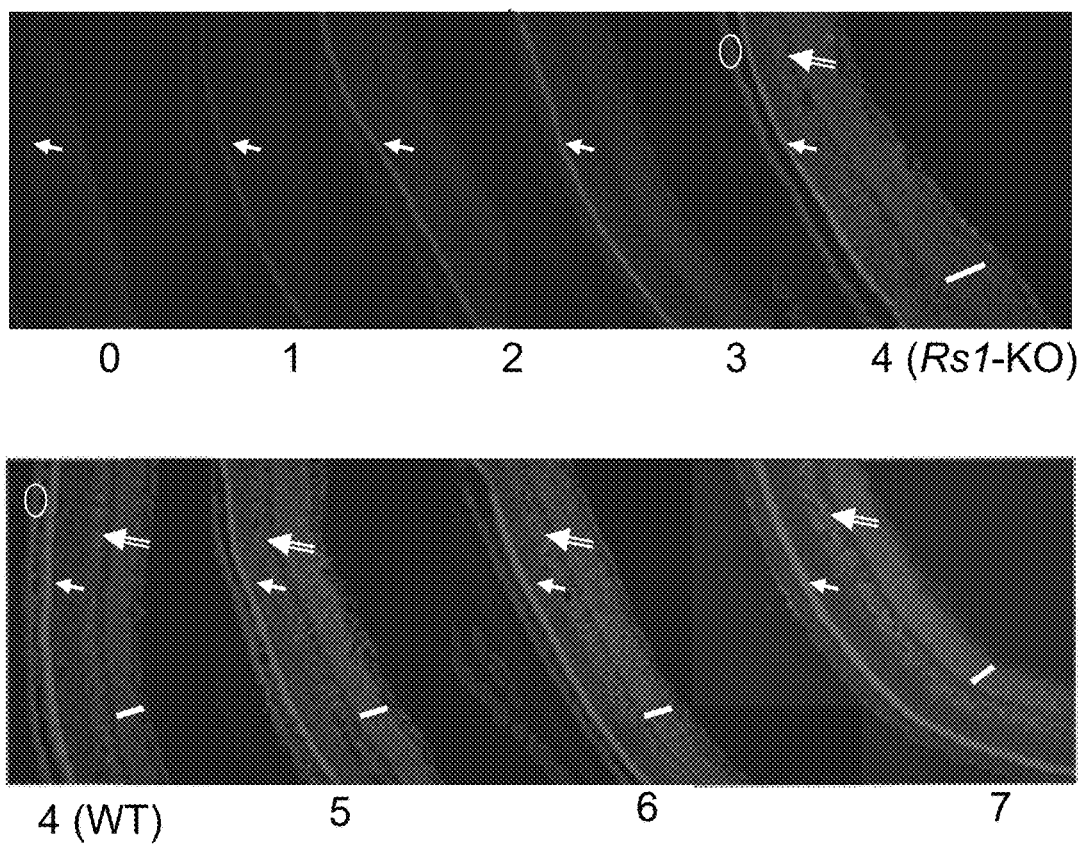
FIGS. 4A and 4B show the scoring of retinoschisin immunostaining in AAV8 scRS/IRBP hRS treated retinas of Rs1-KO mice.
Figure 4B:
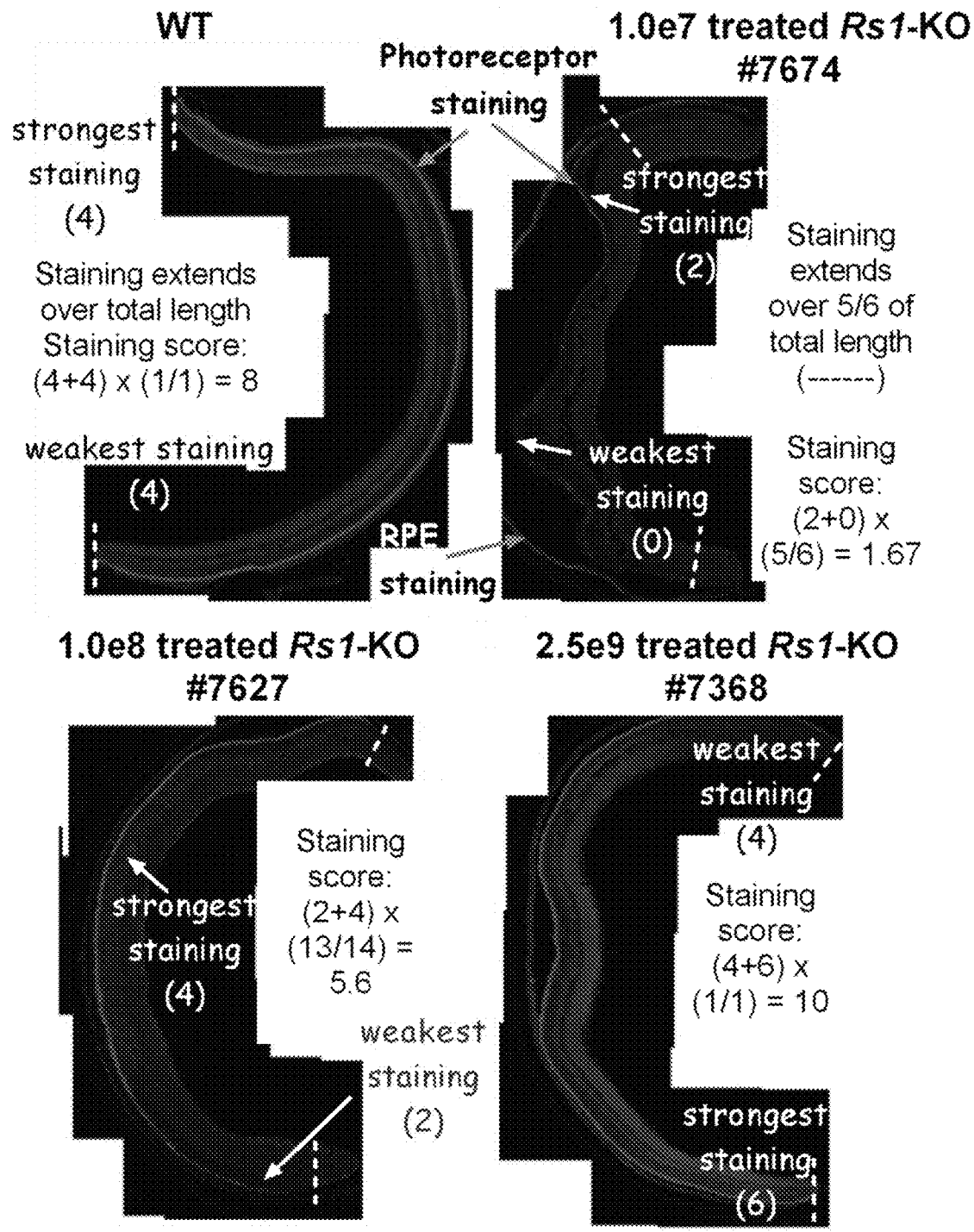

Retinoschisin expression in retinas of eyes receiving AAV8 scRS/IRBP hRS and untreated eyes was evaluated using a fluorescence microscope to determine the intensity and extent of immunostaining in 4 vertical sections taken at evenly spaced intervals from the nasal margin of the retina to the optic nerve and one section taken just temporal to the optic nerve. The results from these 5 sections were averaged. In each section from a vector treated Rs1-KO retina, stain intensity in the photoreceptor and inner retinal layers was evaluated in comparison to a WT retina stained at the same time to help control for variations in the level of background staining with each batch. WT intensity was assigned a value of 4, and Rs1-KO sections were graded from 0 to 7 as depicted in FIG. 4A. FIG. 4 shows the scoring of retinoschisin immunostaining in AAV8 scRS/IRBP hRS treated retinas of Rs1-KO mice. Retinoschisin protein was visualized by immunofluorescent labeling (red) in frozen retinal sections from wild type (WT) mice and Rs1-KO mice treated with AAV8 scRS/IRBP hRS by intravitreal injection. Retinas were processed 12 to 18 weeks after injection. Scoring of retinoschisin staining was done using intensity and distribution grading. FIG. 4A shows the intensity criteria for levels 0-7 are shown. Levels 0 through 4 could be graded on the basis of photoreceptor staining intensity only (solid white arrows) because photoreceptor staining was not saturated. At level 4 inner retinal staining is also seen. Level 4 staining in an Rs1-KO and WT retina are shown. Since photoreceptor staining approaches saturation at level 4, levels 5, 6 and 7 are graded on the basis of staining intensity and consistency in the inner nuclear (open white arrow) and inner plexiform (white bar) layers. An increase in brightness and/or more solid staining than the previous grade in either layer was used as criteria for the next highest grade. In grade 5 above, the IPL was stained more intensely than in grade 4; in grade 6, the IPL was similar to grade 5, but the INL was brighter than 5; in grade 7, the IPL was stained more solidly than in grade 6. Staining in the RPE layer (oval in Rs1-KO and WT #4) when present was ignored. FIG. 4B shows the method of combining staining intensity with distribution to obtain staining score. The proportion of the section stained was defined by the widest separation of stained tissue (not necessarily uninterrupted). The strongest and weakest staining grades within that length were added together and multiplied by the proportion of the sectioned stained to obtain the staining score. Examples are high levels of expression in retinas treated with three different doses of scAAV8/IRBP hRS.

Since retinoschisin staining was not uniformly distributed across the sections from most treated retinas, two scores for each section were used: one score was assigned to the weakest area, and another one was assigned to the strongest area. The lowest and highest grades in each retina were added together. If staining was consistent across the section, the grade was doubled. Sections from WT retinas were uniformly stained and so had an intensity grade of 8 (4+4). Since in many sections staining was limited to only a portion of the retinal length, the staining intensity grade was multiplied by the proportion of the retinal length over which staining was observed to obtain the final score (FIG. 4B). For example, if staining intensity in a section ranged from 1 to 8 but only ½ the retinal section had retinoschisin staining, the score would be (1+8)*½=4.5. Wild type retinas received a score of 8: (4+4)*1/1. None of the untreated eyes showed staining above non-specific background levels (a score of 0).

Immunostaining score formula: Score per section=(maximum staining grade in section [0-7]+minimum staining grade in section)×(proportion of entire length containing all staining). Score per eye=(Score for sections 1+2+3+4+5)/5.

Results

ERG, Oct and Retinoschisin Expression Analysis

In this study, vehicle or AAV8 scRS/IRBP hRS vector at doses of 1.0e6, 1.0e7, 5.0e7, 1.0e8, 5.0e8 and 2.5e9 vg/eye, were administered by intravitreal injection to 18-34 day old Rs1-KO mice. The mice were then evaluated by ERG for retinal function at 11-15 weeks and 6-9 months PI followed by OCT for retinal structure and immunohistochemistry for retinoschisin expression. These experiments were conducted to determine the dose range over which this vector significantly preserves retinal function and structure in the Rs1-KO mouse and achieves significant retinal expression of protein. FIGS. 5-9 show the ERG, OCT (retinal cavity) and retinoschisin expression data.

Figure 5:
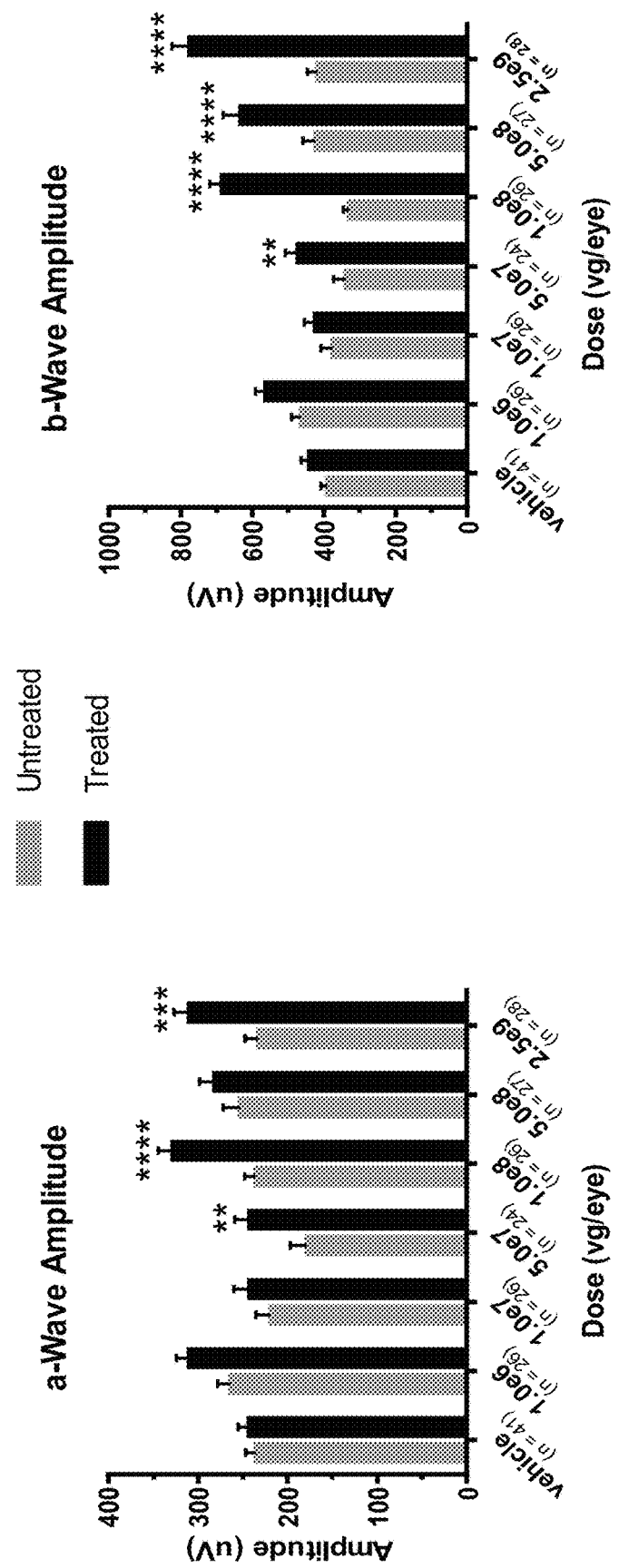
FIG. 5 shows the ERG a- and b-wave amplitudes of untreated eyes and eyes treated with intravitreal injections of vehicle or AAV8 scRS/IRBP hRS vector at various doses. The eyes were evaluated between 11 and 15 weeks post injection.

FIG. 5 shows the ERG a- and b-wave amplitudes of untreated eyes and eyes treated with intravitreal injections of vehicle or AAV8 scRS/IRBP hRS vector at doses of 1e6, 1e7, 5e7, 1e8, 5e8 and 2.5e9 vg/eye. 18-34 day old Rs-1KO mice received vehicle or AAV8 scRS/IRBP hRS vector in one eye by intravitreal injection at the doses indicated (expressed as vector genomes/eye). Amplitude values for a- and b-waves are shown and the group sizes are given below the dose. Two, 3 and 4 stars (*) indicate treated values that differ from untreated values, with P values <0.01, 0.001, and 0.0001, respectively, based on the unpaired t test corrected for multiple comparisons using the Holm-Sidak method. These eyes were evaluated between 11 and 15 weeks, post injection, a time period deemed "Short Term."

Figure 6:
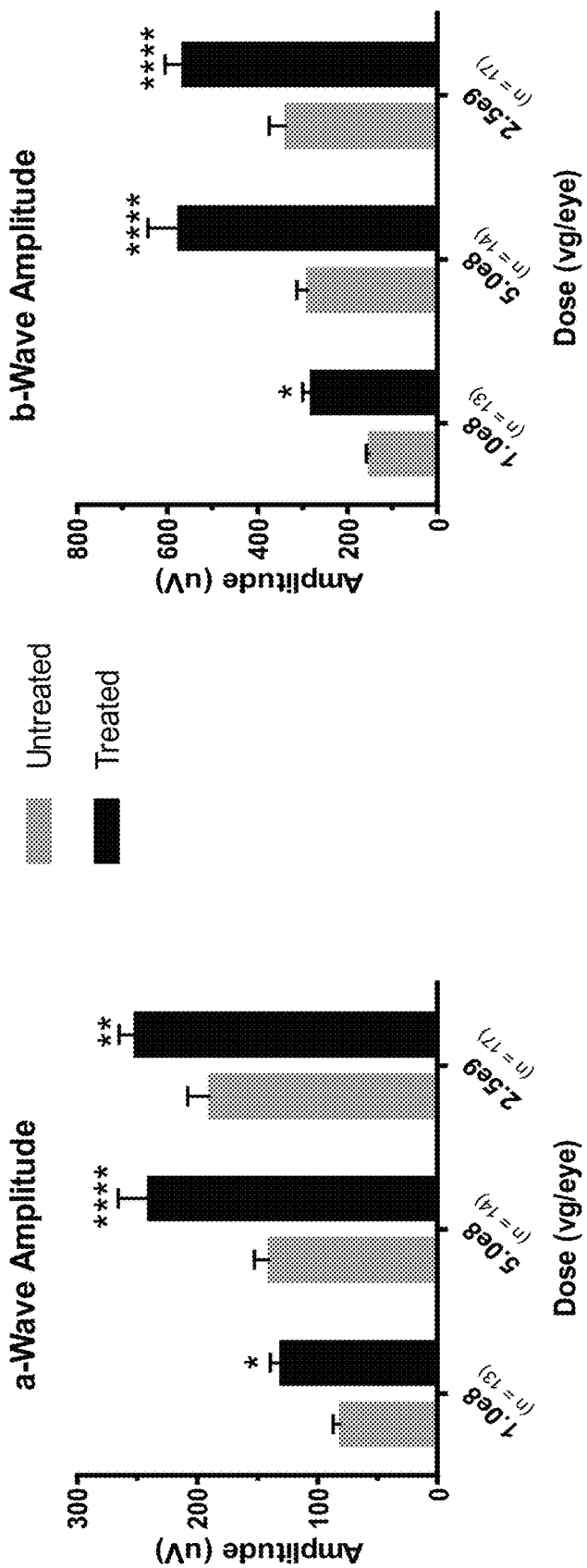
FIG. 6 shows the ERG a- and b-wave amplitudes in animals receiving 1e8, 5e8 and 2.5e9 vg/eye vector doses at 6-9 months post injection.

FIG. 6 shows the ERG a- and b-wave amplitudes in animals receiving 1e8, 5e8 and 2.5e9 vg/eye vector doses at 6-9 months post injection, a time period deemed "Long Term". This group is a subset of the animals evaluated at the Short Term time point in FIG. 5.

Figure 7:
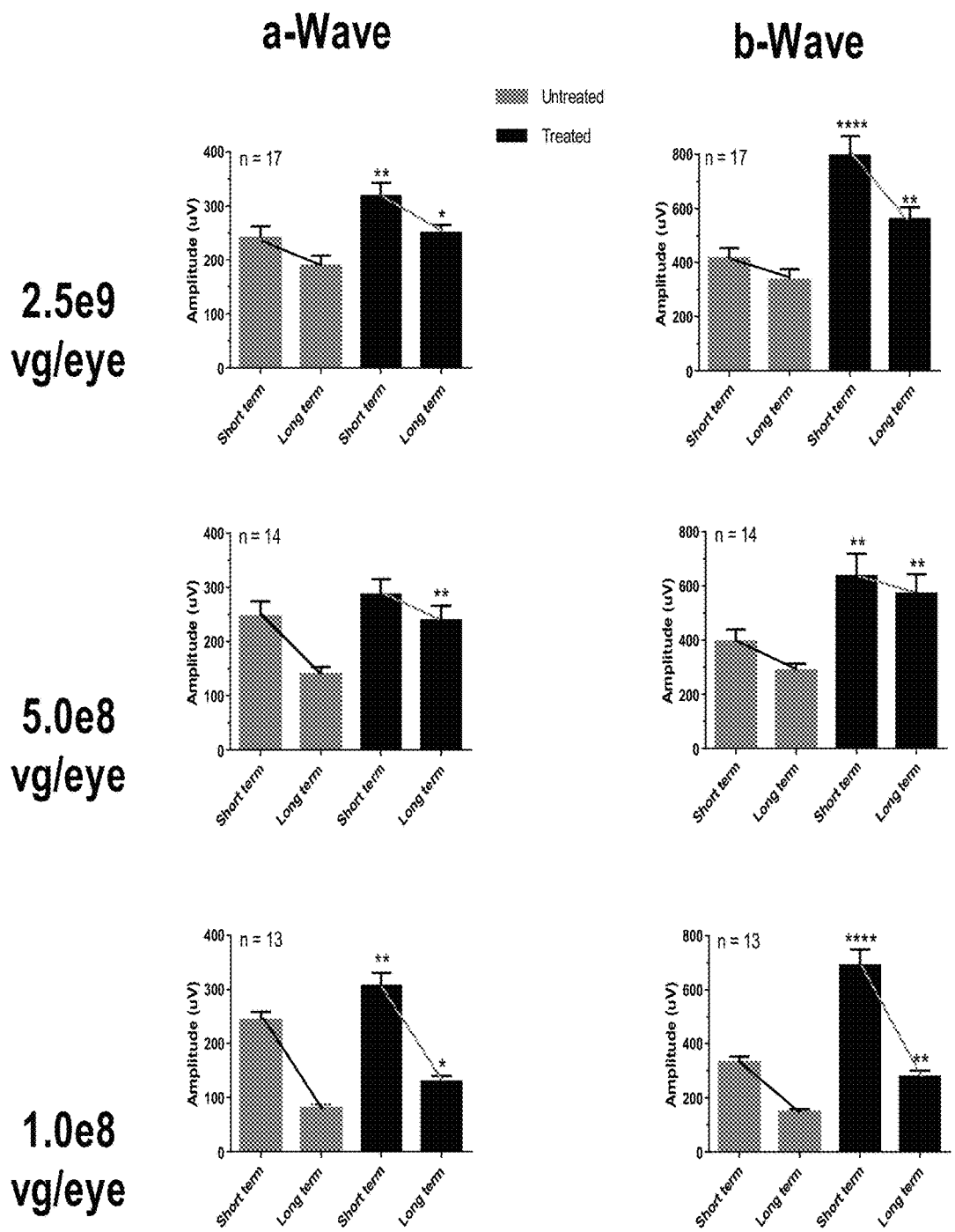
FIG. 7 presents a comparison of the Short Term and Long Term ERG results for treated and untreated eyes derived from the data sets shown in FIGS. 5 and 6.

FIG. 7 presents a comparison of the Short Term and Long Term ERG results for treated and untreated eyes at vector doses of 1e8, 5e8 and 2.5e9 vg/eye, so that persistence of treatment efficacy can be evaluated. This data is derived from the data sets in panels FIGS. 5 and 6. The lines at the top of the bars were drawn to allow the reader to better visualize the changes over time. One, 2, and 4 stars (*) indicate treated values that differ from untreated values, with P values <0.05, 0.01, and 0.0001, respectively, based on the unpaired t test corrected for multiple comparisons using the Holm-Sidak method.

Figure 8:
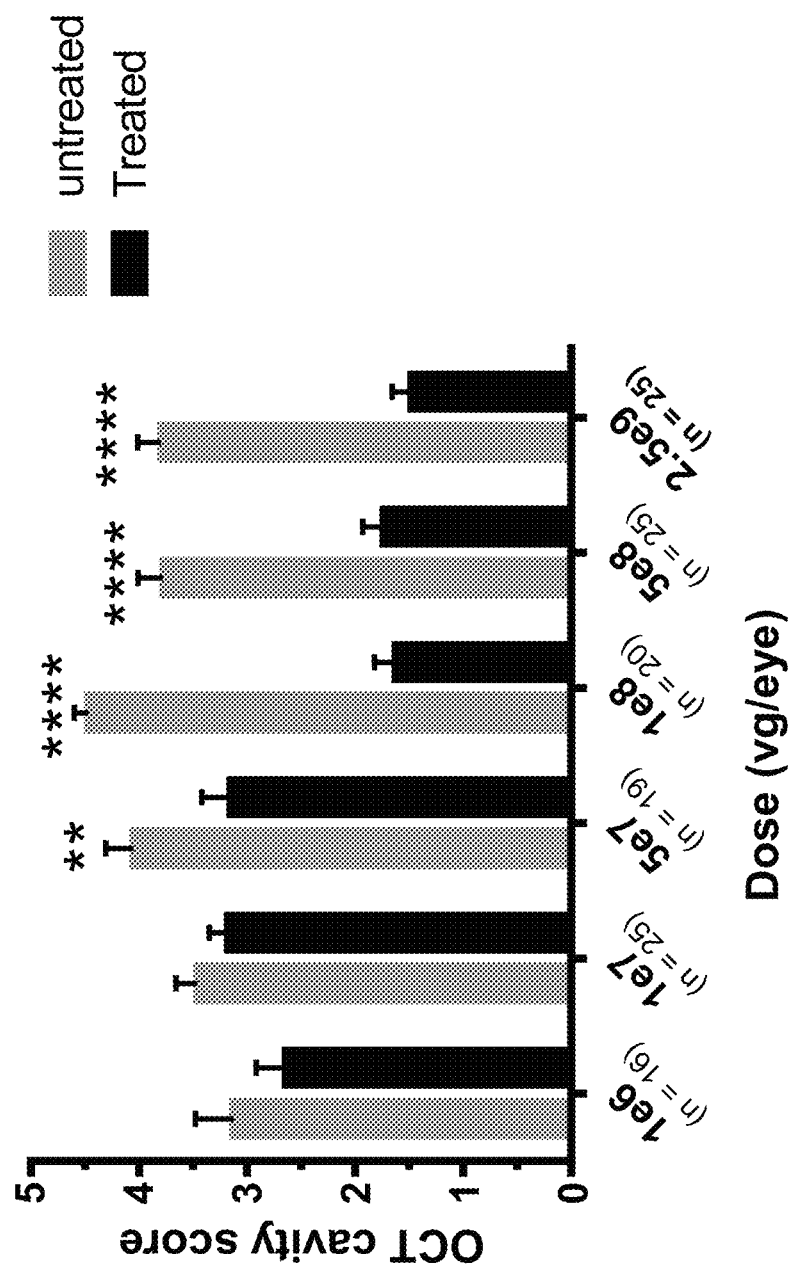
FIG. 8 shows the schisis cavity scoring averages in treated and untreated eyes from OCT images for various vector doses.

FIG. 8 shows the schisis cavity scoring averages in treated and untreated eyes from OCT images for vector doses of 1e6, 1e7, 5e7, 1e8, 5e8 and 2.5e9 vg/eye. The mice were evaluated at the Short Term time point (11-15 weeks post-injection). The bar graph shows the average raw scores (±SEM) for treated and untreated retinas at each dose and statistical comparison of treated to untreated eye based on the unpaired t test corrected for multiple comparisons using the Holm-Sidak method. The mice were evaluated at the Short Term time point (11-15 weeks post-injection) directly after ERG recording (data in panel A). (P<0.01, **P<0.0001).

Figure 9:
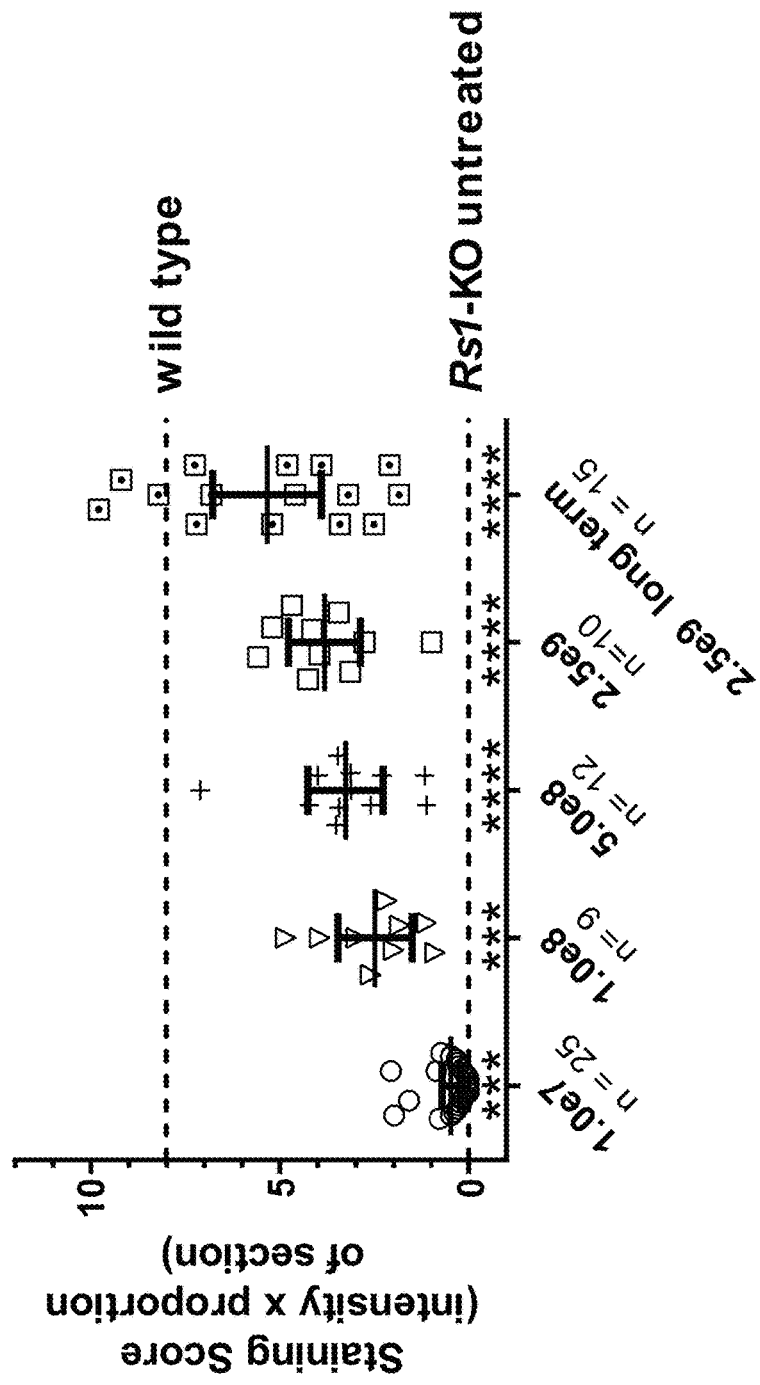
FIG. 9 depicts retinoschisin protein expression in response to vector doses between 1e7, and 2.5e9 vg/eye.

FIG. 9 depicts retinoschisin protein expression in response to vector doses between 1e7, 1e8, 5e8, and 2.5e9 vg/eye. The mice were examined at the Short Term time point (11-15 weeks, post injection). The 2.5e9 vg/eye dose was also evaluated at the Long Term time point (6-9 months, post-injection). Scatter plot shows values for each animal, the means and 95% confidence interval for each dose and statistical comparison to untreated eyes, by the one sample t test. (*P<0.001, **P<0.0001).

Conclusions

In this study, vehicle or AAV8 scRS/IRBP hRS vector at doses of 1.0e6, 1.0e7, 5.0e7, 1.0e8, 5.0e8 and 2.5e9 vg/eye, were administered by intravitreal injection to 18-34 day old Rs1-KO mice. The mice were then evaluated by ERG for retinal function at 11-15 weeks and 6-9 months PI followed by OCT for retinal structure and immunohistochemistry for retinoschisin expression. The experiments were designed to determine the dose range over which this vector significantly preserves retinal function and structure in the Rs1-KO mouse and achieves significant retinal expression of protein. From these experiments the following can be concluded:

1. AAV8 scRS/IRBP hRS vector doses of 5e7, 1e8 and 2.5e9 vg/eye showed statistically significant improvement in ERG a-wave amplitudes, and doses of 5e7, 1e8, 5e8, or 2.5e9 vg/eye showed statistically significant improvement in ERG b-wave amplitudes, compared to uninfected eyes, when recorded 11-15 weeks, post-injection (Short Term time point). Injection vehicle had no effect.
2. Vector doses of 1e8, 5e8 and 2.5e9 vg/eye produced statistically significant improvement in ERG a- and b-wave amplitudes compared to untreated eyes, when recorded 6-9 months, post injection (Long Term time point).
3. Vector doses of 5e7, 1e8, 5e8 and 2.5e9 vg/eye produce statistically significant improvement in schisis cavity scoring relative to untreated eyes when evaluated following the 11-15 weeks post-injection (Short Term time point).
4. Retinoschisin protein expression is significantly elevated in Rs-1/KO mouse eyes after vector treatment with doses of 1e7, 1e8, 5e8, and 2.5e9 vg/eye evaluated following the 11-15 weeks, post-injection (Short Term time point). At vector doses of 1e8 vg/eye and above, retinoschisin protein expression is greater than or equal to 25% of wild type levels. The Rs-1/KO eyes receiving the 2.5e9 vg/eye dose were evaluated at 6-9 months post-injection and showed 65% of the wild type retinoschisin level. This was the only dose evaluated at the Long Term time point.

Eyes of Rs-1/KO mice treated with AAV8 scRS/IRBP hRS vector doses between 1e8 and 2.5e9 vg/eye show statistically significant improvement in retinal function (by ERG) and retinal structure (by OCT) and express significant amounts of retinoschisin protein. When scaled to humans by retinal surface area (factor of 100), these doses are 1e10 to 2.5e11 vg/eye. In the accompanying Toxicity Report, rabbits treated intravitreally with AAV8 scRS/IRBP hRS vector at a dose of 2.5e10 vg/eye showed little toxicity at 4 months post injection.

Example 2

A study was conducted to assess the tolerability of expression vectors of the invention in rabbit eyes compared with control injections of vehicle alone. Briefly, thirty-nine New Zealand White rabbits (age 6-7 months at injection; weight 2.4-3.8 kg) were used in the present study. All in life procedures were conducted in compliance with the ARVO Statement for the Use of Animals in Ophthalmic and Vision Research and were approved by the Animal Care and use Committee of the National Eye Institute.

Vectors or vehicle were administered in the right eye by intravitreal injection using ½ cc Insulin Syringes with permanently attached 28 gauge needle (Ultrafine U-100 syringe—BD Biosciences, San Jose, Calif.) in an injection volume of 50 ul. Syringes were loaded under sterile conditions in a laminar flow hood on the day of injection. Rabbits were anesthetized with IM ketamine, 40 mg/kg, and xylazine, 3 mg/kg. Sterile surgical instruments were used and the animals were prepared aseptically prior to injection. Povidone iodine (5% povidone iodine, 95% BSS—irrigating solution) was used to disinfect the eyelid margins and eye lashes. BSS solution was used to wash the eyelids and for eye irrigation every 2 minutes to minimize corneal air exposure and consequent abrasion. An eyelid speculum was applied to avoid manipulating the eye and to avoid needle contact with lids and lashes. Fifty microliters of vector or vehicle solution were injected through the pars plana in the superior temporal quadrant approximately 2 mm posterior to the limbus in each eye. The injection was performed with the needle tip in the center of the vitreous and the vector was delivered at a moderately slow rate. The needle was then carefully extracted from the eye and a sterile cotton-tip applicator was applied to prevent reflux of both the vector and vitreous. Triple antibiotic ophthalmic ointment ("neo-poly-bac" for neomycin, polymixin and bacitracin) was applied to the injection site after injection, and the rabbits were returned to their cages.

All rabbits were clinically examined before injection, at 14 days and 1, 2 and 3 months after injection. Each rabbit underwent external ocular inspection and full ocular examination by slit lamp biomicroscopy (anterior segment) and by indirect ophthalmoscope (posterior segment) after pupillary dilation (one drop—twice, 10 minutes apart of topical Atropine 1% in both the eyes). Clinical changes were graded using a 5-step severity scale (none, trace, +1, +2, +3) by two examiners who were blinded to the nature or dose of the treatment.

Figure 10A:
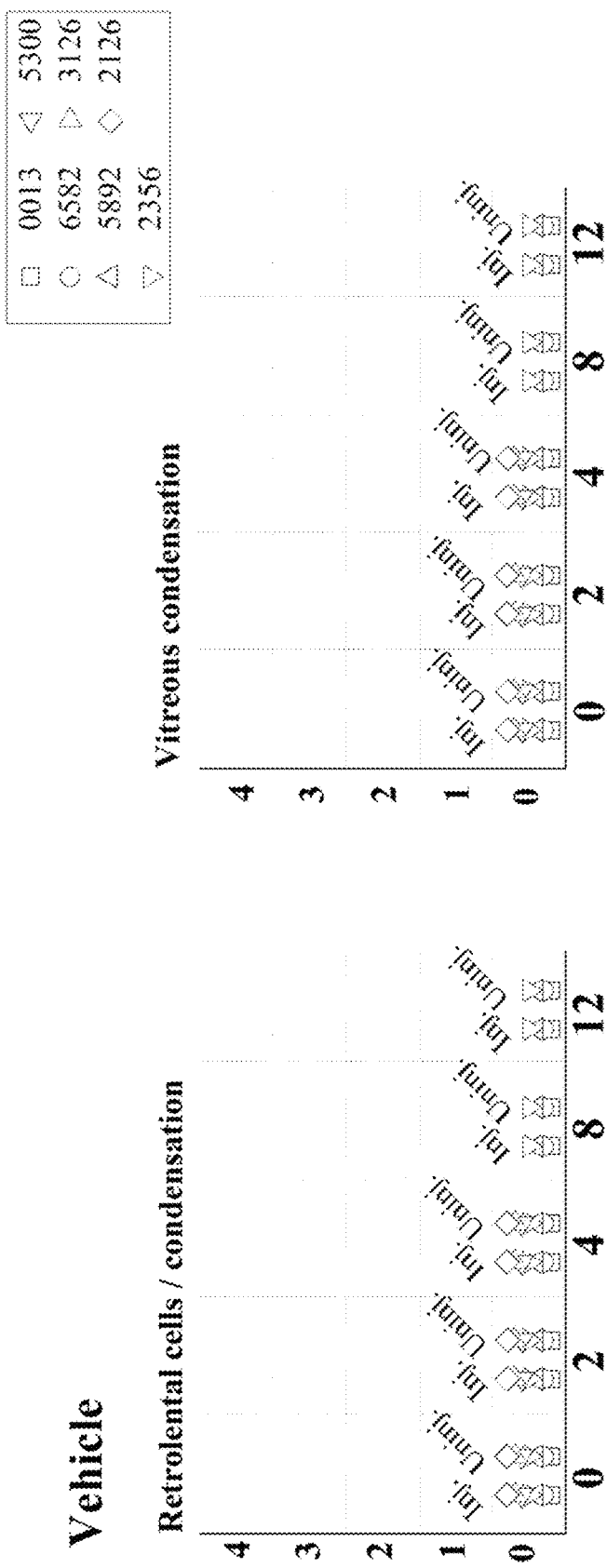
FIG. 10 depicts ophthalmological findings in New Zealand White rabbits injected intravitreally with 2 doses of either vehicle (A) or AAV8 scRS/IRBP hRS $2e^{10}$ vg/eye (B) or $2e^{11}$ vg/eye (C).
Figure 10B:
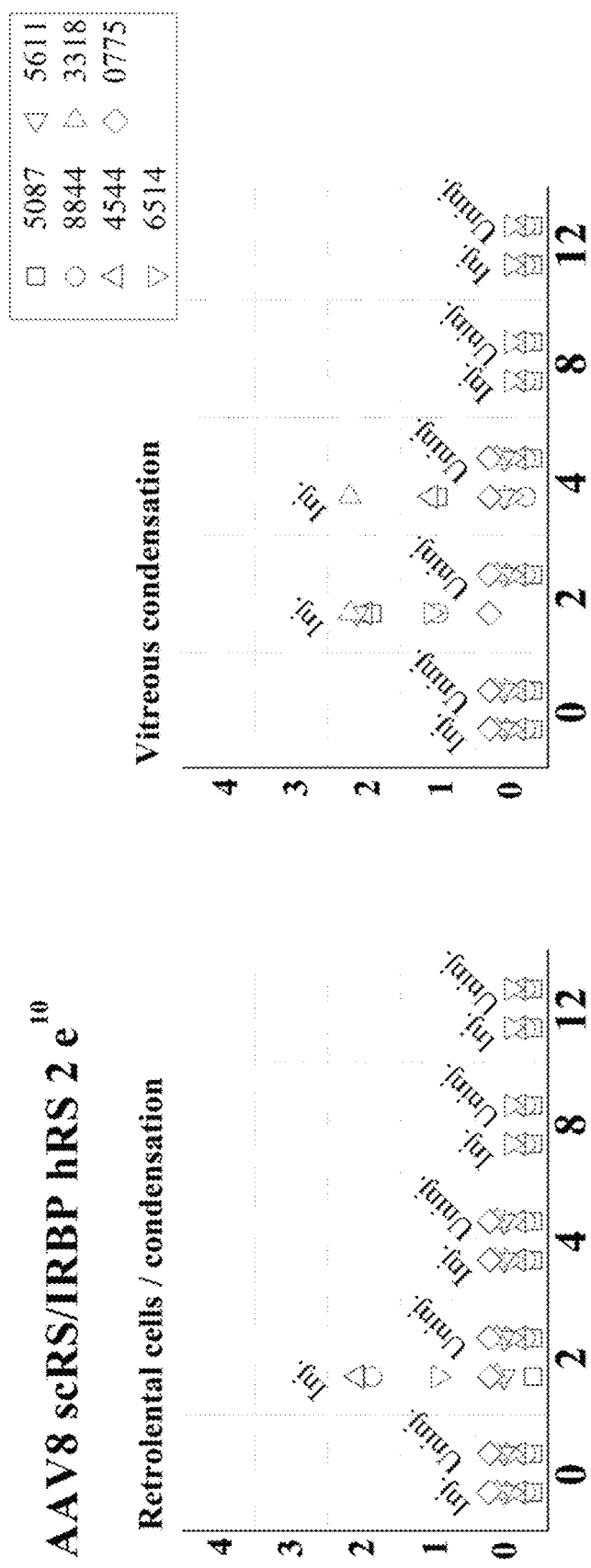
Figure 10C:
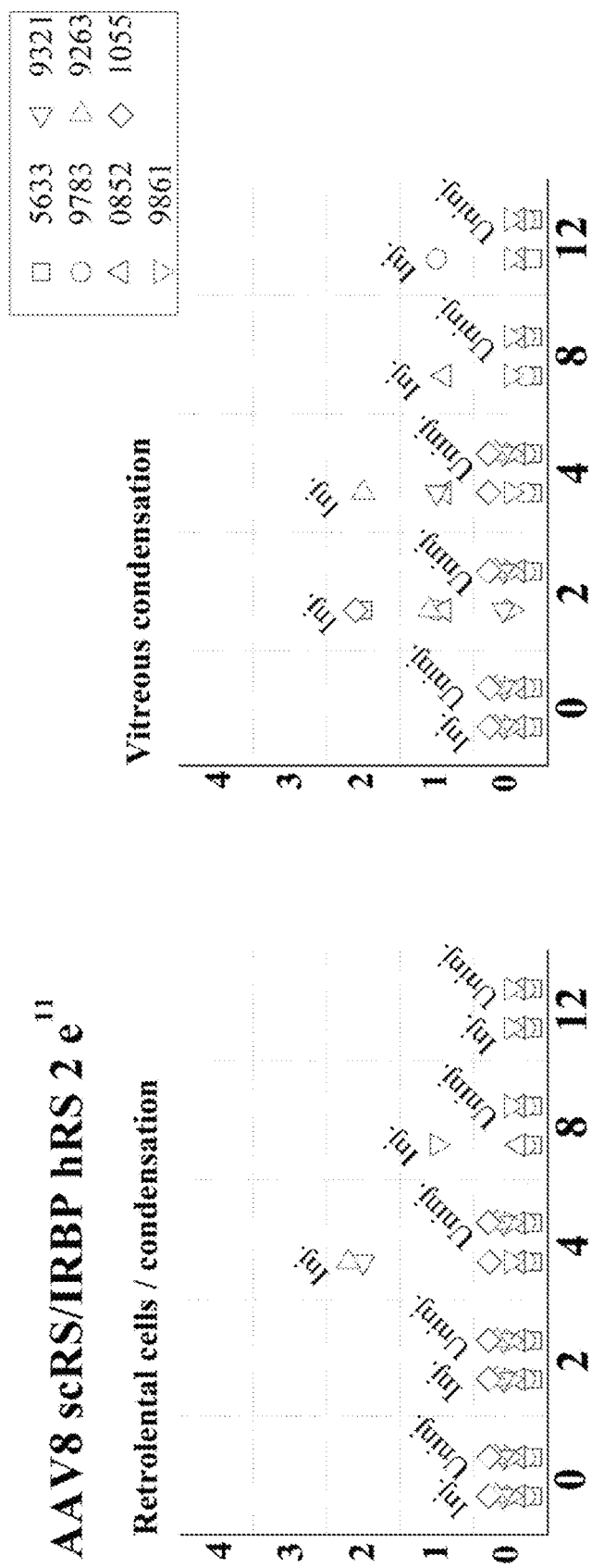

The results from this study are shown in FIG. 10. Findings from both the injected (Inj.) and uninjected eye (Uninj) are displayed for each animal at five time points (0, 2, 4, 8, 12 weeks) during the study. (n=4-7 rabbits/group). The data demonstrates that at two high doses (2 $e^{10}$ vg/eye or 2 $e^{11}$ vg/eye) of the expression vector injected into the rabbit eyes, only minimal inflammation post-injection (trace or mild) was detected in a few test animals. Mild inflammation resolved in most animals at both dosages over time.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of treating X linked retinoschisis (XLRS) in a human comprising:
    administering to a human subject diagnosed with XLRS by intravitreal or subretinal injection, a therapeutically effective amount of an AAV2 or AAV8 expression vector comprising:
        an expression cassette comprising an eye-specific promoter operably-linked to a nucleic acid sequence encoding a retinoschisin gene, including at least a 319-base pair portion of the first intron of the retinoschisin gene,
    wherein administration of the expression vector causes expression of a human retinoschisin protein in a retinal cell of the human subject, and reduces at least one symptom of XLRS in the subject.

2. The method of claim 1, wherein the vector is administered by intravitreal injection.

3. The method of claim 1, wherein the expression vector is administered by intravitreal injection from a polypropylene syringe.

4. The method of claim 1, wherein the expression vector is administered subretinally.

5. The method of claim 1, wherein the expression vector is administered at a dose between about $3e^8$ vg/eye to about $1e^{13}$ vg/eye.

6. The method of claim 1, wherein the expression vector is administered at a dose between about $1e^{10}$ vg/eye to about $1e^{13}$ vg/eye.

7. The method of claim 1, wherein the method further comprises administering the expression vector in combination with one or more additional active agents or supportive therapies for treating, preventing, or reducing the severity of XLRS in the subject.

8. The method of claim 7, wherein the one or more supportive therapies is selected from the group consisting of: surgery, photocoagulation, anti-angiogenic therapy, bevacizumab, ranibizumab, and Aflibercept, flunarizine and nifedipine, cryotherapy, hyperbaric oxygenation, topiramate, MK-801, dextromethorphan, eliprodil, and flupirtine, dimethylthiourea, alpha-lipoic acid, superoxide dismutase, catalase, desferrioxamine, mannitol, allopurinol, calcium dobesilate, flupirtine, trimetazidine, anti-inflammatory agents, cyclodiathermy, cyclocryotherapy, ocular filtering procedures, implantation of drainage valves, aspirin, ticlopidine, clopidogrel, warfarin and heparin, steroids, systemic or local corticosteroids, dexamethasone, cyclosporine, azathioprine, cyclophosphamide, mycophenolate, mofetil, infliximab and etanercept, vitamin C, vitamin E, lutein, zinc, folic acid, vitamin B6, vitamin B12, vitamin D, calcium, zeaxanthin, vitrectomy, scleral buckle surgery, pneumatic retinopexy, ciliary neurotrophic factor (CNTF) protein, brain-derived neurotrophic factor (BDNF) protein, pigment epithelium-derived factor (PEDF) protein, and lens epithelial derived growth factor (LEDGF).

9. The method of claim 7, wherein the expression vector is administered concurrently with a corticosteroid and a steroid-sparing immunosuppressant.

10. The method of claim 7, wherein the expression vector is administered concurrently with an anti-inflammatory agent selected from the group consisting of cyclosporine, mycophenolate mofetil, prednisone, and combinations thereof.

11. The method of claim 10, wherein the administration of the anti-inflammatory agent is initiated prior to the day of administration of the expression vector.

12. The method of claim 10, wherein the administration of the anti-inflammatory agent continues for at least 30 days after the administration of the expression vector.

13. The method of claim 7, wherein the expression vector is administered concurrently with a steroidal anti-inflammatory compound and a combination of calcium and Vitamin D supplements.

* * * * *